US012559764B2

(12) United States Patent
Tian et al.

(10) Patent No.: US 12,559,764 B2
(45) Date of Patent: Feb. 24, 2026

(54) MAIZE GENE ZmRAVL1 AND FUNCTIONAL SITE AND USE THEREOF

(71) Applicant: CHINA AGRICULTURAL UNIVERSITY, Beijing (CN)

(72) Inventors: Feng Tian, Beijing (CN); Jinge Tian, Beijing (CN); Chenglong Wang, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 460 days.

(21) Appl. No.: 17/617,142

(22) PCT Filed: Jun. 9, 2020

(86) PCT No.: PCT/CN2020/095099
§ 371 (c)(1),
(2) Date: Dec. 7, 2021

(87) PCT Pub. No.: WO2020/248971
PCT Pub. Date: Dec. 17, 2020

(65) Prior Publication Data
US 2023/0175000 A1      Jun. 8, 2023

(30) Foreign Application Priority Data
Jun. 10, 2019    (CN) .......................... 201910496614.6

(51) Int. Cl.
*C12N 15/82*      (2006.01)
*C07K 14/415*      (2006.01)
*C12Q 1/6895*      (2018.01)

(52) U.S. Cl.
CPC ........ *C12N 15/8213* (2013.01); *C07K 14/415* (2013.01); *C12N 15/8218* (2013.01); *C12N 15/8262* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

2014/0359836 A1      12/2014    Wu et al.
2017/0114356 A1      4/2017    Li et al.

FOREIGN PATENT DOCUMENTS

CN      106701967 A      5/2017
CN      109022450 A      12/2018
WO      2011/136909 A1      11/2011
WO      2016/124918 A1      8/2016

OTHER PUBLICATIONS

Je et al 2010 (The Plant Cell 22: p. 1777-1791). (Year: 2010).*
Tian et al 2019 (Science 365, p. 658-664) (Year: 2019).*
Butt et al 2018 (The Plant Cell 18:174 p. 1-9) (Year: 2018).*
Cowperthwaite et al 2002 (The Plant Cell 14: p. 713-726) (Year: 2002).*
Je et al 2002 (The Plant Cell 22: p. 1777-1791) (Year: 2002).*
Zhang et al 2014 (Journal of Experimental Botany 65:17 p. 5063-5076) (Year: 2014).*
GenBank Accession No. 001309881, Uncharacterized protein LOC103646035 [*Zea mays*]. 2 pages, Sep. 7, 2017.
Liu et al., A Teosinte Rare Allele Increases Maize Plant Density and Yield. Chin Bull Bot. 2019;54(5):554-557.
Tian et al., Teosinte ligule allele narrows plant architecture and enhances high-density maize yields. Science. Aug. 1, 20196;365(6454):658-664.
International Search Report and Written Opinion for Application No. PCT/CN2020/095099, dated Jan. 21, 2021, 12 pages.
Canadian Office Action for Application No. 3,142,548, dated Sep. 27, 2024, 12 pages.

* cited by examiner

*Primary Examiner* — Matthew R Keogh
(74) *Attorney, Agent, or Firm* — McCarter & English, LLP; Wei Song; Miao Yu

(57)      ABSTRACT

The present invention relates to a maize gene ZmRAVL1 and a functional site and use thereof. The present invention locates the functional site for controlling the leaf angle phenotype to 240 bp by fine-mapping, and the insertion and deletion of this region lead to different leaf angle phenotypes. The present invention demonstrates that an inbred line improved with an excellent natural variation from the teosinte can increase maize yield under dense planting and broaden the source of elite alleles available in plant breeding. The present invention demonstrates that a reduced ZmRAVL1 expression by a genetic engineering technique (RNAi) has an influence on plant architectures, such as a reduced leaf angle, and thus it provides excellent genetic resources for genetic engineering breeding. The present invention produces favorable alleles by adopting the gene-editing technology, and thus greatly shortens the selection process of elite alleles, which provides a new idea for obtaining elite alleles available in the breeding practice. The present invention can quickly and accurately improve or produce superior inbred lines with the aid of the molecular marker-assisted selection technology, which provides the possibility of wide application of elite alleles.

17 Claims, 18 Drawing Sheets
Specification includes a Sequence Listing.

GCGGTTGGCGTGCTAGCTTTGATCCCCCATATCATGACAAGGACGAGCTCACATGAGCCCAACCAGCTGATTCATGCG

GGCCCCACCCTACTCCCGCCATCATCCTCTCCTCACTCACCACCCGCCCGGCCCGGCCTCCTCCCTGCAAAGCTACACTACA

CAGCGCGCGGCTGCTGCACCACAGCCTACTTTCCCCCGGCCGGCCTGCTGCCTAATTACCTGCTCATCAACTACCGGAGCCA

TTCACATTCAATATGTACTTTCTTTCTTCCTTTTTTTTTACCGCGTGGTCAGCAGACGACGCAAATTCCCACCCCCCGAAAT

TCAAAGGGACAGACATCAGCGCATTGGCTTTTTTTTGGCTATATATGGACATGCATGTGCTATGTGTGTGTTTAGCGGTATA

AGTTTATGCACATCATCATTTCTTGCCTAGCAATTCATGGGGACTACCCCAGGCCTTGTTCGTTTGTGTCGGATCGGTGGGT

CGAAACGATTCTTAACCGGATTGCTTCTCTAATTTATATAAACTTTGATTAACTTGAACGATTTCGGGTGTAATCCGACACA

AACGAACAAGACCTCATTATTTTCGAAGAAAAGGTTGGCACGGATTTGTGCGTTGGCGCCTTTTACATGAACCGTTTCGTTC

AACGTCTTGCTAATGCTGGGTATATATATAAATGCAGTGTGCTGTGTGCGTTGGCTTTATTTATTTCAAAGAAAAGAAAGCA

CCCATTTCTTGCCTAACTAGTCTATACTATACTTAAAGCACCAGTTTCAACGGTCGTCATGCGTCATTTTTTTTACAAATAA

CCTCTCACAGCTATTTCAAATTAATCCGATGCACATCTATAGATGCCAAACGACGCCCGACACGAGCTAGATATACGCAAGC

CACAACTATGGCACAGACACGTCATGCCGGCCTGCTAACTGTGTCGGGCCAGCCCGTTAGCCCGTCGATCCATTTAATTAAA

TCAGCGTAACGACGCCCGACACGGGCTAGATGCACGCGGCCTGCTAACTATGTCGGGCCAGCCTATTAGGTCGTCGATCCAT

TTAATTAAATTAGCGTAAAATGTTAAAAAACGGTGTTGGAGTTGGGGTTTGAACCATGCCCTGATGGAAGAAGGGCGGGAGA

CACTGGGTGAAACTGTTTAACCAGTAGAACATCACACTAAAATATTTTTAATATTGAATATAAATTGTATATAGGTATATAC

GTTTTTTTGTAAAATAAAAAAATAATCGTGTCGGGCCGGGCCAGCACTACGGGCTGAGGCTACAGCCCAAGCACGGCACGAC

GTCCTTGGCTCTTGCAAGCATTAGGTCGTTTCTGAGACCACATTAGCGCAATGGACTACATGGTGTTTGAGGTTGCTGAATT

GGATGGAGTAGCAATGATTTGTCACACTAACAGCAAAATGAAAGGTCATTTGTTGGTTTTAAACGTTAGTAATTGCTACGAA

GTAGCATAATTTATATGGAGCACATCCAATTTTTATTGATGCCTGACTTTAGCAATCACTCCATATTTTGATCTATCTTTTT

TATAAGTTTGACTTCATGAGACTTATTTTAGAAACTTGATCTCACAAACTTTCTCTTATTTGGTCTATGTATGATGGAATTA

TGTCATTTTATAATATCTGTTTATTCAGTCAACCGTTGTGAACTATCTTATAATCGCTCACTTCATTGGCCGTGTTGTACCA

AGACATATTTGTATGGAGTAAATAATAACATCAGTTAGTCAAATAAAAAATATATTATATAAAGAGAGGAGACAATCAATAA

AAAATCTTGAATTTTTTTGATAGATAGTATACGTGGGTATTGTTGTAAGCCGTCGCAACGCACGGACAACCGACTAGTGTTA

TTCAATAGACCGGCCGGAAAACACAATACTGAAAGAAGGCAAAGCATGCAGTAGGACCATGCAATACGCTGCTTGAAGCTAA

GGACATGTTTAAAAGTCTCCGGTTTTTAAGAAACTAGTTTATAAAAATAGAAGTGATTCTAAACATATCGATTTCTTAGAAA

CTAGATTCTCAGTTTCTTAAAAACCAAGAATCTAGCTCCTCTAACTAAAACTAGTTTATAGAAGTTTCTTAAAAACCAAGAA

TCTAGCTTCTCTAACTAAAACTAGTTTATAGAAATTGAGATGGTTCCAAACACTATTAACTATTGTTTTTTCATAACCCAGT

TTCAAAAACACTAGAAATCGAAAGTGCATTCTTAAAAACTAGGTTGTTTGTAAACATGGTCCTACAACTCAGCAGTAACTCT

CAGAATAGAAATGCATAATGCAATGCACCATTATATTCCTACTAGGAATAGGAATACGATCGGTAGGGTGCGCCCGGCCACC

TTCGAGGAATCTTCTAGGGCAGTCAGTGCCCCCCCTCCGTGTGTGTCTCCCTCCCCTCGCCAGCTCGCATCCCCGCCCTGTG

GGCAGTGGCCAGTGGGCTGGGCTGGAATGGAACTCCCTCCTCCCGGCCCTTGTGGGCGCGCAGCAAGCGGCTAGCAGCTTTC

CCACAGCTCGCTTTACCCCTCCCAACAAGCGCCACCAATCGCTGGAGACTGGAGAGAGAGAAGAACCAGCCACACAACTCTA

ATTACCACGCACTCTCTCTCTCTCCGTCCTATCGATCCCGGCCTCCCTCCCCCAGCCCCAGCGGATCGGAGCCCCCGGCT

GGCTTCCTACCCTGCCCCCTCTTCCTCCGACGCGCGGGCGGAGGAGTTCGATCCGAGCGCGAGAGGGAAGGAGAGAGAAACT

AAAGAAAGAGAGGGGCAGAGAGCAGACAGATAGGAGTGGTAGATATAGATAGGCTGGGGCTGGCCTCATCGCGGATAGATCC

CCCTCCTCCTCCTCCTCACTCTCCCCAGCGAGCAAGCAACCAAGCAGCCAGCTAGTCAGTCTCCGCCAAGCAGGGACCGCGT

CGCATCAAAGCCGCTGCCCGCAACAGGGACAAGGCAGGCCAGCGCGCGCTCGAAAGGGGAGGCGTCGTTCTACACGAAGACG

AGGAGGAGGAGCCCTGCAGGGCGTAGCTAGCATGGAGTTCGCGAGCTCTTCGAGTAGGTTTTCCAGGGAGGAGGACGAGG

AGGAAGAGCAGGAGGAAGAGGAGGAGGAGGAGGAGGCGTCTCCGCGCGAGATCCCCTTCATGACAGCGGCAGCGACGGCCGA

Figure 2A

CACCGGAGCCGCCGCCTCCTCGTCCTCGCCTTCCGCGGCGGCCTCATCGGGTCCTGCTGCTGCCCCCCGCTCGAGCGACGGC

GCCGGGGCGTCCGGGAGCGGCGGCGGCGGGAGCGACGACGTGCAGGTGATCGAGAAGGAGCACATGTTCGACAAGGTGGTGA

CGCCCAGCGACGTGGGGAAGCTCAACCGGCTGGTGATCCCGAAGCAGCACGCGGAGAAGTACTTCCCGCTGGACGCGGCGGC

CAACGAGAAGGGCCAGCTGCTCAGCTTCGAGGACCGCGCCGGTAAGCTCTGGCGCCTTCCGCTACTCCTACTGGAACAGCAGC

CAGAGCTACGTCATGACCAAGGGCTGGAGCCGCTTCGTCAAGGAGAAGCGCCTCGACGCCGGCGACACCGTCTCCTTCTGCC

GCGGCGCCGGCGACACCGCGCGGGACCGCCTCTTCATCGACTGGAAGCGCCGCGCCGACTCCCGCGACCCGCACCGCATGCC

GCGCCTCCCGCTCCCCATGGCGCCCGTCGCGTCGCCCTACGGCCCCTGGGGCGGCGGCGGCGGCGGCGGCGCGGGCGGTTTC

TTCATGCCGCCCGCGCCGCCCGCCACACTCTACGAGCACCACCGCTTCCGCCAGGCCCTCGACTTCCGCAACATCAACGCCG

CGGCCGCGCCGGCCAGGCAGCTCCTCTTCTTCGGCTCAGCCGGCATGCCCCCGCGCGCGTCCATGCCGCAGCAGCAGCAGCC

GCCTCCGCCCCCGCACCCGCCCTCTGCACAGCATTATGTTGGTGCAACCCAGCCCCGCGCCGCCCACGGCCAGCGTGCCCATG

CTTCTCGACTCGGTACCGCTCGTCAACAGCCCAACGGCAGCGTCGAAGCGCGTCCGCCTGTTTGGGGTCAACCTCGACAACC

CGCAACCAGGCACAAGTGCGGAGTCAAGCCAAGATGCCAACGCATTGTCGCTGAGGACACCGGGATGGCAAAGGCCGGGGCC

GTTGAGGTTCTTCGAATCGCCTCAACGCGGCGCCGAGTCATCTGCAGCCTCCTCGCCGTCGTCATCGTCGTCCTCCAAGAGA

GAAGCGCACTCGTCCTTGGATCTCGATCTGTGAGCGAGAGATCGATCAGCTGGCGAACTCGATCGATCGGGGGAGTAAAAA

AGGAAAGTTGAAAATTTCCTCCTTCCGTCTGCTACCTTCTTCTTCACCTTTTGAGATTCCATTATAACTTTTGATCATAGGA

TCTAGAGTAGCCTTCTTAACACTTGTTCTCCGATTTTTCTTTCGGCCATTCAAATTCTTGTGCTGGCTTGACAATATATATA

GAGAGAAGTTAGGCGAATTAATTAATCAATTATTGTTGCTTTCATATGGCTTGAAATCTGACTCGGTTTTTGCTTCGCTACT

ATTGCTTTATCCTTTTTTTGCTGGTATGATTGGACTCCTTAAGGTACCATTTCACTCTTATGTAGTTTGGTTGCACAATTCC

GATTGTCGTATGTTCCTACTCCCTACATATGATAACACAACTCCAAATTCGCGCTCTCCACACCATCACTGCTAAGATCTGA

ATCCCTAGCACCATGAATGCGGTGCAATATACATCGTGCCTTTCTTGCATCATATGTGTGATCTGTTCTCGTCCTAGATTGG

AGTTGCAACCGCAGTGTTCTCAGAAAGCATGGCAAGACAAGAACATTGACAGTCCATGTCCATCAGCAGCACTCAACTTACA

GCCGGCAAAGCCTATGGAGCTAGCTAGAAGCATTTGCAGGTCAGTTGTTTAACTTCTGAATCGTCTCATCTTCTTTCATCGG

TACTGCTCACCATCTCTCTTGTTTATATTATGAGTCCTGGTGCTGGCACTCTTGTTTTCATTTTCGTGCTTTTGCCGGTTGC

CACTTTTCTGTACTGTTGCTCACTCTTTGTCCATACTACATATGTATACCATGGTGCATCATGCCATAATGTAGTAGATCGT

ATGGTAGGCAGTTAGTTGCTACGCGCGCACCACCACACAAGCAAACTGGAAGACTTCTCTTGTGCTTTTACGCAAGGTCAAC

TGAAAATTAACCCTACCGTGGGCTAAATCATGTCATGTGTAGTACGTTTGATTTGTCTGGGCCTTGAGTGGTATAGACTCCA

ATAGTTCTTTATGGCCCTCTGGCAGTCTGTAAAGGAGAGGGTGAGCCAGAGGGGAAGGCATTGCTACTGGCCTTAACTTCTT

TGTACGTCTGATGGACGATTTATTGGGGAAGAGCCGAAGAGGGCCAGCCTCAGTACTAACACTACTGTTTCTGTAGTAGTAG

GAACAGTGCTGCGTCGATATGCATCTCTCTCTCATGGAGATGGAGAGCCTTGGTTGCGTTCTGTGTTCTTGTCCTTTGTGTG

CGAGAGACAGTGAGGAGAGAGACTGTACATTACCGTCTCTCCTCTTTTTTTTTTCTCTCTCTCTCCTTTCACTGCATTGAGT

AGGTACGGCGTGTGTGCTAGCTCCTTGCTGGGAGCAATGGAGGCAAATGCCACGTACCGGCTCAGCAATAGGTATCCTTAAC

TAGTAAGGTGTAGGAGGGGGATCTTTTTGCACTGCTGAGGCTAGAATAGACATGTATAGATGCTGTGTCTACTGACAAAAGT

ACCTTTGGTACGTTGTAAGCTGGAAAAGGCAATGGGGAGTTATGGGGGAGGGAAAAAAAAAGAGCCAGGAGCAGTGTCTGCA

TGCATGTTTTTGCTTGTTATACGTTCTTTCTACCCTTTGCATATGGTTGTTCAATTCATCTTTCTTTTCTGATCATACAGCC

CTGAGTCGGGGTATTATCTCAAGAACAGCGTCTTGTGACCTCGATCTCACAAAGAATATAGGAAGTCCTCCATATAAACTAC

ATTTGTGGAAACAAAAAATTGAAAATCATGTGTAATTTAGACTCTTACAGGCGAAATATGTAAATGCTAATTAACTAACATA

TTCTGTCGTTTAGCAAGGAAGATGCATTGAGATGAATAGCCAAGTTCGTTAATTGTCCAAGCATAAGTTGCACTCCATTGCC

ATTTTTTGTAGAACACATGTTGGCGCATACCATACCTTGGTTAATCACGCTGTCACTGTGATATGTTAGACCTACTATAGCC

AATGACCATTATCTCAAATAATGATGTGATGACTGAATGATCAGGCTAATTATTGCATAATGCGTATACTAGTTCCGTATTG

Figure 2B

ATTTTTCTGCGGTTATTATCCTCCTTCATATTCCTAGAGAGAAAGGGCTGAATTTTGGCGCTCATATAAAGAACATAACCAC

ATCTCTGTTATATTACTCTTTGTACGTACATGCAAGATATGTTACACATACAAAAAAGATGAGGTGGATATCATGTATCTGT

ATAGCTTGAAATGCTGAGGTATATTGATATTTATTGCTTTTGACAGTTTCATTGACATCTCCATCGCTATGGAAATCATTTC

ATGCACTACATTTCTGAAGAAACTTA

Figure 2C

MEFASSSSRFSREEDEEEEQEEEEEEEEASPREIPFMTAAATADTGAAASSSSPSAAASSGPAAAPRSSDGAGASGSG

GGGSDDVQVIEKEHM DKVVTPSDVGKENRLVIPKQHAEKYFPLDAAANEKGLLSFEDRAGKIWRFRYSYWNS

SQSYVMTKGWSRFVKEKRLDAGDIVSFGRGAGDTAHDRIFIDWRRR DSRDPHRMPRLPLPMAPVASPYGPWGG

GGGGGAGGFFMPPAPPATLYEHHRFRQALDFRNINAAAAPARQLLFFGSAGMPPRASMPQQQQPPPPPHPPLHS

IMLVQPSPAPPTASVPMLLDSVPLVNSPTAASKRVRLFGVNLDNPQPGTSAESSQDANALSLRTPGWQRPGPLRFF

ESPQRGAESSAASSPSSSSSSKREAHSSLDLDL

Figure 3

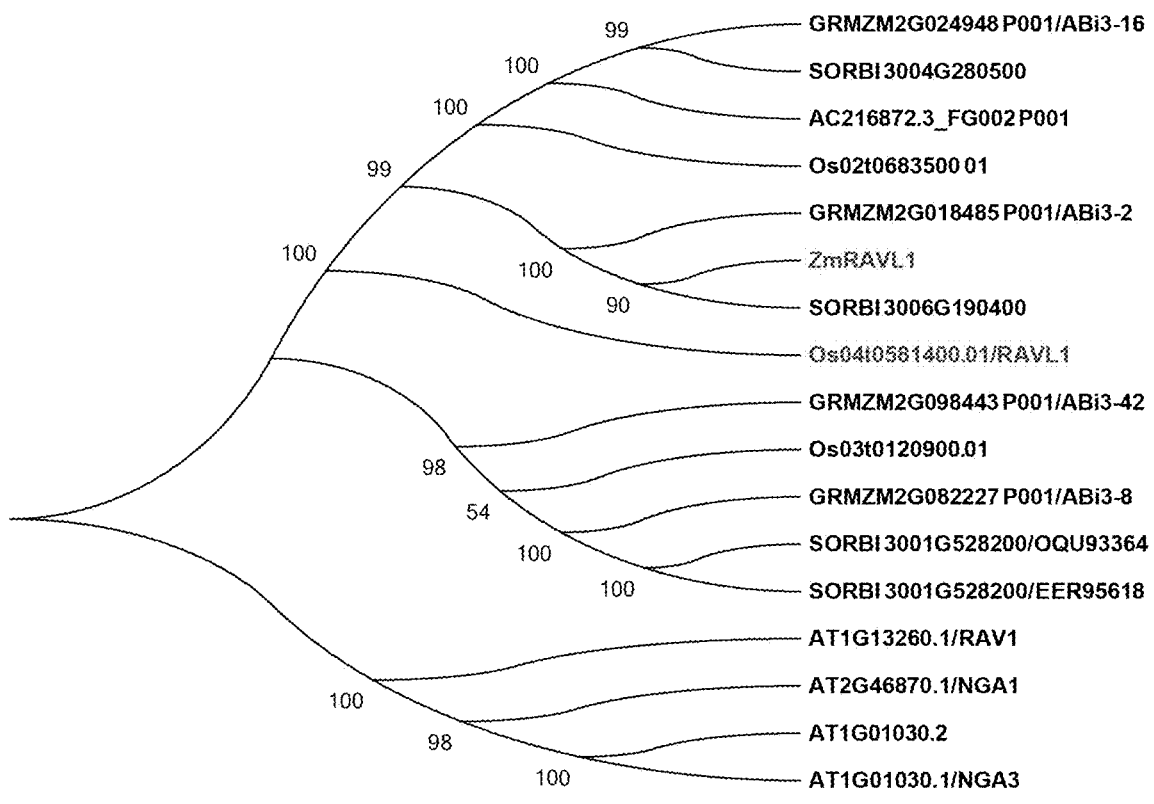

Figure 4

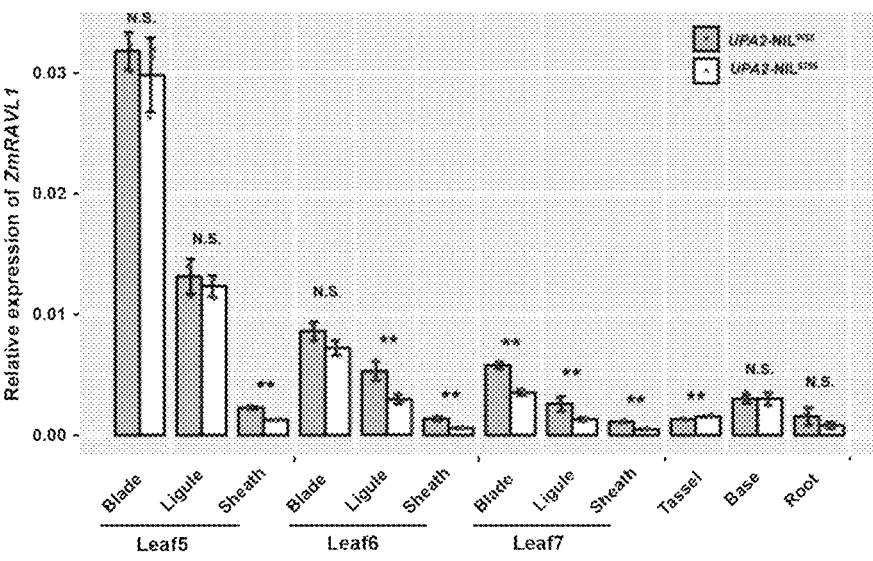
Figure 9
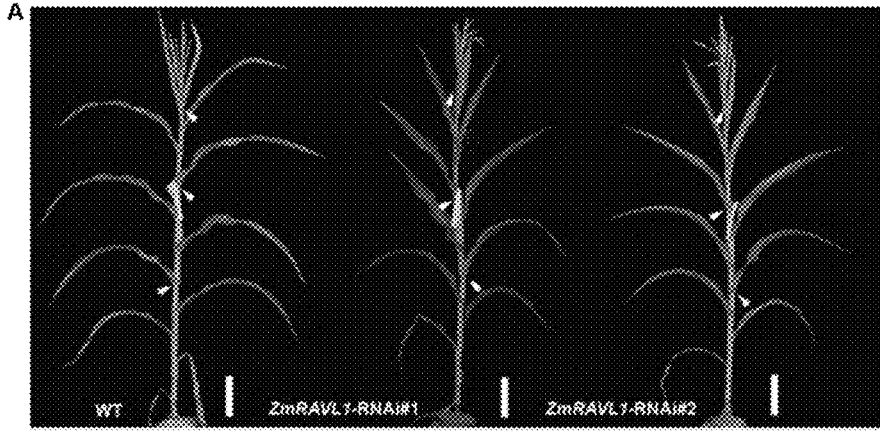
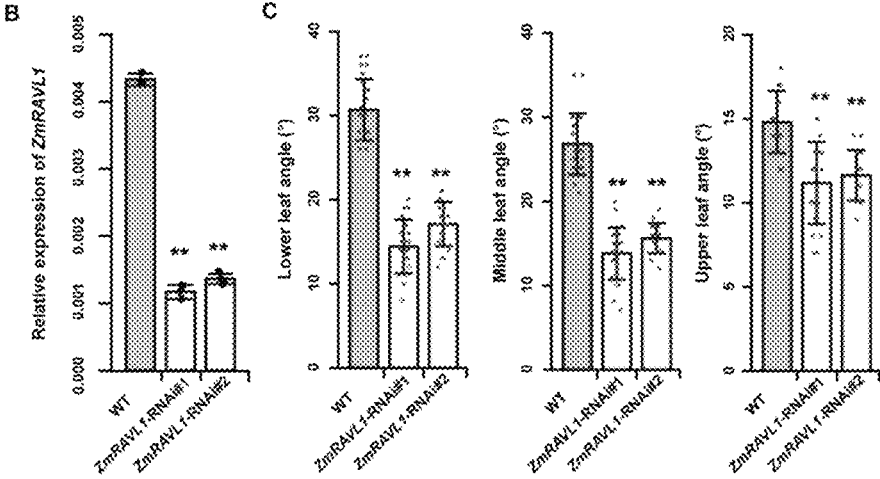
Figure 10

SEQUENCE LISTING

```
<160> NUMBER OF SEQ ID NOS: 75

<210> SEQ ID NO 1
<211> LENGTH: 243
<212> TYPE: DNA
<213> ORGANISM: Maize
<220> FEATURE:
<223> OTHER INFORMATION: maize wide-type species Teosinte 8759

<400> SEQUENCE: 1
atagaagaga gtgatcactg tttttgtggt tgttcagctt ttactatccc tgggaaaaaa      60
agtgtcagca gtaatctact ttgagtagtg tttccataga aaacaaaact gcgcatgcgc     120
gcgctgagtg tggtccttct cttttaatta ctactgcgtg gtgtgtgtgt gctgccaaca     180
gtagtaacca tctggcacct ccctatattt ttcaggaaaa attaaatgaa ctgtactaat     240
tca                                                                   243

<210> SEQ ID NO 2
<211> LENGTH: 240
<212> TYPE: DNA
<213> ORGANISM: Maize
<220> FEATURE:
<223> OTHER INFORMATION: Maize inbred line W22

<400> SEQUENCE: 2
atagaagaga gtgatcactg tttttgtggt tgttcagctt ttactatccc tgggaaaaaa      60
aagtgtcagc agtaatctac tttgagtagt gtttccatag aaaacaaaac tgcgcatgcg     120
cgcgctgagt ggtccttctc ttttaattac tactgtgtgg tgtgtgtgct gccaacagta     180
gtaaccatct ggcacctccc tatatttttc aggaaaaatt aaatgaactg tactaattca     240

<210> SEQ ID NO 3
<211> LENGTH: 26
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 3
catctatctc tgatacacac atgcag                                           26

<210> SEQ ID NO 4
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide
```

-continued

```
<400> SEQUENCE: 4
atcagacact gcactgcaca                                                   20

<210> SEQ ID NO 5
<211> LENGTH: 22
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 5
ctacaccata gtgtgctgct ct                                                22

<210> SEQ ID NO 6
<211> LENGTH: 24
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 6
gcaatttacg aaatttaaac tgga                                              24

<210> SEQ ID NO 7
<211> LENGTH: 26
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 7
gagcacatct tattttatga caaaca                                            26

<210> SEQ ID NO 8
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 8
attgcgctag caggattcat                                                   20

<210> SEQ ID NO 9
<211> LENGTH: 21
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 9
ggattgcgga aagaaagaac c                                                 21

<210> SEQ ID NO 10
<211> LENGTH: 23
<212> TYPE: DNA
<213> ORGANISM: artificial sequence
<220> FEATURE:
<223> OTHER INFORMATION: Description of Artificial Sequence: Synthetic
      oligonucleotide
```

```
<400> SEQUENCE: 10
aggcaaacat cttcaagttc aca                                          23

<210> SEQ ID NO 11
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 11
ttgagctcgt acgtgtctgg                                              20

<210> SEQ ID NO 12
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 12
tggcaacaca aacagtgaca                                              20

<210> SEQ ID NO 13
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 13
gtacgtggca gagctagact                                              20

<210> SEQ ID NO 14
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 14
ctcgcagttg ataccaccct                                              20

<210> SEQ ID NO 15
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 15
tccagaagac tcgtgctgaa                                              20

<210> SEQ ID NO 16
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide
```

<400> SEQUENCE: 16
cccacttcct gtacgtacgt                                              20

<210> SEQ ID NO 17
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 17
catgtgggac cggaatcaga                                              20

<210> SEQ ID NO 18
<211> LENGTH: 21
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 18
actttagaca gtgacgacct c                                            21

<210> SEQ ID NO 19
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 19
gcttgcttct tcgcctacaa                                              20

<210> SEQ ID NO 20
<211> LENGTH: 22
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 20
ccagatggtt actactgttg gc                                           22

<210> SEQ ID NO 21
<211> LENGTH: 22
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 21
ccatagaaaa caaaactgcg ca                                           22

<210> SEQ ID NO 22
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide -continued

```
<400> SEQUENCE: 22
tccttcctct cccaaccaac                                               20

<210> SEQ ID NO 23
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 23
cgtgcctttc ttgcatcata                                               20

<210> SEQ ID NO 24
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 24
ttgtcttgcc atgctttctg                                               20

<210> SEQ ID NO 25
<211> LENGTH: 7
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 25 gagtgtg                                                             7

<210> SEQ ID NO 26
<211> LENGTH: 6662
<212> TYPE: DNA
<213> ORGANISM: Maize
<220> FEATURE:
<223> OTHER INFORMATION: maize wide-type species Teosinte 8759

<400> SEQUENCE: 26
gcggttggcg tgctagcttt gatcccccat atcatgacaa ggacgagctc acatgagccc    60
aaccagctga ttcatgcggg ccccacccta ctcccgccat catcctctcc tcactcacca   120
cccgcccggc ccggcctcct ccctgcaaag ctacactaca cagcgcgcgg ctgctgcacc   180
acagcctact ttcccccggc cggcctgctg cctaattacc tgctcatcaa ctaccggagc   240
cattcacatt caaatatgtac tttctttctt cctttttttt taccgcgtgg tcagcagacg   300
acgcaaattc ccacccccg aaattcaaag ggacagacat cagcgcattg gctttttttt   360
ggctatatat ggacatgcat gtgctatgtg tgtgtttagc ggtataagtt tatgcacatc   420
atcatttctt gcctagcaat tcatggggac taccccaggc cttgttcgtt tgtgtcggat   480
cggtgggtcg aaacgattct taaccggatt gcttctctaa tttatataaa ctttgattaa   540
cttgaacgat ttcgggtgta atccgacaca aacgaacaag acctcattat tttcgaagaa   600
aaggttggca cggatttgtg cgttggcgcc ttttacatga accgtttcgt tcaacgtctt   660
gctaatgctg ggtatatata taaatgcagt gtgctgtgtg cgttggcttt atttatttca   720
aagaaaagaa agcacccatt tcttgcctaa ctagtctata ctatacttaa agcaccagtt   780
```

-continued

```
tcaacggtcg tcatgcgtca ttttttttac aaataacctc tcacagctat ttcaaattaa      840
tccgatgcac atctatagat gccaaacgac gcccgacacg agctagatat acgcaagcca      900
caactatggc acagacacgt catgccggcc tgctaactgt gtcgggccag cccgttagcc      960
cgtcgatcca tttaattaaa tcagcgtaac gacgcccgac acgggctaga tgcacgcggc     1020
ctgctaacta tgtcgggcca gcctattagg tcgtcgatcc atttaattaa attagcgtaa     1080
aatgttaaaa aacggtgttg gagttgggggt ttgaaccatg ccctgatgga agaagggcgg     1140
gagacactgg gtgaaactgt ttaaccagta gaacatcaca ctaaaatatt tttaatattg     1200
aatataaatt gtatataggt atatacgttt ttttgtaaaa taaaaaaata atcgtgtcgg     1260
gccgggccag cactacgggc tgaggctaca gcccaagcac ggcacgacgt ccttggctct     1320
tgcaagcatt aggtcgtttc tgagaccaca ttagcgcaat ggactacatg gtgtttgagg     1380
ttgctgaatt ggatggagta gcaatgattt gtcacactaa cagcaaaatg aaaggtcatt     1440
tgttggtttt aaacgttagt aattgctacg aagtagcata atttatatgg agcacatcca     1500 attttttattg atgcctgact ttagcaatca ctccatattt tgatctatct tttttataag     1560
tttgacttca tgagacttat tttagaaact tgatctcaca aactttctct tatttggtct     1620
atgtatgatg gaattatgtc attttataat atctgtttat tcagtcaacc gttgtgaact     1680
atcttataat cgctcacttc attggccgtg ttgtaccaag acatatttgt atggagtaaa     1740
taataacatc agttagtcaa ataaaaaata tattatataa agagaggaga caatcaataa     1800
aaaatcttga attttttttga tagatagtat acgtgggtat tgttgtaagc cgtcgcaacg     1860 cacgacaac cgactagtgt tattcaatag accggccgga aaacacaata ctgaaagaag     1920
gcaaagcatg cagtaggacc atgcaatacg ctgcttgaag ctaaggacat gtttaaaagt     1980
ctccggtttt taagaaacta gtttataaaa atagaagtga ttctaaacat atcgatttct     2040
tagaaactag attctcagtt tcttaaaaac caagaatcta gctcctctaa ctaaaactag     2100
tttatagaag tttcttaaaa accaagaatc tagcttctct aactaaaact agtttataga     2160
aattgagatg gttccaaaca ctattaacta ttgtttttttc ataacccagt ttcaaaaaca     2220
ctagaaatcg aaagtgcatt cttaaaaact aggttgtttg taaacatggt cctacaactc     2280
agcagtaact ctcagaatag aaatgcataa tgcaatgcac cattatattc ctactaggaa     2340
taggaatacg atcggtaggg tgcgcccggc caccttcgag gaatcttcta gggcagtcag     2400 tgcccccccct ccgtgtgtgt ctccctcccc tcgccagctc gcatccccgc cctgtgggca     2460
gtggccagtg ggctgggctg gaatggaact ccctcctccc ggcccttgtg ggcgcgcagc     2520
aagcggctag cagctttccc acagctcgct ttacccctcc caacaagcgc caccaatcgc     2580
tggagactgg agagagagaa gaaccagcca cacaactcta attaccacgc actctctctc     2640
tctctccgtc ctatcgatcc cggcctcctt ccccagccc cagcggatcg gagccccgg      2700 ctggcttcct accctgcccc ctcttcctcc gacgcgcggg cggaggagtt cgatccgagc     2760
gcgagaggga aggagagaga aactaaagaa agagaggggc agagagcaga cagataggag     2820
tggtagatat agataggctg gggctggcct catcgcggat agatccccct cctcctcctc     2880
ctcactctcc ccagcgagca agcaaccaag cagccagcta gtcagtctcc gccaagcagg     2940
gaccgcgtcg catcaaagcc gctgcccgca acagggacaa ggcaggccag cgcgcgctcg     3000 aaagggggagg cgtcgttcta cacgaagacg aggaggagga gccctgcagg gcgtagctag     3060
ctatggagtt cgcgagctct tcgagtaggt tttccaggga ggaggacgag gaggaagagc     3120
aggaggaaga ggaggaggag gaggaggcgt ctccgcgcga gatcccctttc atgacagcgg     3180
```

-continued

```
cagcgacggc cgacaccgga gccgccgcct cctcgtcctc gccttccgcg gcggcctcat      3240
cgggtcctgc tgctgccccc cgctcgagcg acggcgccgg ggcgtccggg agcggcggcg      3300
gcgggagcga cgacgtgcag gtgatcgaga aggagcacat gttcgacaag gtggtgacgc      3360
ccagcgacgt ggggaagctc aaccggctgg tgatcccgaa gcagcacgcg gagaagtact      3420
tcccgctgga cgcggcggcc aacgagaagg gccagctgct cagcttcgag gaccgcgccg      3480
gtaagctctg gcgcttccgc tactcctact ggaacagcag ccagagctac gtcatgacca      3540
agggctggag ccgcttcgtc aaggagaagc gcctcgacgc cggcgacacc gtctccttct      3600
gccgcggcgc cggcgacacc gcgcgggacc gcctcttcat cgactggaag cgccgcgccg      3660
actcccgcga cccgcaccgc atgccgcgcc tcccgctccc catggcgccc gtcgcgtcgc      3720
cctacggccc ctggggcggc ggcggcggcg gcggcgcggg cggtttcttc atgccgcccg      3780
cgccgcccgc cacactctac gagcaccacc gcttccgcca ggccctcgac ttccgcaaca      3840
tcaacgccgc ggccgcgccg gccaggcagc tcctcttctt cggctcagcc ggcatgcccc      3900
cgcgcgcgtc catgccgcag cagcagcagc cgcctccgcc cccgcacccg cctctgcaca      3960
gcattatgtt ggtgcaaccc agcccgcgcg cgcccacggc cagcgtgccc atgcttctcg      4020
actcggtacc gctcgtcaac agcccaacgg cagcgtcgaa gcgcgtccgc ctgtttggtg      4080
tcaacctcga caacccgcaa ccaggcacaa gtgcggagtc aagccaagat gccaacgcat      4140
tgtcgctgag gacaccggga tggcaaaggc cggggccgtt gaggttcttc gaatcgcctc      4200
aacgcggcgc cgagtcatct gcagcctcct cgccgtcgtc atcgtcgtcc tccaagagag      4260
aagcgcactc gtccttggat ctcgatctgt gagcgagaga tcgatcagct ggcgaactcg      4320
atcgatcggg ggagtaaaaa aggaaagttg aaaatttcct ccttccgtct gctaccttct      4380
tcttcacctt ttgagattcc attataactt ttgatcatag gatctagagt agccttctta      4440
acacttgttc tccgattttt ctttcggcca ttcaaattct tgtgctggct tgacaatata      4500
tatagagaga agttaggcga attaattaat caattattgt tgctttcata tggcttgaaa      4560
tctgactcgg tttttgcttc gctactattg ctttatcctt tttttgctgg tatgattgga      4620
ctccttaagg taccatttca ctcttatgta gtttggttgc acaattccga ttgtcgtatg      4680
ttcctactcc ctacatatga taacacaact ccaaattcgc gctctccaca ccatcactgc      4740
taagatctga atccctagca ccatgaatgc ggtgcaatat acatcgtgcc tttcttgcat      4800
catatgtgtg atctgttctc gtcctagatt ggagttgcaa ccgcagtgtt ctcagaaagc      4860
atggcaagac aagaacattg acagtccatg tccatcagca gcactcaact tacagccggc      4920
aaagcctatg gagctagcta gaagcatttg caggtcagtt gtttaacttc tgaatcgtct      4980
catcttcttt catcggtact gctcaccatc tctcttgttt atattatgag tcctggtgct      5040
ggcactcttg ttttcatttt cgtgcttttg ccggttgcca ctttttctgta ctgttgctca      5100 ctctttgtcc atactacata tgtataccat ggtgcatcat gccataatgt agtagatcgt      5160
atggtaggca gttagttgct acgcgcgcac caccacacaa gcaaactgga agacttctct      5220
tgtgctttta cgcaaggtca actgaaaatt aaccctaccg tgggctaaat catgtcatgt      5280
gtagtacgtt tgatttgtct gggccttgag tggtatagac tccaatagtt ctttatggcc      5340
ctctggcagt ctgtaaagga gagggtgagc cagaggggaa ggcattgcta ctggccttaa      5400
cttctttgta cgtctgatgg acgatttatt ggggaagagc cgaagagggc cagcctcagt      5460
actaacacta ctgtttctgt agtagtagga acagtgctgc gtcgatatgc atctctctct      5520
```

-continued

```
catggagatg gagagccttg gttgcgttct gtgttcttgt cctttgtgtg cgagagacag      5580
tgaggagaga gactgtacat taccgtctct cctctttttt ttttctctct ctctcctttc      5640
actgcattga gtaggtacgg cgtgtgtgct agctccttgc tgggagcaat ggaggcaaat      5700
gccacgtacc ggctcagcaa taggtatcct taactagtaa ggtgtaggag ggggatcttt      5760
ttgcactgct gaggctagaa tagacatgta tagatgctgt gtctactgac aaaagtacct      5820
ttggtacgtt gtaagctgga aaaggcaatg gggagttatg ggggaggggaa aaaaaaagag      5880 ccaggagcag tgtctgcatg catgtttttg cttgttatac gttctttcta ccctttgcat      5940
atggttgttc aattcatctt tcttttctga tcatacagcc ctgagtcggg gtattatctc      6000
aagaacagcg tcttgtgacc tcgatctcac aaagaatata ggaagtcctc catataaact      6060
acatttgtgg aaacaaaaaa ttgaaaatca tgtgtaattt agactcttac aggcgaaata      6120
tgtaaatgct aattaactaa catattctgt cgtttagcaa ggaagatgca ttgagatgaa      6180
tagccaagtt cgttaattgt ccaagcataa gttgcactcc attgccattt tttgtagaac      6240
acatgttggc gcataccata ccttggttaa tcacgctgtc actgtgatat gttagaccta      6300
ctatagccaa tgaccattat ctcaaataat gatgtgatga ctgaatgatc aggctaatta      6360
ttgcataatg cgtatactag ttccgtattg attttctgc ggttattatc ctccttcata       6420
ttcctagaga gaaagggctg aattttggcg ctcatataaa gaacataacc acatctctgt      6480
tatattactc tttgtacgta catgcaagat atgttacaca tacaaaaaag atgaggtgga      6540
tatcatgtat ctgtatagct tgaaatgctg aggtatattg atatttattg cttttgacag      6600
tttcattgac atctccatcg ctatggaaat catttcatgc actacatttc tgaagaaact      6660
ta                                                                      6662
```

```
<210> SEQ ID NO 27
<211> LENGTH: 409
<212> TYPE: PRT
<213> ORGANISM: Maize
<220> FEATURE:
<223> OTHER INFORMATION: maize wide-type species Teosinte 8759

<400> SEQUENCE: 27

Met Glu Phe Ala Ser Ser Ser Ser Arg Phe Ser Arg Glu Glu Asp Glu
1               5                   10                  15

Glu Glu Glu Gln Glu Glu Glu Glu Glu Glu Glu Glu Ala Ser Pro Arg
            20                  25                  30

Glu Ile Pro Phe Met Thr Ala Ala Ala Thr Ala Asp Thr Gly Ala Ala
        35                  40                  45

Ala Ser Ser Ser Ser Pro Ser Ala Ala Ala Ser Ser Gly Pro Ala Ala
    50                  55                  60

Ala Pro Arg Ser Ser Asp Gly Ala Gly Ala Ser Gly Ser Gly Gly Gly
65                  70                  75                  80

Gly Ser Asp Asp Val Gln Val Ile Glu Lys Glu His Met Phe Asp Lys
                85                  90                  95

Val Val Thr Pro Ser Asp Val Gly Lys Leu Asn Arg Leu Val Ile Pro
            100                 105                 110

Lys Gln His Ala Glu Lys Tyr Phe Pro Leu Asp Ala Ala Ala Asn Glu
        115                 120                 125

Lys Gly Gln Leu Leu Ser Phe Glu Asp Arg Ala Gly Lys Leu Trp Arg
    130                 135                 140

Phe Arg Tyr Ser Tyr Trp Asn Ser Ser Gln Ser Tyr Val Met Thr Lys
145                 150                 155                 160
```

-continued

```
Gly Trp Ser Arg Phe Val Lys Glu Lys Arg Leu Asp Ala Gly Asp Thr
            165                 170                 175

Val Ser Phe Cys Arg Gly Ala Gly Asp Thr Ala Arg Asp Arg Leu Phe
            180                 185                 190

Ile Asp Trp Lys Arg Arg Ala Asp Ser Arg Asp Pro His Arg Met Pro
            195                 200                 205

Arg Leu Pro Leu Pro Met Ala Pro Val Ala Ser Pro Tyr Gly Pro Trp
        210                 215                 220

Gly Gly Gly Gly Gly Gly Ala Gly Gly Phe Phe Met Pro Pro Ala
225                 230                 235                 240

Pro Pro Ala Thr Leu Tyr Glu His His Arg Phe Arg Gln Ala Leu Asp
                245                 250                 255

Phe Arg Asn Ile Asn Ala Ala Ala Ala Pro Ala Arg Gln Leu Leu Phe
            260                 265                 270

Phe Gly Ser Ala Gly Met Pro Pro Arg Ala Ser Met Pro Gln Gln Gln
        275                 280                 285

Gln Pro Pro Pro Pro Pro His Pro Pro Leu His Ser Ile Met Leu Val
    290                 295                 300

Gln Pro Ser Pro Ala Pro Pro Thr Ala Ser Val Pro Met Leu Leu Asp
305                 310                 315                 320

Ser Val Pro Leu Val Asn Ser Pro Thr Ala Ala Ser Lys Arg Val Arg
                325                 330                 335

Leu Phe Gly Val Asn Leu Asp Asn Pro Gln Pro Gly Thr Ser Ala Glu
            340                 345                 350

Ser Ser Gln Asp Ala Asn Ala Leu Ser Leu Arg Thr Pro Gly Trp Gln
        355                 360                 365

Arg Pro Gly Pro Leu Arg Phe Phe Glu Ser Pro Gln Arg Gly Ala Glu
    370                 375                 380

Ser Ser Ala Ala Ser Ser Pro Ser Ser Ser Ser Ser Lys Arg Glu
385                 390                 395                 400

Ala His Ser Ser Leu Asp Leu Asp Leu
                405
```

```
<210> SEQ ID NO 28
<211> LENGTH: 404
<212> TYPE: PRT
<213> ORGANISM: Maize

<400> SEQUENCE: 28

Met Glu Phe Ala Ser Ser Ser Ser Arg Phe Ser Lys Glu Glu Glu Glu
1                   5                   10                  15

Gln Glu Glu Glu Glu Asp Glu Glu Val Ser Pro Arg Glu Ile Pro Phe
                20                  25                  30

Met Thr Ala Ala Ala Thr Ala Gly Thr Gly Ala Thr Ser Ser Ser Pro
            35                  40                  45

Ser Pro Ser Ala Ala Ala Ser Ala Ser Ala Ser Ser Ser Ala Ala Ala
        50                  55                  60

Leu Arg Ser Ser Gly Gly Gly Gly Gly Asp Asp Asp Met Glu Val
65                  70                  75                  80

Val Glu Lys Glu His Met Phe Asp Lys Val Val Thr Pro Ser Asp Val
                85                  90                  95

Gly Lys Leu Asn Arg Leu Val Ile Pro Lys Gln His Ala Glu Lys Tyr
            100                 105                 110
```

-continued

```
Phe Pro Leu Asp Ala Ala Ala Asn Glu Lys Gly Leu Leu Leu Ser Phe
        115                 120                 125

Glu Asp Arg Ala Gly Lys Leu Trp Arg Phe Arg Tyr Ser Tyr Trp Asn
        130                 135                 140

Ser Ser Gln Ser Tyr Val Met Thr Lys Gly Trp Ser Arg Phe Val Lys
145                 150                 155                 160

Glu Lys Arg Leu Asp Ala Gly Asp Thr Val Ser Phe Cys Arg Gly Ala
                165                 170                 175

Ala Asp Ala Ala Arg Asp Arg Leu Phe Ile Asp Trp Arg Lys Arg Ser
                180                 185                 190

Ala Asp Ser Ser Arg His Pro His Arg Met Leu Pro Arg Leu Pro Leu
                195                 200                 205

His Met Pro Pro Leu Ala Ser Pro Tyr Gly Tyr Gly Pro Trp Gly Gly
        210                 215                 220

Gly Ala Gly Gly Phe Phe Val Pro Pro Ala Thr Leu Tyr Glu His His
225                 230                 235                 240

Arg Phe Arg Gln Ala Leu Asp Phe Arg Asn Val Ser Ala Ala Ala Ala
                245                 250                 255

Pro Ala Arg Gln Leu Leu Phe Phe Gly Ser Ala Gly Met Pro Pro Arg
                260                 265                 270

Ala Ser Ile Pro Gln Gln Gln Pro Pro Pro Ser Leu His Ser
                275                 280                 285

Ile Met Met Val Gln Pro Ser Pro Glu Ala Thr Ala Gly Leu Pro Met
        290                 295                 300

Leu Leu Asp Ser Val Pro Leu Val Asn Ser Pro Thr Ala Ala Ala Lys
305                 310                 315                 320

Arg Val Arg Leu Phe Gly Val Asn Leu Asp Asn Pro Gln Pro Gly Ser
                325                 330                 335

Ser Ala Glu Ser Ser His Asp Thr Asn Ala Leu Ser Leu Arg Met Pro
                340                 345                 350

Gly Trp Gln Arg Pro Gly Pro Leu Arg Phe Phe Glu Ser Thr Pro Gln
                355                 360                 365

Arg Gly Ala Ala Gly Ala Ala Ala Gly Ala Glu Ser Ser Ala Ala Ser
        370                 375                 380

Ser Pro Ser Ser Pro Ser Ser Ser Lys Arg Glu Ala His Ser Ser Val
385                 390                 395                 400

Asp Leu Asp Leu
```

```
<210> SEQ ID NO 29
<211> LENGTH: 422
<212> TYPE: PRT
<213> ORGANISM: Maize

<400> SEQUENCE: 29
```

```
Met Asp Gln Phe Ala Ala Ser Gly Arg Phe Ser Arg Glu Glu Glu Ala
1               5                   10                  15

Asp Glu Glu Gln Glu Asp Ala Ser Asn Ser Met Arg Glu Ile Ser Phe
                20                  25                  30

Met Pro Pro Ala Ala Ala Ser Ser Ser Ala Ala Ala Ser Ala Ser
        35                  40                  45

Ala Ser Ala Ser Thr Ser Ala Ser Ala Cys Ala Ser Gly Ser Ser Ser
        50                  55                  60

Ala Pro Phe Arg Ser Ala Ser Ala Ser Gly Asp Ala Ala Gly Ala Ser
65                  70                  75                  80
```

-continued

```
Gly Ser Gly Gly Pro Ala Asp Ala Asp Ala Glu Ala Glu Ala Val Glu
            85              90              95

Lys Glu His Met Phe Asp Lys Val Val Thr Pro Ser Asp Val Gly Lys
            100             105             110

Leu Asn Arg Leu Val Ile Pro Lys Gln Tyr Ala Glu Lys Tyr Phe Pro
            115             120             125

Leu Asp Ala Ala Ala Asn Glu Lys Gly Leu Leu Leu Ser Phe Glu Asp
        130             135             140

Ser Ala Gly Lys His Trp Arg Phe Arg Tyr Ser Tyr Trp Asn Ser Ser
145             150             155             160

Gln Ser Tyr Val Met Thr Lys Gly Trp Ser Arg Phe Val Lys Glu Lys
            165             170             175

Arg Leu Val Ala Gly Asp Thr Val Ser Phe Ser Arg Ala Ala Ala Glu
            180             185             190

Asp Ala Arg His Arg Leu Phe Ile Asp Trp Lys Arg Arg Val Asp Thr
            195             200             205

Arg Gly Pro Leu Arg Phe Ser Gly Leu Ala Leu Pro Met Pro Leu Pro
        210             215             220

Ser Ser His Tyr Gly Gly Pro His His Tyr Ser Pro Trp Gly Phe Gly
225             230             235             240

Gly Gly Gly Gly Gly Gly Gly Phe Phe Met Pro Pro Ser Pro Pro
            245             250             255

Ala Thr Leu Tyr Glu His Arg Leu Arg Gln Gly Leu Asp Phe Arg Ser
            260             265             270

Met Thr Thr Thr Tyr Pro Ala Pro Thr Val Gly Arg Gln Leu Leu Phe
            275             280             285

Phe Gly Ser Ala Arg Met Pro Pro His His Ala Pro Pro Pro Gln Pro
        290             295             300

Arg Pro Phe Ser Leu Pro Leu His His Tyr Thr Val Gln Pro Ser Ala
305             310             315             320

Ala Gly Val Thr Ala Ala Ser Arg Pro Val Leu Leu Asp Ser Val Pro
            325             330             335

Val Ile Glu Ser Pro Thr Thr Ala Ala Lys Arg Val Arg Leu Phe Gly
            340             345             350

Val Asn Leu Asp Asn Asn Pro Asp Gly Gly Gly Glu Ala Ser His Gln
            355             360             365

Gly Asp Ala Leu Ser Leu Gln Met Pro Gly Trp Gln Gln Arg Thr Pro
        370             375             380

Thr Leu Arg Leu Leu Glu Leu Pro Arg His Gly Gly Glu Ser Ser Ala
385             390             395             400

Ala Ser Ser Pro Ser Ser Ser Ser Ser Lys Arg Glu Ala Arg Ser
            405             410             415

Ala Leu Asp Leu Asp Leu
            420
```

```
<210> SEQ ID NO 30
<211> LENGTH: 240
<212> TYPE: PRT
<213> ORGANISM: Maize

<400> SEQUENCE: 30

Met Glu Phe Thr Thr Pro Pro Pro Ala Thr Arg Ser Gly Gly Gly Glu
1               5               10              15
```

```
Glu Arg Ala Ala Ala Glu His Asn Gln His His Gln Gln Gln His Ala
            20                  25                  30

Thr Val Glu Lys Glu His Met Phe Asp Lys Val Val Thr Pro Ser Asp
            35                  40                  45

Val Gly Lys Leu Asn Arg Leu Val Ile Pro Lys Gln His Ala Glu Lys
        50                  55                  60

Tyr Phe Pro Leu Asp Ala Ala Ala Asn Glu Lys Gly Leu Leu Leu Ser
65                  70                  75                  80

Phe Glu Asp Arg Thr Gly Lys Pro Trp Arg Phe Arg Tyr Ser Tyr Trp
                85                  90                  95

Asn Ser Ser Gln Ser Tyr Val Met Thr Lys Gly Trp Ser Arg Phe Val
            100                 105                 110

Lys Glu Lys Arg Leu Asp Ala Gly Asp Thr Val Ser Phe Gly Arg Gly
            115                 120                 125

Ile Ser Glu Ala Ala Arg Asp Arg Leu Phe Ile Asp Trp Arg Cys Arg
        130                 135                 140

Pro Asp Pro Pro Val Val His His Gln Tyr His His Arg Leu Pro Leu
145                 150                 155                 160

Pro Ser Ala Val Val Pro Tyr Ala Pro Trp Ala Ala His Ala His His
                165                 170                 175

His His Tyr Pro Ala Asp Gly His Thr Glu Pro Val Thr Pro Cys Leu
                180                 185                 190

Cys Ala Thr Leu Val Ala Thr Glu Met Arg Ala Ser Ser Ser Gln Leu
            195                 200                 205

Ser Leu Thr Arg Ser Asn Leu Ser Arg Pro Pro Gln Pro Arg Ile Ala
        210                 215                 220

Arg Val Asp Gly Ala Gln Pro Arg Pro Ser Ser Ser Pro Arg Gln Pro
225                 230                 235                 240

<210> SEQ ID NO 31
<211> LENGTH: 327
<212> TYPE: PRT
<213> ORGANISM: Maize

<400> SEQUENCE: 31

Met Glu Phe Thr Ala Pro Pro Pro Ala Thr Arg Ser Gly Gly Gly Glu
1               5                   10                  15

Glu Arg Ala Ala Ala Glu His His Gln Gln Gln Gln Gln Ala Thr Val
            20                  25                  30

Glu Lys Glu His Met Phe Asp Lys Val Val Thr Pro Ser Asp Val Gly
            35                  40                  45

Lys Leu Asn Arg Leu Val Ile Pro Lys Gln His Ala Glu Arg Tyr Phe
        50                  55                  60

Pro Leu Asp Ala Ala Ala Asn Asp Lys Gly Leu Leu Leu Ser Phe Glu
65                  70                  75                  80

Asp Arg Ala Gly Lys Pro Trp Arg Phe Arg Tyr Ser Tyr Trp Asn Ser
                85                  90                  95

Ser Gln Ser Tyr Val Met Thr Lys Gly Trp Ser Arg Phe Val Lys Glu
            100                 105                 110

Lys Arg Leu Asp Ala Gly Asp Thr Val Ser Phe Gly Arg Gly Val Gly
            115                 120                 125

Glu Ala Ala Arg Gly Arg Leu Phe Ile Asp Trp Arg Arg Arg Pro Asp
        130                 135                 140
```

-continued

```
Pro Pro Val Val His His Gln Tyr His His His Arg Leu Pro Leu Pro
145             150             155             160

Ser Ala Val Val Pro Tyr Ala Pro Trp Ala Ala Ala His Ala His
            165             170             175

His His His Tyr Pro Ala Ala Gly Val Gly Ala Ala Arg Thr Thr Thr
            180             185             190

Thr Thr Thr Thr Thr Val Leu His His Leu Pro Pro Ser Pro Ser Pro
            195             200             205

Leu Tyr Leu Asp Thr Arg Arg Arg His Val Gly Tyr Asp Ala Tyr Gly
    210             215             220

Ala Gly Thr Arg Gln Leu Leu Phe Tyr Arg Pro His Gln Gln Pro Ser
225             230             235             240

Thr Thr Val Met Leu Asp Ser Val Pro Val Arg Leu Pro Pro Thr Pro
            245             250             255

Gly Gln His Ala Glu Pro Pro Pro Ala Val Ala Ser Ser Ala Ser
            260             265             270

Lys Arg Val Arg Leu Phe Gly Val Asn Leu Asp Cys Ala Ala Ala Ala
            275             280             285

Gly Ser Glu Glu Glu Asn Val Gly Gly Trp Arg Thr Ser Ala Pro Pro
            290             295             300

Thr Gln Gln Ala Ser Ser Ser Ser Ser Tyr Ser Ser Gly Lys Ala Arg
305             310             315             320

Cys Ser Leu Asn Leu Asp Leu
            325

<210> SEQ ID NO 32
<211> LENGTH: 232
<212> TYPE: PRT
<213> ORGANISM: Maize

<400> SEQUENCE: 32

Met Glu Phe Thr Thr Pro Pro Pro Ala Thr Arg Ser Gly Gly Gly Glu
1               5               10              15

Glu Arg Ala Ala Ala Glu His Asn Gln His His Gln Gln Gln His Ala
            20              25              30

Thr Val Glu Lys Glu His Met Phe Asp Lys Val Val Thr Pro Ser Asp
            35              40              45

Val Gly Lys Leu Asn Arg Leu Val Ile Pro Lys Gln His Ala Glu Lys
    50              55              60

Tyr Phe Pro Leu Asp Ala Ala Ala Asn Glu Lys Gly Leu Leu Leu Ser
65              70              75              80

Phe Glu Asp Arg Thr Gly Lys Pro Trp Arg Tyr Arg Tyr Ser Tyr Trp
            85              90              95

Asn Ser Ser Gln Ser Tyr Val Met Thr Lys Gly Trp Ser Arg Phe Val
            100             105             110

Lys Glu Lys Arg Leu Asp Ala Gly Asp Thr Asp Ser Phe Gly Arg Gly
            115             120             125

Ile Ser Glu Ala Ala Arg Gly Arg Leu Phe Ile Asp Trp Arg Cys Arg
            130             135             140

Pro Asp Pro Pro Val Val His His Gln Tyr His His Arg Leu Pro Leu
145             150             155             160

Pro Ser Ala Val Val Pro Tyr Ala Pro Phe Leu Glu Lys Asp Val Ala
            165             170             175
```

-continued

```
Leu Asp Pro Thr Asn Arg Ser His Gly Glu Arg Pro Thr Phe Leu Glu
            180             185             190

Lys Asp Val Ala Leu Asp Ala Ala Arg Val Ala Ala Glu Gly Ala Gly
            195             200             205

Ser Asp Leu Glu Val Asp Asp Leu Asp Arg Arg Trp Glu Gly Arg
        210             215             220

Ile Ser Glu Leu Ala Ser Leu Ile
225             230

<210> SEQ ID NO 33
<211> LENGTH: 420
<212> TYPE: PRT
<213> ORGANISM: Maize

<400> SEQUENCE: 33

Met Asp Gln Phe Ala Ala Ser Arg Arg Phe Ser Arg Asn Asp Gly Ala
1               5               10              15

Asp Glu Glu Gln Glu Asp Val Ser Asn Ser Met Arg Glu Ile Ser Phe
            20              25              30

Met Pro Gly Ala Ala Ser Ser Ser Ala Ala Ala Ser Ala Ser Ala Ser
            35              40              45

Gly Ser Ser Cys Ala Pro Phe Arg Ser Ala Ser Ala Asp Gly Ala Gly
        50              55              60

Ala Ser Gly Ser Gly Gly Asp Gly Asp Gly Ser Gly Asp Val Glu Lys
65              70              75              80

Glu His Met Phe Asp Lys Val Val Thr Pro Ser Asp Val Gly Lys Leu
            85              90              95

Asn Arg Leu Val Ile Pro Lys Gln Tyr Ala Glu Lys Tyr Phe Pro Leu
            100             105             110

Asp Ala Ala Gly Asn Glu Lys Gly Leu Leu Leu Ser Phe Glu Asp Ser
            115             120             125

Asp Gly Lys His Trp Arg Phe Arg Tyr Ser Tyr Trp Asn Ser Ser Gln
        130             135             140

Ser Tyr Val Met Thr Lys Gly Trp Ser Arg Phe Val Lys Glu Lys Arg
145             150             155             160

Leu Val Ala Gly Asp Thr Val Ser Phe Ser Arg Ser Arg Ser Ala Ala
            165             170             175

Glu Val Val Asp Asp Ala Arg Arg His Arg Leu Phe Ile Asp Trp Lys
            180             185             190

Arg Arg Gly Leu Asp Thr Arg Gly Pro Leu Arg Phe Ser Gly Leu Ala
            195             200             205

Leu Pro Met Pro Leu Ala Ser Tyr Tyr Gly Ala Pro His His Tyr Ser
        210             215             220

Ser Trp Gly Leu Gly Gly Gly Gly Gly Phe Phe Met Pro Pro Ser Pro
225             230             235             240

Pro Ala Thr Leu Tyr Glu His Arg Leu Arg Gln Gly Leu Asp Phe Arg
            245             250             255

Gly Met Thr Thr Tyr Pro Ala Leu Thr Val Gly Arg Gln Leu Leu Phe
            260             265             270

Phe Gly Ser Pro Arg Met Pro Pro His His Ala Gln Pro Gln Pro Arg
            275             280             285

Pro Leu Pro Leu Pro Leu His His Tyr Thr Met Gln Pro Ser Ala Ala
        290             295             300
```

-continued

```
Gly Val Thr Ala Ala Ser Ala Ser Arg Pro Leu Val Val Asp Val Asp
305                 310                 315                 320

Ser Val Pro Ala Ile Glu Ser Pro Thr Thr Ala Ala Lys Arg Val Arg
                325                 330                 335

Leu Phe Gly Val Asn Leu Asp Asn Lys Pro Leu Ser Val Ser Asp Gly
                340                 345                 350

Gly Arg Glu Ala Ser His Gln Ser Gly Ser Gly Asn Ala Leu Leu Pro
                355                 360                 365

Leu Pro Gln Met Pro Gly Gly Trp Gln Gln Arg Thr Pro Thr Leu Arg
                370                 375                 380

Leu Leu Glu Leu Pro Arg His Gly Ala Glu Ser Ser Ala Ala Ser Ser
385                 390                 395                 400

Pro Ser Ser Ser Ser Ser Ala Lys Arg Glu Ala Arg Ser Ala Ala Leu
                405                 410                 415

Asp Leu Asp Leu
                420
```

```
<210> SEQ ID NO 34
<211> LENGTH: 420
<212> TYPE: PRT
<213> ORGANISM: Sorghum

<400> SEQUENCE: 34
```

```
Met Glu Phe Ala Ser Ser Ser Ser Arg Phe Ser Lys Glu Glu Asp Glu
1               5                   10                  15

Glu Glu Glu Gly Glu Glu Glu Asp Glu Glu Ala Ser Pro Arg Glu Ile
                20                  25                  30

Pro Phe Met Thr Ala Ala Ala Ala Thr Ala Asp Thr Gly Pro Ala Ala
                35                  40                  45

Ala Ser Ser Ser Ser Pro Ser Ala Ala Gly Ala Ser Ala Ser Ala Ser
                50              55                  60

Gly Ser Ala Ala Ala Leu Arg Ser Gly Asp Gly Ala Gly Ala Ser Gly
65                  70                  75                  80

Ser Gly Gly Gly Gly Gly Ser Asp Asp Val Glu Val Ile Glu Lys
                85                  90                  95

Glu His Met Phe Asp Lys Val Val Thr Pro Ser Asp Val Gly Lys Leu
                100                 105                 110

Asn Arg Leu Val Ile Pro Lys Gln His Ala Glu Lys Tyr Phe Pro Leu
                115                 120                 125

Asp Ala Ala Ala Asn Glu Lys Gly Leu Leu Leu Ser Phe Glu Asp Arg
                130                 135                 140

Ala Gly Lys Leu Trp Arg Phe Arg Tyr Ser Tyr Trp Asn Ser Ser Gln
145                 150                 155                 160

Ser Tyr Val Met Thr Lys Gly Trp Ser Arg Phe Val Lys Glu Lys Arg
                165                 170                 175

Leu Asp Ala Gly Asp Thr Val Ser Phe Cys Arg Gly Ala Gly Glu Ala
                180                 185                 190

Ala Arg Asp Arg Leu Phe Ile Asp Trp Lys Arg Arg Ala Asp Ser Arg
                195                 200                 205

Asp Pro His Arg Met Pro Arg Leu Pro Leu Pro Met Ala Pro Val Ala
                210                 215                 220

Ser Pro Tyr Gly Leu Gly Pro Trp Gly Gly Gly Ala Gly Gly Phe Phe
225                 230                 235                 240
```

-continued

```
Met Pro Pro Ala Pro Pro Ala Thr Leu Tyr Glu His His Arg Phe Arg
                245                 250                 255

Gln Ala Leu Asp Phe Arg Asn Ile Asn Ala Ala Ala Ala Pro Ala Arg
                260                 265                 270

Gln Leu Leu Phe Phe Gly Ser Gln Gly Met Pro Pro Arg Ala Ser Met
                275                 280                 285

Pro Leu Gln Gln Gln Gln Pro Gln Pro Gln Pro Ser Leu Pro Pro Pro
                290                 295                 300

Pro Pro Pro Leu His Ser Ile Met Met Val Gln Pro Gly Ser Pro Ala
305                 310                 315                 320

Val Thr His Gly Leu Pro Met Val Leu Asp Ser Val Pro Leu Val Asn
                325                 330                 335

Ser Pro Thr Ala Ala Ala Lys Arg Val Arg Leu Phe Gly Val Asn Leu
                340                 345                 350

Asp Asn Pro Gln Gln Gly Ser Ser Ala Glu Ser Ser Gln Asp Ala Asn
                355                 360                 365

Ala Leu Ser Leu Arg Met Pro Gly Trp Gln Arg Pro Gly Pro Leu Arg
                370                 375                 380

Phe Phe Glu Ser Pro Gln Arg Gly Ala Ala Glu Ser Ser Ala Ala Ser
385                 390                 395                 400

Ser Pro Ser Ser Ser Ser Ser Lys Arg Glu Ala His Ser Ser Leu
                405                 410                 415

Asp Leu Asp Leu
            420

<210> SEQ ID NO 35
<211> LENGTH: 434
<212> TYPE: PRT
<213> ORGANISM: Sorghum

<400> SEQUENCE: 35

Met Asp Gln Phe Ala Ala Ser Gly Arg Phe Ser Arg Glu Glu Glu Ala
1                   5                   10                  15

Asp Glu Glu Gln Glu Asp Ala Ser Asn Ser Met Arg Glu Ile Ser Phe
                20                  25                  30

Met Pro Ala Ala Ala Ala Ala Gly Thr Ala Pro Ser Ser Ser Ala Ala
            35                  40                  45

Ala Ser Ala Ala Ser Thr Ser Ala Ser Ala Ser Ala Ala Ser Gly Ser
    50                  55                  60

Ser Ser Ala Ala Ala Pro Phe Arg Ser Ala Ser Gly Asp Ala Ala Gly
65                  70                  75                  80

Ala Ser Gly Ser Gly Gly Gly Gly Ala Ala Ala Asp Val Glu Ala
                85                  90                  95

Val Glu Lys Glu His Met Phe Asp Lys Val Val Thr Pro Ser Asp Val
                100                 105                 110

Gly Lys Leu Asn Arg Leu Val Ile Pro Lys Gln Tyr Ala Glu Lys Tyr
                115                 120                 125

Phe Pro Leu Asp Ala Ala Ala Asn Glu Lys Gly Leu Leu Leu Ser Phe
            130                 135                 140

Glu Asp Ser Ala Gly Lys His Trp Arg Phe Arg Tyr Ser Tyr Trp Asn
145                 150                 155                 160

Ser Ser Gln Ser Tyr Val Met Thr Lys Gly Trp Ser Arg Phe Val Lys
                165                 170                 175
```

-continued

```
Glu Lys Arg Leu Val Ala Gly Asp Thr Val Ser Phe Ser Arg Ala Ala
            180                 185                 190

Ala Glu Asp Ala Arg His Arg Leu Phe Ile Asp Trp Lys Arg Arg Val
            195                 200                 205

Asp Thr Arg Gly Pro Leu Arg Phe Ser Gly Leu Ala Leu Pro Met Pro
            210                 215                 220

Leu Ala Ser His Tyr Gly Pro His His Tyr Ser Pro Trp Gly Phe Gly
225                 230                 235                 240

Ile Gly Gly Val Gly Gly Gly Gly Gly Gly Phe Phe Met Pro
                245                 250                 255

Pro Ser Pro Pro Ala Thr Leu Tyr Glu His Arg Leu Arg Gln Gly Leu
            260                 265                 270

Asp Phe Arg Ser Met Thr Asn Tyr Pro Ala Pro Thr Val Gly Arg Gln
            275                 280                 285

Gln Leu Leu Phe Phe Gly Ser Ala Arg Met Pro Pro His His Ala Pro
            290                 295                 300

Ala Pro Gln Pro Arg Pro Leu Ser Leu Pro Leu His His Phe Thr Val
305                 310                 315                 320

Gln Pro Ser Ala Ala Ala Gly Val Thr Ala Ala Ser Arg Pro Val Val
                325                 330                 335

Leu Asp Ser Val Pro Val Ile Glu Ser Pro Thr Thr Ala Ala Lys Arg
                340                 345                 350

Val Arg Leu Phe Gly Val Asn Leu Asp Asn Asn Pro Leu Ser Glu Pro
                355                 360                 365

Asp Gly Gly Val Gly Glu Ala Ser His Gln Gly Asn Ala Leu Ser Leu
            370                 375                 380

Gln Met Pro Gly Trp Gln Gln Arg Thr Thr Pro Thr Leu Arg Leu Leu
385                 390                 395                 400

Glu Leu Pro Arg His Gly Ala Ala Glu Ser Ser Ala Ala Ser Ser Pro
                405                 410                 415

Ser Ser Ser Ser Ser Ser Lys Arg Glu Ala Arg Ser Ala Leu Asp Leu
                420                 425                 430

Asp Leu

<210> SEQ ID NO 36
<211> LENGTH: 330
<212> TYPE: PRT
<213> ORGANISM: Sorghum

<400> SEQUENCE: 36

Met Glu Phe Thr Ala Pro Pro Thr Ala Ala Arg Ser Gly Gly Gly Glu
1               5                   10                  15

Glu Arg Ala Ala Glu His Gln Gln Gln Gln Gln Gln Leu Ala Ala
            20                  25                  30

Val Glu Lys Glu His Met Phe Asp Lys Val Val Thr Pro Ser Asp Val
        35                  40                  45

Gly Lys Leu Asn Arg Leu Val Ile Pro Lys Gln His Ala Glu Lys Tyr
        50                  55                  60

Phe Pro Leu Asp Ala Ala Ala Asn Glu Lys Gly Leu Leu Leu Ser Phe
65                  70                  75                  80

Glu Asp Arg Thr Gly Lys Pro Trp Arg Phe Arg Tyr Ser Tyr Trp Asn
                85                  90                  95

Ser Ser Gln Ser Tyr Val Met Thr Lys Gly Trp Ser Arg Phe Val Lys
            100                 105                 110
```

```
Glu Lys Arg Leu Asp Ala Gly Asp Thr Val Ser Phe Gly Arg Gly Val
        115                 120                 125

Gly Asp Ala Ala Arg Gly Arg Leu Phe Ile Asp Trp Arg Arg Arg Pro
    130                 135                 140

Asp Pro Pro Val His His Gln Tyr His His Arg Leu Pro Leu Pro Ser
145                 150                 155                 160

Val Val Pro Tyr Ala Pro Trp Pro His Ala His His His His Tyr Pro
                165                 170                 175

Ala Ala Ala Ala Ala Val Gly Val Gly Val Gly Ala Gly Ala Gly Ala
                180                 185                 190

Ala Arg Thr Thr Thr Val Leu His Leu Pro Pro Ser Pro Ser Ser Leu
        195                 200                 205

Tyr Asp Pro His Leu Arg His Val Gly Tyr Asp Ala Tyr Gly Ala Gly
    210                 215                 220

Thr Arg Gln Leu Leu Phe Tyr Arg Pro Leu His His Gln Gln Pro Ser
225                 230                 235                 240

Thr Ala Val Val Leu Asp Ser Val Pro Val Arg Leu Pro Thr Thr Pro
                245                 250                 255

Gly Gln His Ala Glu Pro Pro Ala Pro Val Val Ala Ser Ser Ala Ser
        260                 265                 270

Lys Arg Val Arg Leu Phe Gly Val Asn Leu Asp Cys Ala Gly Ser Glu
        275                 280                 285

Glu Glu Asn Gly Gly Gly Gly Trp Arg Thr Ser Ala Pro Pro Thr
    290                 295                 300

Pro His Gly Leu Pro Ser Pro Pro Ser Ser Ser Ser Ser Ser Ser Gly
305                 310                 315                 320

Lys Ala Arg Cys Ser Leu Asn Leu Asp Leu
        325                 330
```

```
<210> SEQ ID NO 37
<211> LENGTH: 330
<212> TYPE: PRT
<213> ORGANISM: Sorghum

<400> SEQUENCE: 37
```

```
Met Glu Phe Thr Ala Pro Pro Thr Ala Ala Arg Ser Gly Gly Gly Glu
1               5                   10                  15

Glu Arg Ala Ala Glu His Gln Gln Gln Gln Gln Gln Leu Ala Ala
        20                  25                  30

Val Glu Lys Glu His Met Phe Asp Lys Val Val Thr Pro Ser Asp Val
        35                  40                  45

Gly Lys Leu Asn Arg Leu Val Ile Pro Lys Gln His Ala Glu Lys Tyr
    50                  55                  60

Phe Pro Leu Asp Ala Ala Ala Asn Glu Lys Gly Leu Leu Leu Ser Phe
65                  70                  75                  80

Glu Asp Arg Thr Gly Lys Pro Trp Arg Phe Arg Tyr Ser Tyr Trp Asn
                85                  90                  95

Ser Ser Gln Ser Tyr Val Met Thr Lys Gly Trp Ser Arg Phe Val Lys
            100                 105                 110

Glu Lys Arg Leu Asp Ala Gly Asp Thr Val Ser Phe Gly Arg Gly Val
        115                 120                 125

Gly Asp Ala Ala Arg Gly Arg Leu Phe Ile Asp Trp Arg Arg Arg Pro
    130                 135                 140
```

-continued

```
Asp Pro Pro Val His His Gln Tyr His His Arg Leu Pro Leu Pro Ser
145             150             155             160

Val Val Pro Tyr Ala Pro Trp Pro His Ala His His His His Tyr Pro
                165             170             175

Ala Ala Ala Ala Ala Val Gly Val Gly Val Gly Ala Gly Ala Gly Ala
            180             185             190

Ala Arg Thr Thr Thr Val Leu His Leu Pro Pro Ser Pro Ser Ser Leu
            195             200             205

Tyr Asp Pro His Leu Arg His Val Gly Tyr Asp Ala Tyr Gly Ala Gly
        210             215             220

Thr Arg Gln Leu Leu Phe Tyr Arg Pro Leu His His Gln Gln Pro Ser
225             230             235             240

Thr Ala Val Val Leu Asp Ser Val Pro Val Arg Leu Pro Thr Thr Pro
                245             250             255

Gly Gln His Ala Glu Pro Pro Ala Pro Val Val Ala Ser Ser Ala Ser
            260             265             270

Lys Arg Val Arg Leu Phe Gly Val Asn Leu Asp Cys Ala Gly Ser Glu
            275             280             285

Glu Glu Asn Gly Gly Gly Gly Trp Arg Thr Ser Ala Pro Pro Thr
        290             295             300

Pro His Gly Leu Pro Ser Pro Pro Ser Ser Ser Ser Ser Ser Ser Gly
305             310             315             320

Lys Ala Arg Cys Ser Leu Asn Leu Asp Leu
                325             330
```

```
<210> SEQ ID NO 38
<211> LENGTH: 412
<212> TYPE: PRT
<213> ORGANISM: Oryza
<220> FEATURE:
<223> OTHER INFORMATION: Rice

<400> SEQUENCE: 38

Met Glu Phe Thr Thr Ser Ser Arg Phe Ser Lys Glu Glu Glu Asp Glu
1               5               10              15

Glu Gln Asp Glu Ala Gly Arg Arg Glu Ile Pro Phe Met Thr Ala Thr
            20              25              30

Ala Glu Ala Ala Pro Ala Pro Thr Ser Ser Ser Ser Ser Pro Ala His
            35              40              45

His Ala Ala Ser Ala Ser Ala Ser Ala Ser Ala Ser Gly Ser Ser Thr
        50              55              60

Pro Phe Arg Ser Asp Asp Gly Ala Gly Ala Ser Gly Ser Gly Gly Gly
65              70              75              80

Gly Gly Gly Gly Gly Glu Ala Glu Val Val Glu Lys Glu His Met Phe
            85              90              95

Asp Lys Val Val Thr Pro Ser Asp Val Gly Lys Leu Asn Arg Leu Val
            100             105             110

Ile Pro Lys Gln Tyr Ala Glu Lys Tyr Phe Pro Leu Asp Ala Ala Ala
        115             120             125

Asn Glu Lys Gly Leu Leu Leu Asn Phe Glu Asp Arg Ala Gly Lys Pro
        130             135             140

Trp Arg Phe Arg Tyr Ser Tyr Trp Asn Ser Ser Gln Ser Tyr Val Met
145             150             155             160

Thr Lys Gly Trp Ser Arg Phe Val Lys Glu Lys Arg Leu Asp Ala Gly
                165             170             175
```

-continued

```
Asp Thr Val Ser Phe Ser Arg Gly Ile Gly Asp Glu Ala Ala Arg His
        180                 185                 190

Arg Leu Phe Ile Asp Trp Lys Arg Arg Ala Asp Thr Arg Asp Pro Leu
        195                 200                 205

Arg Leu Pro Arg Gly Leu Pro Leu Pro Met Pro Leu Thr Ser His Tyr
        210                 215                 220

Ala Pro Trp Gly Ile Gly Gly Gly Gly Phe Phe Val Gln Pro Ser
225                 230                 235                 240

Pro Pro Ala Thr Leu Tyr Glu His Arg Leu Arg Gln Gly Leu Asp Phe
                245                 250                 255

Arg Ala Phe Asn Pro Ala Ala Ala Met Gly Arg Gln Val Leu Leu Phe
                260                 265                 270

Gly Ser Ala Arg Ile Pro Pro Gln Ala Pro Leu Leu Ala Arg Ala Pro
        275                 280                 285

Ser Pro Leu His His His Tyr Thr Leu Gln Pro Ser Gly Asp Gly Val
        290                 295                 300

Arg Ala Ala Gly Ser Pro Val Val Leu Asp Ser Val Pro Val Ile Glu
305                 310                 315                 320

Ser Pro Thr Thr Ala Ala Lys Arg Val Arg Leu Phe Gly Val Asn Leu
                325                 330                 335

Asp Asn Pro His Ala Gly Gly Gly Gly Ala Ala Ala Gly Glu Ser
                340                 345                 350

Ser Asn His Gly Asn Ala Leu Ser Leu Gln Thr Pro Ala Trp Met Arg
        355                 360                 365

Arg Asp Pro Thr Leu Arg Leu Leu Glu Leu Pro Pro His His His His
        370                 375                 380

Gly Ala Glu Ser Ser Ala Ala Ser Ser Pro Ser Ser Ser Ser Ser Ser
385                 390                 395                 400

Lys Arg Asp Ala His Ser Ala Leu Asp Leu Asp Leu
                405                 410
```

```
<210> SEQ ID NO 39
<211> LENGTH: 293
<212> TYPE: PRT
<213> ORGANISM: Oryza
<220> FEATURE:
<223> OTHER INFORMATION: Rice

<400> SEQUENCE: 39

Met Glu Gln Glu Gln Asp Glu Glu Glu Glu Ala Glu Ala Ser Pro
1               5                   10                  15

Arg Glu Ile Pro Phe Met Thr Ser Ala Ala Ala Ala Thr Ala Ser
                20                  25                  30

Ser Ser Ser Pro Thr Ser Val Ser Pro Ser Ala Thr Ala Ser Ala Ala
        35                  40                  45

Ala Ser Thr Ser Ala Ser Gly Ser Pro Phe Arg Ser Ser Asp Gly Ala
        50                  55                  60

Gly Ala Ser Gly Ser Gly Gly Gly Gly Gly Glu Asp Val Glu Val
65                  70                  75                  80

Ile Glu Lys Glu His Met Phe Asp Lys Val Val Thr Pro Ser Asp Val
                85                  90                  95

Gly Lys Leu Asn Arg Leu Val Ile Pro Lys Gln His Ala Glu Lys Tyr
                100                 105                 110

Phe Pro Leu Asp Ser Ala Ala Asn Glu Lys Gly Leu Leu Leu Ser Phe
        115                 120                 125
```

-continued

```
Glu Asp Arg Thr Gly Lys Leu Trp Arg Phe Arg Tyr Ser Tyr Trp Asn
    130             135             140

Ser Ser Gln Ser Tyr Val Met Thr Lys Gly Trp Ser Arg Phe Val Lys
145             150             155             160

Glu Lys Arg Leu Asp Ala Gly Asp Thr Val Ser Phe Cys Arg Gly Ala
            165             170             175

Ala Glu Ala Thr Arg Asp Arg Leu Phe Ile Asp Trp Lys Arg Arg Ala
            180             185             190

Asp Val Arg Asp Pro His Arg Phe Gln Arg Leu Pro Leu Pro Met Thr
            195             200             205

Ser Pro Tyr Gly Pro Trp Gly Gly Gly Ala Gly Ala Ser Ser Cys Arg
    210             215             220

Pro Arg Arg Pro Pro Arg Ser Thr Ser Ile Thr Ala Phe Ala Arg Ala
225             230             235             240

Ser Thr Ser Ala Thr Ser Thr Pro Leu Cys Arg Arg Gly Ser Ser Ser
            245             250             255

Ser Ser Ala Pro Gln Gly Arg Gly Phe Ile Ser Thr Arg Pro Cys His
            260             265             270

Arg Arg Arg Arg His Leu Arg Leu Leu Thr Asn Ser Thr Leu Arg Cys
            275             280             285

Thr Thr Arg Ala Pro
    290
```

```
<210> SEQ ID NO 40
<211> LENGTH: 311
<212> TYPE: PRT
<213> ORGANISM: Oryza
<220> FEATURE:
<223> OTHER INFORMATION: Rice

<400> SEQUENCE: 40
```

```
Met Glu Phe Ile Thr Pro Ile Val Arg Pro Ala Ser Ala Ala Ala Gly
1               5               10              15

Gly Gly Glu Val Gln Glu Ser Gly Gly Arg Ser Leu Ala Ala Val Glu
            20              25              30

Lys Glu His Met Phe Asp Lys Val Val Thr Pro Ser Asp Val Gly Lys
            35              40              45

Leu Asn Arg Leu Val Ile Pro Lys Gln His Ala Glu Lys Tyr Phe Pro
    50              55              60

Leu Asp Ala Ala Ser Asn Glu Lys Gly Leu Leu Leu Ser Phe Glu Asp
65              70              75              80

Arg Thr Gly Lys Pro Trp Arg Phe Arg Tyr Ser Tyr Trp Asn Ser Ser
            85              90              95

Gln Ser Tyr Val Met Thr Lys Gly Trp Ser Arg Phe Val Lys Glu Lys
            100             105             110

Arg Leu Asp Ala Gly Asp Thr Val Ser Phe Gly Arg Gly Val Gly Glu
            115             120             125

Ala Ala Arg Gly Arg Leu Phe Ile Asp Trp Arg Arg Arg Pro Asp Val
    130             135             140

Val Ala Ala Leu Gln Pro Pro Thr His Arg Phe Ala His His Leu Pro
145             150             155             160

Ser Ser Ile Pro Phe Ala Pro Trp Ala His His His Gly His Gly Ala
            165             170             175

Ala Ala Ala Ala Ala Ala Ala Ala Gly Ala Arg Phe Leu Leu Pro Pro
            180             185             190
```

```
Ser Ser Thr Pro Ile Tyr Asp His His Arg Arg His Ala His Ala Val
        195                 200                 205

Gly Tyr Asp Ala Tyr Ala Ala Ala Thr Ser Arg Gln Val Leu Phe Tyr
    210                 215                 220

Arg Pro Leu Pro Pro Gln Gln Gln His His Pro Ala Val Val Leu Glu
225                 230                 235                 240

Ser Val Pro Val Arg Met Thr Ala Gly His Ala Glu Pro Pro Ser Ala
                245                 250                 255

Pro Ser Lys Arg Val Arg Leu Phe Gly Val Asn Leu Asp Cys Ala Asn
            260                 265                 270

Ser Glu Gln Asp His Ala Gly Val Val Gly Lys Thr Ala Pro Pro Pro
        275                 280                 285

Leu Pro Ser Pro Pro Ser Ser Ser Ser Ser Ser Ser Gly Lys Ala Arg
    290                 295                 300

Cys Ser Leu Asn Leu Asp Leu
305                 310

<210> SEQ ID NO 41
<211> LENGTH: 335
<212> TYPE: PRT
<213> ORGANISM: Arabidopsis

<400> SEQUENCE: 41

Met Asp Leu Ser Leu Ala Pro Thr Thr Thr Thr Ser Ser Asp Gln Glu
1               5                   10                  15

Gln Asp Arg Asp Gln Glu Leu Thr Ser Asn Ile Gly Ala Ser Ser Ser
            20                  25                  30

Ser Gly Pro Ser Gly Asn Asn Asn Asn Leu Pro Met Met Met Ile Pro
        35                  40                  45

Pro Pro Glu Lys Glu His Met Phe Asp Lys Val Val Thr Pro Ser Asp
    50                  55                  60

Val Gly Lys Leu Asn Arg Leu Val Ile Pro Lys Gln His Ala Glu Arg
65                  70                  75                  80

Tyr Phe Pro Leu Asp Ser Ser Asn Asn Gln Asn Gly Thr Leu Leu Asn
                85                  90                  95

Phe Gln Asp Arg Asn Gly Lys Met Trp Arg Phe Arg Tyr Ser Tyr Trp
            100                 105                 110

Asn Ser Ser Gln Ser Tyr Val Met Thr Lys Gly Trp Ser Arg Phe Val
        115                 120                 125

Lys Glu Lys Lys Leu Asp Ala Gly Asp Ile Val Ser Phe Gln Arg Gly
    130                 135                 140

Ile Gly Asp Glu Ser Glu Arg Ser Lys Leu Tyr Ile Asp Trp Arg His
145                 150                 155                 160

Arg Pro Asp Met Ser Leu Val Gln Ala His Gln Phe Glu Tyr Asn Ser
                165                 170                 175

Val Pro Ile His Arg Gly Leu Asn Ile Gly Asn His Gln Arg Ser Tyr
            180                 185                 190

Tyr Asn Thr Gln Arg Gln Glu Phe Val Gly Tyr Gly Tyr Gly Asn Leu
        195                 200                 205

Ala Gly Arg Cys Tyr Tyr Thr Gly Ser Pro Leu Asp His Arg Asn Ile
    210                 215                 220

Val Gly Ser Glu Pro Leu Val Ile Asp Ser Val Pro Val Val Pro Gly
225                 230                 235                 240
```

-continued

```
Arg Leu Thr Pro Val Met Leu Pro Pro Leu Pro Pro Pro Ser Thr
            245             250             255

Ala Gly Lys Arg Leu Arg Leu Phe Gly Val Asn Met Glu Cys Gly Asn
            260             265             270

Asp Tyr Asn Gln Gln Glu Glu Ser Trp Leu Val Pro Arg Gly Glu Ile
            275             280             285

Gly Ala Ser Ser Ser Ser Ser Ser Ala Leu Arg Leu Asn Leu Ser Thr
            290             295             300

Asp His Asp Asp Asp Asn Asp Asp Gly Asp Asp Gly Asp Asp Asp Gln
305             310             315             320

Phe Ala Lys Lys Gly Lys Ser Ser Leu Ser Leu Asn Phe Asn Pro
            325             330             335

<210> SEQ ID NO 42
<211> LENGTH: 310
<212> TYPE: PRT
<213> ORGANISM: Arabidopsis

<400> SEQUENCE: 42

Met Met Thr Asp Leu Ser Leu Thr Arg Asp Glu Asp Glu Glu Glu Ala
1               5               10              15

Lys Pro Leu Ala Glu Glu Glu Gly Ala Arg Glu Val Ala Asp Arg Glu
            20              25              30

His Met Phe Asp Lys Val Val Thr Pro Ser Asp Val Gly Lys Leu Asn
            35              40              45

Arg Leu Val Ile Pro Lys Gln His Ala Glu Arg Phe Phe Pro Leu Asp
            50              55              60

Ser Ser Ser Asn Glu Lys Gly Leu Leu Leu Asn Phe Glu Asp Leu Thr
65              70              75              80

Gly Lys Ser Trp Arg Phe Arg Tyr Ser Tyr Trp Asn Ser Ser Gln Ser
            85              90              95

Tyr Val Met Thr Lys Gly Trp Ser Arg Phe Val Lys Asp Lys Lys Leu
            100             105             110

Asp Ala Gly Asp Ile Val Ser Phe Gln Arg Cys Val Gly Asp Ser Gly
            115             120             125

Arg Asp Ser Arg Leu Phe Ile Asp Trp Arg Arg Arg Pro Lys Val Pro
            130             135             140

Asp His Pro His Phe Ala Ala Gly Ala Met Phe Pro Arg Phe Tyr Ser
145             150             155             160

Phe Pro Ser Thr Asn Tyr Ser Leu Tyr Asn His Gln Gln Gln Arg His
            165             170             175

His His Ser Gly Gly Gly Tyr Asn Tyr His Gln Ile Pro Arg Glu Phe
            180             185             190

Gly Tyr Gly Tyr Phe Val Arg Ser Val Asp Gln Arg Asn Asn Pro Ala
            195             200             205

Ala Ala Val Ala Asp Pro Leu Val Ile Glu Ser Val Pro Val Met Met
            210             215             220

His Gly Arg Ala Asn Gln Glu Leu Val Gly Thr Ala Gly Lys Arg Leu
225             230             235             240

Arg Leu Phe Gly Val Asp Met Glu Cys Gly Glu Ser Gly Met Thr Asn
            245             250             255

Ser Thr Glu Glu Glu Ser Ser Ser Ser Gly Gly Ser Leu Pro Arg Gly
            260             265             270
```

-continued

Gly Gly Gly Gly Ala Ser Ser Ser Ser Phe Phe Gln Leu Arg Leu Gly
        275                 280                 285

Ser Ser Ser Glu Asp Asp His Phe Thr Lys Lys Gly Lys Ser Ser Leu
    290                 295                 300

Ser Phe Asp Leu Asp Gln
305                 310

<210> SEQ ID NO 43
<211> LENGTH: 358
<212> TYPE: PRT
<213> ORGANISM: Arabidopsis

<400> SEQUENCE: 43

Met Asp Leu Ser Leu Ala Pro Thr Thr Thr Thr Ser Ser Asp Gln Glu
1               5                   10                  15

Gln Asp Arg Asp Gln Glu Leu Thr Ser Asn Ile Gly Ala Ser Ser Ser
            20                  25                  30

Ser Gly Pro Ser Gly Asn Asn Asn Asn Leu Pro Met Met Met Ile Pro
        35                  40                  45

Pro Pro Glu Lys Glu His Met Phe Asp Lys Val Val Thr Pro Ser Asp
    50                  55                  60

Val Gly Lys Leu Asn Arg Leu Val Ile Pro Lys Gln His Ala Glu Arg
65                  70                  75                  80

Tyr Phe Pro Leu Asp Ser Ser Asn Asn Gln Asn Gly Thr Leu Leu Asn
                85                  90                  95

Phe Gln Asp Arg Asn Gly Lys Met Trp Arg Phe Arg Tyr Ser Tyr Trp
            100                 105                 110

Asn Ser Ser Gln Ser Tyr Val Met Thr Lys Gly Trp Ser Arg Phe Val
        115                 120                 125

Lys Glu Lys Lys Leu Asp Ala Gly Asp Ile Val Ser Phe Gln Arg Gly
    130                 135                 140

Ile Gly Asp Glu Ser Glu Arg Ser Lys Leu Tyr Ile Asp Trp Arg His
145                 150                 155                 160

Arg Pro Asp Met Ser Leu Val Gln Ala His Gln Phe Gly Asn Phe Gly
                165                 170                 175

Phe Asn Phe Asn Phe Pro Thr Thr Ser Gln Tyr Ser Asn Arg Phe His
            180                 185                 190

Pro Leu Pro Glu Tyr Asn Ser Val Pro Ile His Arg Gly Leu Asn Ile
        195                 200                 205

Gly Asn His Gln Arg Ser Tyr Tyr Asn Thr Gln Arg Gln Glu Phe Val
    210                 215                 220

Gly Tyr Gly Tyr Gly Asn Leu Ala Gly Arg Cys Tyr Tyr Thr Gly Ser
225                 230                 235                 240

Pro Leu Asp His Arg Asn Ile Val Gly Ser Glu Pro Leu Val Ile Asp
                245                 250                 255

Ser Val Pro Val Val Pro Gly Arg Leu Thr Pro Val Met Leu Pro Pro
            260                 265                 270

Leu Pro Pro Pro Pro Ser Thr Ala Gly Lys Arg Leu Arg Leu Phe Gly
        275                 280                 285

Val Asn Met Glu Cys Gly Asn Asp Tyr Asn Gln Gln Glu Glu Ser Trp
    290                 295                 300

Leu Val Pro Arg Gly Glu Ile Gly Ala Ser Ser Ser Ser Ser Ser Ala
305                 310                 315                 320

Leu Arg Leu Asn Leu Ser Thr Asp His Asp Asp Asp Asn Asp Asp Gly
            325               330               335

Asp Asp Gly Asp Asp Asp Gln Phe Ala Lys Lys Gly Lys Ser Ser Leu
            340               345               350

Ser Leu Asn Phe Asn Pro
        355

<210> SEQ ID NO 44
<211> LENGTH: 344
<212> TYPE: PRT
<213> ORGANISM: Arabidopsis

<400> SEQUENCE: 44

Met Glu Ser Ser Ser Val Asp Glu Ser Thr Thr Ser Thr Gly Ser Ile
1               5               10              15

Cys Glu Thr Pro Ala Ile Thr Pro Ala Lys Lys Ser Ser Val Gly Asn
            20              25              30

Leu Tyr Arg Met Gly Ser Gly Ser Ser Val Val Leu Asp Ser Glu Asn
        35              40              45

Gly Val Glu Ala Glu Ser Arg Lys Leu Pro Ser Ser Lys Tyr Lys Gly
    50              55              60

Val Val Pro Gln Pro Asn Gly Arg Trp Gly Ala Gln Ile Tyr Glu Lys
65              70              75              80

His Gln Arg Val Trp Leu Gly Thr Phe Asn Glu Glu Asp Glu Ala Ala
            85              90              95

Arg Ala Tyr Asp Val Ala Val His Arg Phe Arg Arg Arg Asp Ala Val
            100             105             110

Thr Asn Phe Lys Asp Val Lys Met Asp Glu Asp Glu Val Asp Phe Leu
            115             120             125

Asn Ser His Ser Lys Ser Glu Ile Val Asp Met Leu Arg Lys His Thr
        130             135             140

Tyr Asn Glu Glu Leu Glu Gln Ser Lys Arg Arg Arg Asn Gly Asn Gly
145             150             155             160

Asn Met Thr Arg Thr Leu Leu Thr Ser Gly Leu Ser Asn Asp Gly Val
            165             170             175

Ser Thr Thr Gly Phe Arg Ser Ala Glu Ala Leu Phe Glu Lys Ala Val
            180             185             190

Thr Pro Ser Asp Val Gly Lys Leu Asn Arg Leu Val Ile Pro Lys His
            195             200             205

His Ala Glu Lys His Phe Pro Leu Pro Ser Ser Asn Val Ser Val Lys
        210             215             220

Gly Val Leu Leu Asn Phe Glu Asp Val Asn Gly Lys Val Trp Arg Phe
225             230             235             240

Arg Tyr Ser Tyr Trp Asn Ser Ser Gln Ser Tyr Val Leu Thr Lys Gly
            245             250             255

Trp Ser Arg Phe Val Lys Glu Lys Asn Leu Arg Ala Gly Asp Val Val
            260             265             270

Ser Phe Ser Arg Ser Asn Gly Gln Asp Gln Gln Leu Tyr Ile Gly Trp
        275             280             285

Lys Ser Arg Ser Gly Ser Asp Leu Asp Ala Gly Arg Val Leu Arg Leu
        290             295             300

Phe Gly Val Asn Ile Ser Pro Glu Ser Ser Arg Asn Asp Val Val Gly
305             310             315             320

```
Asn Lys Arg Val Asn Asp Thr Glu Met Leu Ser Leu Val Cys Ser Lys
            325                 330                 335

Lys Gln Arg Ile Phe His Ala Ser
            340

<210> SEQ ID NO 45
<211> LENGTH: 231
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 45
ggacgaggag gaagagcagg aggaagagga ggaggaggag gaggcgtctc cgcgcgagat      60 cccctttcatg acagcggcag cgacggccga caccggagcc gccgcctcct cgtcctcgcc    120
ttccgcggcg gcctcatcgg gtcctgctgc tgcccccccgc tcgagcgacg gcgccggggc    180
gtccgggagc ggcggcggcg ggagcgacga cgtgcaggtg atcgagaagg a             231

<210> SEQ ID NO 46
<211> LENGTH: 32
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 46
cgggatcccc atggggacga ggaggaagag ca                                    32

<210> SEQ ID NO 47
<211> LENGTH: 28
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 47
ggactagttc cttctcgatc acctgcac                                         28

<210> SEQ ID NO 48
<211> LENGTH: 33
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 48
gaagatctgg ttaccggacg aggaggaaga gca                                   33

<210> SEQ ID NO 49
<211> LENGTH: 28
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 49
gctctagatc cttctcgatc acctgcac                                         28
```

-continued

```
<210> SEQ ID NO 50
<211> LENGTH: 19
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 50
ggcctcatcg cggatagat                                                       19

<210> SEQ ID NO 51
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 51
ttcgccagct gatcgatctc                                                      20

<210> SEQ ID NO 52
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 52
atggagttcg cgagctcttc                                                      20

<210> SEQ ID NO 53
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 53
tcacagatcg agatccaagg                                                      20

<210> SEQ ID NO 54
<211> LENGTH: 19
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 54
ctcttcgagt aggttttcc                                                       19

<210> SEQ ID NO 55
<211> LENGTH: 4
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 55 ggcg                                                                        4

<210> SEQ ID NO 56
```

```
<211> LENGTH: 4
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 56 aaac                                                                               4

<210> SEQ ID NO 57
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 57
gctcttcgag taggttttcc                                                              20

<210> SEQ ID NO 58
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 58
ggaaaaccta ctcgaagagc                                                              20

<210> SEQ ID NO 59
<211> LENGTH: 25
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 59
ttagtcccac ctcgccagtt tacag                                                        25

<210> SEQ ID NO 60
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 60
cagccagcta gtcagtctcc                                                              20

<210> SEQ ID NO 61
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 61
tgtcatgaag gggatctcgc                                                              20

<210> SEQ ID NO 62
<211> LENGTH: 48
```

<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 62
aactgcgcat gcgcgcgctg agtggtcctt ctcttttaat tactactg                    48

<210> SEQ ID NO 63
<211> LENGTH: 48
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 63
cagtagtaat taaaagagaa ggaccactca gcgcgcgcat gcgcagtt                     48

<210> SEQ ID NO 64
<211> LENGTH: 48
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 64
aactgcgcat gcgcgcgctg agtggtcctt ctcttttaat tactactg                    48

<210> SEQ ID NO 65
<211> LENGTH: 48
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 65
cagtagtaat taaaagagaa ggaccactca gcgcgcgcat gcgcagtt                     48

<210> SEQ ID NO 66
<211> LENGTH: 50
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 66
aactgcgcat gcgcgcgctg agtgtggtcc ttctctttta attactactg                  50

<210> SEQ ID NO 67
<211> LENGTH: 50
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 67
cagtagtaat taaaagagaa ggaccacact cagcgcgcgc atgcgcagtt                   50

<210> SEQ ID NO 68
<211> LENGTH: 50
<212> TYPE: DNA

-continued

<213> ORGANISM: artificial sequence
<220> FEATURE:
<223> OTHER INFORMATION: Description of Artificial Sequence: Synthetic
      oligonucleotide

<400> SEQUENCE: 68
aactgcgcat gcgcgcgctg agtgtggtcc ttctcttta attactactg                50

<210> SEQ ID NO 69
<211> LENGTH: 50
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 69
cagtagtaat taaaagagaa ggaccacact cagcgcgcgc atgcgcagtt                50

<210> SEQ ID NO 70
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 70
atgcggacga tgtgtgattg                                                 20

<210> SEQ ID NO 71
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 71
acggctgcga atttcacttt                                                 20

<210> SEQ ID NO 72
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 72
acacgtcgaa atcaaagggg                                                 20

<210> SEQ ID NO 73
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 73
tcattggtgc cgagttgttc                                                 20

<210> SEQ ID NO 74
<211> LENGTH: 20
<212> TYPE: DNA
<213> ORGANISM: artificial sequence -continued

```
<220> FEATURE:
<223> OTHER INFORMATION: Description of Artificial Sequence: Synthetic
      oligonucleotide

<400> SEQUENCE: 74
gaacaactcg gcaccaatga                                                                  20

<210> SEQ ID NO 75
<211> LENGTH: 20
<212> TYPE: DNA
<213> ORGANISM: artificial sequence
<220> FEATURE:
<223> OTHER INFORMATION: Description of Artificial Sequence: Synthetic
      oligonucleotide

<400> SEQUENCE: 75
gcacacacac cacacagtag                                                                  20
```

MAIZE GENE ZmRAVL1 AND FUNCTIONAL SITE AND USE THEREOF

CROSS-REFERENCE TO RELATED APPLICATIONS

This application is a U.S. national stage application, filed under 35 U.S.C. § 371(c), based on International Patent Application No. PCT/CN2020/095099, filed on Jun. 9, 2020, which claims priority to Chinese Patent Application No. 201910496614.6 filed on Jun. 10, 2019.

REFERENCE TO SEQUENCE LISTING

The instant application contains a Sequence Listing which has been filed electronically in ASCII format and is hereby incorporated by reference in its entirety. Said ASCII copy, created on Jun. 1, 2022 and having a size of 78,174 bytes, is named 132173_00202_SL.txt.

TECHNICAL FIELD

The invention relates to the field of plant gene map cloning and molecular breeding, and specifically relates to maize gene ZmRAVL1 and a related functional site as well as the corresponding use.

BACKGROUND OF THE INVENTION

Maize is the world's largest food crop, and now the total maize yield across the world has exceeded 1 billion tons. However, for the climate change, there remains very little space to enhance the maize yield by purely increasing the planting acreage of maize. A fundamental solution to this challenge is to fully explore the huge potential of maize genetic resources, and a significant increase in yield per unit area of maize is a main approach to guarantee a continuous increase in total yield of maize. The formation of crop yield is mainly composed of three elements: ear number per mu (1 mu≈0.0667 hectares), kernel number per ear, and thousand kernel weight. Since the maize variety has now basically a single ear, the ear number per mu is mainly determined by the density per mu.

It was believed that the yield improvement was mainly caused by enhancement of high-density tolerance, lodging resistance, and resistance (e.g., diseases and insects resistance, drought resistance, high temperature resistance, cold resistance, etc.) (Duvick 2005). In recent years, both production practices and research results have shown that increasing plant density is one of the main factors contributing to a continuous increase in maize yield, and the plant density of maize depends on its plant architecture. Plant architecture improvement is a major means of cultivating high-density tolerance and high-yielding maize varieties, and a compact and reasonable plant architecture is an important external morphological index to high-density tolerance and high-yielding maize varieties. Leaf angle is a significant factor that affects the compactness of maize plant architecture, and it has an immediate influence on appropriate distribution of light on the maize population canopy, which in turn affects the light interception capability of the maize canopy and the efficiency of light energy utilization by population, and ultimately affects the population yield.

Stalk-leaf angle is a key morphological index to the compactness of maize plants, and it has an immediate influence on appropriate distribution of light on the maize population canopy, which ultimately affects the population yield. A ligule region is a key tissue part that determines the stalk-leaf angle, and includes ligule and auricle. Through mutant analysis, a plurality of genes for controlling the erection and development of the ligule region have been cloned currently, including LG1, LG2, LGN, Wab1, DRL1, DRL2 and other genes. However, leaf angle is a complex quantitative trait. Researchers use different mapping populations to carry out a lot of mapping studies on quantitative trait locus (QTL) (Mickelson et al. 2002; Ku et al. 2010; Tian et al. 2011; Ku et al. 2012). A genome-wide linkage and association study of leaf angle in maize nested association mapping (NAM) population (Tian et al. 2011) was carried out to detect a total of 30 leaf angle QTLs and 203 associated SNPs (single nucleotide polymorphism). Ku et al. (Ku et al. 2012) conducted a comprehensive meta-analysis on the leaf angle QTLs mapped in different studies, and identified multiple leaf angle QTLs that were consistently detected in different populations. The study on the leaf angle of the whole maize still mainly stays at a preliminary mapping level, and the genetic and molecular regulatory network built by the maize leaf angle is far from clear.

As a result, the present invention aims to clone more maize leaf angle associated genes, study on the mutual regulation relationship therebetween, expounding on the genetic and molecular regulatory mechanism of the maize leaf angle, exploration of excellent allelic variation in maize germplasm resources, and development of molecular markers that can be directly used for molecular design breeding will provide important theoretical guidance and technical support for the cultivation of high-density tolerant and high-yielding maize varieties.

SUMMARY OF THE INVENTION

In one aspect, the present invention relates to a maize gene ZmRAVL1 and a functional site functional site, which can be used to control the plant architecture, through leaf angle. The present invention demonstrates that a reduced ZmRAVL1 expression has an influence on plant architectures.

In one aspect, the present invention relates to the use of a polynucleotide sequence in plant breeding, wherein the polynucleotide sequence comprises a sequence selected from the group consisting of:

a) a sequence of SEQ ID No: 1;

b) a sequence having at least 85%, 90%, 91%, 92%, 93%, 94%, 95%, 96%, 97%, 98%, 98.5%, 99% or 99.5% identity with the sequence set forth in SEQ ID No: 1;

c) an essentially complementary sequence of the sequence set forth in a) or b);

d) a reverse sequence of the sequence set forth in a) or b);

e) a reverse complementary sequence of the sequence set forth in a) or b);

f) a sequence obtained from the above sequences by modifications such as addition and/or substitution and/or deletion of one or more nucleotides, wherein the above sequences can be used to control a plant architecture.

In one embodiment of the present invention, the plant architecture is controlled through leaf angle.

In one embodiment of the present invention, the plant is a monocotyledonous plant or a dicotyledonous plant, preferably the plant is a food crop, and more preferably the plant is selected from one or more of rice, maize, wheat, barley, sorghum, *Brassica* genus plant (eg., *Brassica campestris, Brassica oleracea, Brassica napus, Brassica rapa* L., *Brassica juncea*, and *Brassica caulorapa* Pasq.), alfalfa, rye, soybean, sunflower, millet, tobacco, potato, peanut, cotton, coffee, cocoa, pineapple, tea, banana, mango, olive, papaya, beet, sugar cane, oat, strawberry, blueberry, and *Arabidopsis*.

In another aspect, the present invention relates to a method for controlling a plant architecture, such as leaf angle, comprising disrupting ZmRAVL1 gene in a plant or a gene homologous to the ZmRAVL1 gene in other plants, wherein preferably the plant is a monocotyledonous plant or a dicotyledonous plant, more preferably the plant is a food crop, and further preferably the plant is selected from one or more of rice, maize, wheat, barley, sorghum, *Brassica* genus plant (eg., *Brassica campestris, Brassica oleracea, Brassica napus, Brassica rapa* L., *Brassica juncea*, and *Brassica caulorapa* Pasq.), alfalfa, rye, soybean, sunflower, millet, tobacco, potato, peanut, cotton, coffee, cocoa, pineapple, tea, banana, mango, olive, papaya, beet, sugar cane, oat, strawberry, blueberry, and *Arabidopsis*.

In one embodiment of the present invention, wherein the disrupting comprises disrupting the function, expression level, activity, or combination thereof of the gene.

In another embodiment of the present invention, wherein the disrupting is achieved by knock-out or knock-down of the gene, for example by RNAi technology.

In a further embodiment of the present invention, wherein the disrupting is achieved by regulating upstream regulatory genes of the gene, such as by regulating DRL1 and/or DRL2, optionally, for example, by regulating expression level, activity or a combination thereof of DRL1 and/or DRL2, and optionally, for example, by regulating binding of DRL1 and/or DRL2 to a target.

In another embodiment of the present invention, wherein the disrupting is achieved by a genome editing system such as CRISP/Cas, TALEN, ZFN or other genome editing systems.

In another aspect, the present invention relates to the use of a protein in regulating plant architecture, such as leaf angle, wherein the protein comprises the sequence defined by (i), (ii) or (iii):

(i) an amino acid sequence set forth in SEQ ID No: 27;

(ii) an amino acid sequence having at least 85%, 90%, 91%, 92%, 93%, 94%, 95%, 96%, 97%, 98%, 98.5%, 99% or 99.5% identity with the amino sequence set forth in SEQ ID No: 27;

(iii) an amino acid sequence obtained from the above sequences by modification such as addition and/or substitution and/or deletion of one or more amino acid residues, wherein the above amino acid sequences can be used to regulate plant architecture such as leaf angle, wherein preferably the plant is a monocotyledonous plant or a dicotyledonous plant, more preferably the plant is a food crop, and further more preferably the plant is selected from one or more of rice, maize, wheat, barley, sorghum, *Brassica* genus plant (eg., *Brassica campestris, Brassica oleracea, Brassica napus, Brassica rapa* L., *Brassica juncea*, and *Brassica caulorapa* Pasq.), alfalfa, rye, soybean, sunflower, millet, tobacco, potato, peanut, cotton, coffee, cocoa, pineapple, tea, banana, mango, olive, papaya, beet, sugar cane, oat, strawberry, blueberry, and *Arabidopsis*.

In a further aspect, the present invention relates to the use of a gene encoding a protein as defined in the present invention in regulating a plant architecture, such as leaf angle, wherein preferably the plant is a monocotyledonous or dicotyledonous plant, more preferably the plant is a food crop, and further more preferably the plant is selected from one or more of rice, maize, wheat, barley, sorghum, *Brassica* genus plant (eg., *Brassica campestris, Brassica oleracea, Brassica napus, Brassica rapa* L., *Brassica juncea*, and *Brassica caulorapa* Pasq.), alfalfa, rye, soybean, sunflower, millet, tobacco, potato, peanut, cotton, coffee, cocoa, pineapple, tea, banana, mango, olive, papaya, beet, sugar cane, oat, strawberry, blueberry, and *Arabidopsis*.

In one embodiment, wherein the gene encoding the protein comprises the following sequence:

(i) a nucleotide sequence set forth in SEQ ID No: 26;

(ii) a cDNA sequence of the nucleotide sequence set forth in SEQ ID No: 26;

(iii) a promoter sequence of the nucleotide sequence set forth in SEQ ID No: 26;

(iv) a nucleotide sequence having at least 50%, 55%, 60%, 65%, 70%, 75%, 80%, 85%, 90%, 91%, 92%, 93%, 94%, 95%, 96%, 97%, 98%, 98.5%, 99% or 99.5% identity with the nucleotide sequence set forth in SEQ ID No: 26;

(v) a cDNA sequence of the nucleotide sequence of (iv);

(vi) a promoter sequence of the nucleotide sequence of (iv);

(vii) a nucleotide sequence obtained from the above sequences by modification such as addition and/or substitution and/or deletion of one or more amino acid residues, wherein the above sequences can be used to regulate a plant architecture such as leaf angle, wherein, preferably the plant is a monocotyledonous plant or a dicotyledonous plant, more preferably the plant is a food crop, and further more preferably the plant is selected from one or more of rice, maize, wheat, barley, sorghum, *Brassica* genus plant (eg., *Brassica campestris, Brassica oleracea, Brassica napus, Brassica rapa* L., *Brassica juncea*, and *Brassica caulorapa* Pasq.), alfalfa, rye, soybean, sunflower, millet, tobacco, potato, peanut, cotton, coffee, cocoa, pineapple, tea, banana, mango, olive, papaya, beet, sugar cane, oat, strawberry, blueberry, and *Arabidopsis*.

In a further aspect, the present invention relates to the use of a gene encoding the protein as defined in the present invention in the cultivation of high-density tolerant plants, wherein preferably the plant is a monocotyledonous or dicotyledonous plant, more preferably the plant is a food crop, and further more preferably the plant is selected from one or more of rice, maize, wheat, barley, sorghum, *Brassica* genus plant (eg., *Brassica campestris, Brassica oleracea, Brassica napus, Brassica rapa* L., *Brassica juncea*, and *Brassica caulorapa* Pasq.), alfalfa, rye, soybean, sunflower, millet, tobacco, potato, peanut, cotton, coffee, cocoa, pineapple, tea, banana, mango, olive, papaya, beet, sugar cane, oat, strawberry, blueberry, and *Arabidopsis*.

In one embodiment of the present invention, the gene is ZmRAVL1 gene in a plant or a gene homologous to the ZmRAVL1 gene.

In a further aspect, the present invention relates to an isolated nucleic acid molecule comprising a promoter functional in a plant cell positioned to provide for expression of a polynucleotide having the following nucleotide sequence:

(i) a nucleotide sequence set forth in SEQ ID No: 26;

(ii) a cDNA sequence of the nucleotide sequence set forth in SEQ ID No: 26;

(iii) a promoter sequence of the nucleotide sequence set forth in SEQ ID No: 26;

(iv) a nucleotide sequence having at least 50%, 55%, 60%, 65%, 70%, 75%, 80%, 85%, 90%, 91%, 92%, 93%, 94%, 95%, 96%, 97%, 98%, 98.5%, 99% or 99.5% identity with the nucleotide sequence set forth in SEQ ID No: 26;

(v) a cDNA sequence of the nucleotide sequence of (iv);

(vi) a promoter sequence of the nucleotide sequence of (iv);

(vii) a nucleotide sequence obtained from the above sequences by modifications through addition and/or substitution and/or deletion of one or more amino acid residues, wherein the above sequences can be used to regulate plant architecture, wherein, preferably the plant is a monocotyledonous plant or a dicotyledonous plant, more preferably the plant is a food crop, and further more preferably the plant is selected from one or more of rice, maize, wheat, barley, sorghum, Brassica genus plant (eg., Brassica campestris, Brassica oleracea, Brassica napus, Brassica rapa L., Brassica juncea, and Brassica caulorapa Pasq.), alfalfa, rye, soybean, sunflower, millet, tobacco, potato, peanut, cotton, coffee, cocoa, pineapple, tea, banana, mango, olive, papaya, beet, sugar cane, oat, strawberry, blueberry, and Arabidopsis.

In another aspect, the present invention relates to an RNAi vector comprising a sequence targeting a gene controlling a plant architecture, such as leaf angle, wherein preferably the plant is a monocotyledonous or dicotyledonous plant, more preferably the plant is a food crop, and further more preferably the plant is selected from one or more of rice, maize, wheat, barley, sorghum, Brassica genus plant (eg., Brassica campestris, Brassica oleracea, Brassica napus, Brassica rapa L., Brassica juncea, and Brassica caulorapa Pasq.), alfalfa, rye, soybean, sunflower, millet, tobacco, potato, peanut, cotton, coffee, cocoa, pineapple, tea, banana, mango, olive, papaya, beet, sugar cane, oat, strawberry, blueberry, and Arabidopsis.

In one embodiment of the present invention, the gene is ZmRAVL1 gene in a plant or a gene homologous to the ZmRAVL1 gene.

In a further aspect, the present invention relates to a method of producing a transgenic plant with a compact plant architecture, comprising obtaining a transgenic plant cell with inhibited expression of the ZmRAVL1 gene or the gene products thereof compared to a wild type plant, and regenerating a transgenic plant from said transgenic plant cell.

In one embodiment of the present invention, the transgenic plant cell is obtained by mutagenesis, gene editing, or RNA-mediated inhibition of the ZmRAVL1 gene.

In one embodiment of the present invention, the mutagenesis is selected from the group consisting of random mutagenesis and screening, site-directed mutagenesis, PCR mutagenesis, insertional mutagenesis, physical mutagenesis, chemical mutagenesis, and irradiation.

In one embodiment of the present invention, the gene editing is achieved by providing an endonuclease selected from a meganuclease, a Zinc finger endonuclease, a TALEN endonuclease or a CRISPR endonuclease.

In one embodiment of the present invention, the RNA-mediated inhibition consists of introducing into a plant cell a polynucleotide encoding a RNA molecule that is at least 70% complementary to at least 15 continuous nucleotides of the ZmRAVL1 gene.

In one embodiment of the present invention, the plant is selected from wherein the plant is a monocotyledonous plant or a dicotyledonous plant, more preferably the plant is a food crop, and further more preferably the plant is selected from one or more of rice, maize, wheat, barley, sorghum, Brassica genus plant (eg., Brassica campestris, Brassica oleracea, Brassica napus, Brassica rapa L., Brassica juncea, and Brassica caulorapa Pasq.), alfalfa, rye, soybean, sunflower, millet, tobacco, potato, peanut, cotton, coffee, cocoa, pineapple, tea, banana, mango, olive, papaya, beet, sugar cane, oat, strawberry, blueberry, and Arabidopsis.

In a further aspect, the present invention relates to a construct comprising a polynucleotide encoding a RNA molecule comprising a sequence that is at least 70% complimentary to at least 15 continuous nucleotides of the ZmRAVL1 gene, wherein the expression of the construct in a plant results inhibited expression of ZmRAVL1 gene.

In one embodiment of the present invention, the RNA molecule is selected from the group consisting of an anti-sense RNA, miRNA, siRNA and long non-coding RNA.

In one embodiment of the present invention, the RNA molecule encodes an RNAi, wherein the sequence of the RNAi targets SEQ ID NO: 45 or a functional variant thereof.

In a further aspect, the present invention relates to a RNAi vector comprising a sequence targeting a gene controlling a plant architecture, such as leaf angle, wherein preferably the plant is a monocotyledonous or dicotyledonous plant, more preferably the plant is a food crop, and further more preferably the plant is selected from one or more of rice, maize, wheat, barley, sorghum, Brassica genus plant (eg., Brassica campestris, Brassica oleracea, Brassica napus, Brassica rapa L., Brassica juncea, and Brassica caulorapa Pasq.), alfalfa, rye, soybean, sunflower, millet, tobacco, potato, peanut, cotton, coffee, cocoa, pineapple, tea, banana, mango, olive, papaya, beet, sugar cane, oat, strawberry, blueberry, and Arabidopsis.

In one embodiment of the present invention, the vector comprises the above construct.

In a further aspect, the present invention relates to a targeting sgDNA of Cas9 of a sequence of CTCTTCGAGTAGGTTTTCC (SEQ ID No: 54).

In another aspect, the present invention also relates to a single guide (sg) RNA molecule wherein said sgRNA recognizing a DNA target sequence comprising 16 to 25 nucleotides wherein said DNA target sequence is a portion of the full length sequence of ZmRAVL1 gene.

In one embodiment of the present invention, the said sgRNA comprises a crRNA sequence and a tracrRNA sequence, wherein the crRNA sequence can bind to the sequence of SEQ ID No: 54.

In another aspect, the present invention also relates to a composition comprising the above sgRNA, wherein the composition further comprises a RNA-guided endonuclease.

In another aspect, the present invention also relates to a host cell comprising the above vector, or the above composition.

In another aspect, the present invention also relates to a plant, plant part or plant cell comprising the above vector, the above composition or the above host cell.

In one embodiment of the present invention, the plant is produced according to the above method.

In one embodiment of the present invention, the plant is a monocotyledonous plant or a dicotyledonous plant, more preferably the plant is a food crop, and further more preferably the plant is selected from one or more of rice, maize, wheat, barley, sorghum, Brassica genus plant (eg., Brassica campestris, Brassica oleracea, Brassica napus, Brassica rapa L., Brassica juncea, and Brassica caulorapa Pasq.), alfalfa, rye, soybean, sunflower, millet, tobacco, potato, peanut, cotton, coffee, cocoa, pineapple, tea, banana, mango, olive, papaya, beet, sugar cane, oat, strawberry, blueberry, and Arabidopsis.

In another aspect, the present invention also relates to a commodity product made from the above transgenic plant, plant cells or plant parts thereof.

In one embodiment of the present invention, the commodity product is protein concentrate, protein isolate, cereal, starch, seeds, meal, flour, biomass or seed oil.

In one embodiment of the present invention a pair of primers for identifying or assistantly identifying the leaf angle trait in maize, which correspond to the above molecular marker, each pair of primers has a sequence selected from SEQ ID Nos:3-24.

In another aspect, the present invention also relates to a kit for identifying or assistantly identifying the leaf angle in maize, which comprises at least one pair of the above primers.

In another aspect, the present invention also relates to a use of the above molecular marker, the pair of primers, or the kit in identifying or assistantly identifying the leaf angle trait in maize or in maize breeding.

In another aspect, the present invention also relates to a polynucleotide sequence comprising a sequence selected from:

a) a sequence of SEQ ID No: 1;

b) a sequence having at least 85%, 90%, 91%, 92%, 93%, 94%, 95%, 96%, 97%, 98%, 98.5%, 99% or 99.5% identity with the sequence set forth in SEQ ID No: 1;

c) an essentially complementary sequence of the sequence set forth in a) or b);

d) a reverse sequence of the sequence set forth in a) or b);

e) a reverse complementary sequence of the sequence set forth in a) or b);

f) a sequence obtained from the above sequences by modifications such as addition and/or substitution and/ or deletion of one or more nucleotides, wherein the above sequences can be used to control a plant architecture, wherein preferably the plant is a monocotyledonous plant or dicotyledonous plant, more preferably the plant is a food crop, and further preferably the plant is selected from one or more of rice, maize, wheat, barley, sorghum, *Brassica* genus plant (eg., *Brassica campestris, Brassica oleracea, Brassica napus, Brassica rapa* L., *Brassica juncea*, and *Brassica caulorapa* Pasq.), alfalfa, rye, soybean, sunflower, millet, tobacco, potato, peanut, cotton, coffee, cocoa, pineapple, tea, banana, mango, olive, papaya, beet, sugar cane, oat, strawberry, blueberry, and *Arabidopsis*.

BRIEF DESCRIPTION OF THE DRAWINGS

FIGS. 2A-2C depict the nucleic acid molecular sequence of ZmRAVL1 (SEQ ID NO: 26).

FIG. 3 depicts the protein sequence of ZmRAVL1 (SEQ ID NO: 27).

FIG. 4 depicts a phylogenetic analysis of B3 domain proteins in maize, sorghum, rice and *Arabidopsis*, wherein a phylogenetic analysis of B3 domain-containing proteins in maize, rice, sorghum and *Arabidopsis* is shown. RAVL1 in rice and ZmRAVL1 in maize are highlighted in red.

FIG. 9 depicts expression patterns of ZmRAVL1 in the near-isogenic lines, in which different parts of near-isogenic lines were sampled at V5 developing stage to detect the ZmRAVL1 expression. L5 indicates the uppermost mature blade, and L6 and L7 indicate two immature inward blades. L5 (Leaf5), L6 (Leaf6) and L7 (Leaf7) each include a blade, a ligule, and a sheath.

FIG. 10 depicts a reduced leaf angle of RNAi transgenic plants, in which (A) shows a picture of phenotypes of wild type WT and two whole RNAi transgenic plants, where the white arrows indicate the lower leaf angle (LLA), the middle leaf angle (MLA) and the upper leaf angle (ULA), respectively; (B) shows relative expression levels of wild type WT and two RNAi transgenic lines ZmRAVL1; and (C) shows a phenotypic statistic comparison between wild type WT and the transgenic events of two RNAi transgenic lines ZmRAVL1. Data statistical significance values (P values) are all at the top of the column.

DETAILED DESCRIPTION OF THE INVENTION

Figure 1:
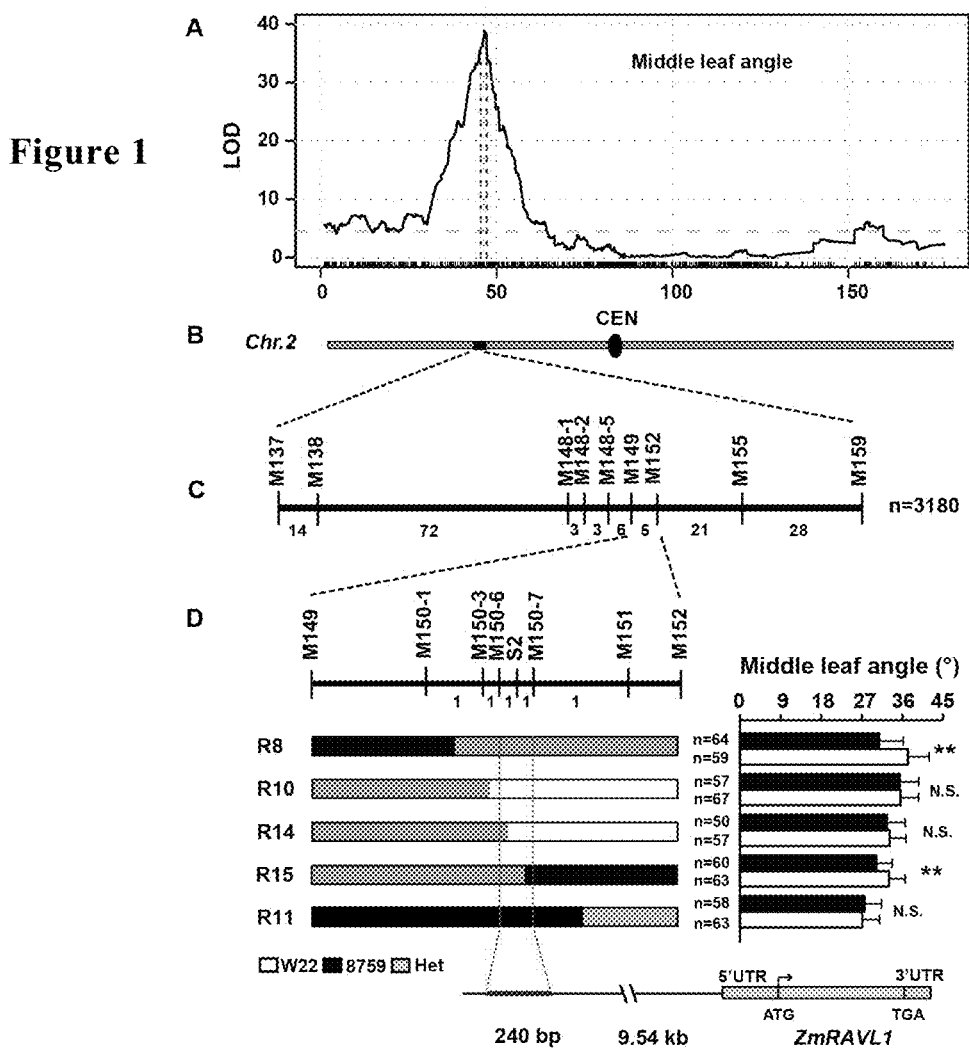
FIG. 1 depicts fine-mapping for middle leaf angle in the maize-teosinte BC2S3 population.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of botany, microbiology, tissue culture, molecular biology, chemistry, biochemistry and recombinant DNA technology, bioinformatics which are within the skill of the art. Such techniques are explained fully in the literature.

As used herein, a "plant architecture" refers to the three-dimensional organization of the plant body, is of major agronomic importance, strongly influencing the suitability of a plant for cultivation, its yield and the efficiency with which it can be harvested. Plant architecture includes many agronomically important traits such as branching pattern, root and shoot diameter, size, number, position and shape of leaves and flower organs.

In a preferred embodiment of the present invention, the plant architecture is controlled through leaf angle (stalk-leaf angle). Leaf angle is a significant factor that affects the compactness of a maize plant architecture, and it has an immediate influence on appropriate distribution of light on the maize population canopy, which in turn affects the light interception capability of the maize canopy and the efficiency of light energy utilization by population, and ultimately affects the population yield. Studies show that the more upright the upper leaves, the lower the light interception capability, and the higher the light transmittance of the population. Thus, the middle and lower leaves in the population are in a better sunlight state, which is convenient for the leaves to make full use of light energy efficiently and improve the net photosynthetic rate of the plant.

The plant according to all aspects of the invention described herein may be a monocot or a dicot plant. Preferably, the plant is a crop plant. By crop plant is meant any plant which is grown on a commercial scale for human or animal consumption or use. In a preferred embodiment, the plant is a cereal. Preferably, the plant is selected from one or more of rice, maize, wheat, barley, sorghum, *Brassica* genus plant (eg., *Brassica campestris, Brassica oleracea, Brassica napus, Brassica rapa* L., *Brassica juncea*, and *Brassica caulorapa* Pasq.), alfalfa, rye, soybean, sunflower, millet, tobacco, potato, peanut, cotton, coffee, cocoa, pineapple, tea, banana, mango, olive, papaya, beet, sugar cane, oat, strawberry, blueberry, and *Arabidopsis.*

As used herein, a "plant cell" refers to a biological cell of a plant, taken from a plant or derived through culture from a cell taken from a plant.

As used herein, "plant part" includes but not limited to leaf, stem, root, tuber, seeds, endosperm, ovule and pollen. The plant part of the invention may be viable, non-viable, regenerable and/or non-regenerable. The present invention also encompasses and provides transformed plant cells comprising the DNA molecule of the invention. The transformed plant cell or transgenic plant cell of the invention comprising regenerable and/or non-regenerable plant cells.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene.

To determine the percent identity between two nucleotide sequences or amino acid sequences, the sequences are aligned for optimal comparison purposes (for example, in order for optimal alignment with another nucleotide sequence or amino acid sequence, a vacancy may be introduced into the sequence of the first nucleotide sequence or amino acid sequence). The percent identity between the two sequences is a function of the number of positions of identical nucleotide or amino acid residues shared by the sequences (i.e., % identity=(number of positions of identical nucleotide or amino acid residues #/total number of positions #)×100). If sequences of different lengths are compared, the total number of positions is determined by the shorter sequence. The percent identity between the two sequences can also be determined by mathematical algorithms.

An example of a non-restrictive mathematical algorithm application for comparing two sequences is BLAST (https://blast.ncbi.nlm.nih.gov/). At the time of applying the BLAST program, the default parameters of the program may be applied, or adjusted as needed. Those skilled in the art know how to adjust the parameters, and how to adjust them accordingly with reference to the NCBI documentation.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Non-limiting examples of algorithms that are suitable for determining percent sequence identity and sequence similarity are the BLAST and BLAST 2.0 algorithms.

Suitable homologues can be identified by sequence comparisons and identifications of conserved domains. There are predictors in the art that can be used to identify such sequences. The function of the homologue can be identified as described herein and a skilled person would thus be able to confirm the function, for example when overexpressed in a plant. Thus, the nucleotide sequences of the invention and described herein can also be used to isolate corresponding sequences from other organisms, particularly other plants, for example crop plants. In this manner, methods such as PCR, hybridization, and the like can be used to identify such sequences based on their sequence homology to the sequences described herein. Topology of the sequences and the characteristic domains structure can also be considered when identifying and isolating homologs. Sequences may be isolated based on their sequence identity to the entire sequence or to fragments thereof. In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen plant. The hybridization probes may be genomic DNA fragments, cDNA fragments, RNA fragments, or other oligonucleotides, and may be labelled with a detectable group, or any other detectable marker. Methods for preparation of probes for hybridization and for construction of cDNA and genomic libraries are generally known in the art and are disclosed in Sambrook, et al., (1989) Molecular Cloning: A Library Manual (2d ed., Cold Spring Harbor Laboratory Press, Plainview, New York).

The term "gene" is used broadly to refer to a DNA nucleic acid associated with a biological function. Thus, genes may include introns and exons as in the genomic sequence, or may comprise only a coding sequence as in cDNAs, and/or may include cDNAs in combination with regulatory sequences.

The gene according to the present invention also includes variant sequences derived from deletion, substitution, insertion or addition in one or more nucleotides of the ZmRAVL1 gene, which maintains the regulatory activity of the ZmRAVL1 gene. Gene mutation is a sudden inheritable variable phenomenon occurred in genomic DNA molecule. At the molecular level, gene mutation refers to alteration in base pair composition or arrangement sequence occurred in gene structure. Gene mutation may be spontaneous or inducible, and methods of artificial mutagenesis include physical mutagenesis (such as gamma rays, x-rays, ultraviolet light, and neutron flux), chemical mutagenesis (such as alkylating agents, base analogs, and antibiotics) and biological mutagenesis (such as certain viruses and bacteria, etc.). Moreover, directed mutagenesis can be achieved using recombinant DNA techniques to make specific changes in DNA molecules at specific locations. Any of these well-known mutagenesis methods can be used to obtain variant sequences of the ZmRAVL1 gene comprising mutation, deletion, substitution, insertion or addition in one or more nucleotides.

Preferably, the nucleic acid molecule according to the present invention is operably linked to a heterologous promoter, to form a recombinant DNA molecule.

In another aspect, the present invention provides an expression cassette comprising the recombinant DNA molecule of the present invention, a recombinant vector comprising said expression cassette, a host cell comprising said recombinant vector, and a transgenic plant cell, transgenic plant and plant parts thereof comprising said recombinant DNA molecule.

The terms "polypeptide" and "protein" are used interchangeably herein and refer to amino acids in a polymeric form of any length, linked together by peptide bonds.

The term "promoter" typically refers to a nucleic acid control sequence located upstream from the transcriptional start of a gene and which is involved in the binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences.

The term "operably linked" as used herein refers to a functional linkage between the promoter sequence and the gene of interest, such that the promoter sequence is able to initiate transcription of the gene of interest.

The aspects of the invention involve recombination DNA technology and exclude embodiments that are solely based on generating plants by traditional breeding methods.

For the purposes of the invention, a "transgenetic plant" is a plant that has been genetically altered compared to the naturally occurring wild type (WT) plant. In one embodiment, a transgenetic plant is a plant that has been altered compared to the naturally occurring wild type (WT) plant using a mutagenesis method, such as any of the mutagenesis methods described herein. In one embodiment, the mutagenesis method is targeted genome modification or genome editing. In one embodiment, the plant genome has been altered compared to wild type sequences using a mutagenesis method. Such plants have an altered phenotype as described herein, such as compact plant architectures, reduced leaf angle, increased grain yield and harvested ears. Therefore, in this example, these traits are conferred by disrupting ZmRAVL1 gene. In one embodiment, the endogenous promoter or gene sequence is specifically targeted using targeted genome modification and the presence of a mutated gene or promoter sequence is not conferred by the presence of transgenes expressed in the plant. In other words, the genetically altered plant can be described as transgene-free. Nonetheless, in an alternative embodiment, the genetically altered plant is a transgenic plant. For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or (b) genetic control sequence(s) which is operably linked with the nucleic acid sequence according to the invention, for example a promoter, or (c) a) and b) are not located in their natural genetic environment or have been modified by recombinant methods, it being possible for the modification to take the form of, for example, a substitution, addition, deletion, inversion or insertion of one or more nucleotide residues.

The terms "reduced" as used herein are also interchangeable as used herein, the terms "reducing" means a decrease in the levels of ZMRAVL1 expression and/or activity by up to or more than 10%, 20%, 30%, 40%, 50%, 60%, 70%, 80% or 90% when compared to the level in a wild-type or control plant. Reducing may or may not encompass abolishes expression, preferably it does not. These reductions can be measured by any standard technique known to the skilled person. For example, a reduction in the expression and/or content levels of at least ZmRAVL1 expression may be a measure of protein and/or nucleic acid levels and can be measured by any technique known to the skilled person, such as, but not limited to, any form of gel electrophoresis or chromatography (e.g. HPLC).

In one embodiment, the mutation is introduced using mutagenesis or targeted genome editing. That is, in one embodiment, the invention relates to a method and plant that has been generated by genetic engineering methods as described above, and does not encompass naturally occurring varieties.

Targeted genome modification or targeted genome editing is a genome engineering technique that uses targeted DNA double-strand breaks (DSBs) to stimulate genome editing through homologous recombination (HR)-mediated recombination events. To achieve effective genome editing via introduction of site-specific DNA DSBs, four major classes of customisable DNA binding proteins can be used: meganucleases derived from microbial mobile genetic elements, ZF nucleases based on eukaryotic transcription factors, transcription activator-like effectors (TALEs) from *Xanthomonas* bacteria, and the RNA-guided DNA endonuclease Cas9 from the type II bacterial adaptive immune system CRISPR (clustered regularly interspaced short palindromic repeats). Meganuclease, ZF, and TALE proteins all recognize specific DNA sequences through protein-DNA interactions. Although meganucleases integrate nuclease and DNA-binding domains, ZF and TALE proteins consist of individual modules targeting 3 or 1 nucleotides (nt) of DNA, respectively.

Another genome editing method that can be used according to the various aspects of the invention is CRISPR. The use of this technology in genome editing is well described in the art, for example in U.S. Pat. No. 8,697,359 and references cited herein. In short, CRISPR is a microbial nuclease system involved in defense against invading phages and plasmids. CRISPR loci in microbial hosts contain a combination of CRISPR-associated (Cas) genes as well as noncoding RNA elements capable of programming the specificity of the CRISPR-mediated nucleic acid cleavage (sgRNA). Three types (I-III) of CRISPR systems have been identified across a wide range of bacterial hosts. One key feature of each CRISPR locus is the presence of an array of repetitive sequences (direct repeats) interspaced by short stretches of non-repetitive sequences (spacers). The noncoding CRISPR array is transcribed and cleaved within direct repeats into short crRNAs containing individual spacer sequences, which direct Cas nucleases to the target site (protospacer). The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

One major advantage of the CRISPR-Cas9 system, as compared to conventional gene targeting and other programmable endonucleases is the ease of multiplexing, where multiple genes can be mutated simultaneously simply by using multiple sgRNAs each targeting a different gene. In addition, where two sgRNAs are used flanking a genomic region, the intervening section can be deleted or inverted (Wiles et al., 2015).

Cas9 is thus the hallmark protein of the type II CRISPR-Cas system, and is a large monomeric DNA nuclease guided to a DNA target sequence adjacent to the PAM (protospacer adjacent motif) sequence motif by a complex of two noncoding RNAs: CRISPR RNA (crRNA) and trans-activating crRNA (tracrRNA). The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA. Heterologous expression of Cas9 together with an sgRNA can introduce site-specific double strand breaks (DSBs) into genomic DNA of live cells from various organisms. For applications in eukaryotic organisms, codon optimized versions of Cas9, which is originally from the bacterium *Streptococcus pyogenes*, have been used. The single guide RNA (sgRNA) is the second component of the CRISPR/Cas system that forms a complex with the Cas9 nuclease. sgRNA is a synthetic RNA chimera created by fusing crRNA with tracrRNA. The sgRNA guide sequence located at its 5' end confers DNA target specificity. Therefore, by modifying the guide sequence, it is possible to create sgRNAs with different target specificities. sgRNA is designed to recognize a DNA target sequence comprising 16 to 25 nucleotides wherein said DNA target sequence is selected from the group comprising the target gene and a regulatory sequence thereof. The canonical length of the guide sequence is 20 bp. In plants, sgRNAs have been expressed using plant RNA polymerase III promoters, such as U6 and U3. Accordingly, using techniques known in the art it is possible to design sgRNA molecules that targets a ZmRAVL1 gene or promoter sequence as described herein. In one embodiment, the method comprises using any of the nucleic acid constructs or sgRNA molecules described herein.

Cas9 expression plasmids for use in the methods of the invention can be constructed as described in the art.

In one embodiment of the method, the transgenic plant with reduced leaf angel is produced by RNA-mediated inhibition of the ZmRAVL1 gene expression in a plant. In particular, said RNA-mediated inhibition of the ZmRAVL1 gene expression is achieved by introducing into a plant cell a polynucleotide encoding a RNA molecule comprising a sequence that is essentially complementary to at least 15 continuous nucleotides of the ZmRAVL1 gene or fragments thereof, wherein the expression of the polynucleotide results in inhibited expression of the ZmRAVL1 gene in said plant. A construct comprising a polynucleotide encoding a RNA molecule comprising a sequence that is essentially complementary to at least 15 continuous nucleotides of the ZmRAVL1 gene or fragments thereof, wherein the expression of the construct results in inhibited expression of the ZmRAVL1 gene in said plant is also encompassed in the scope of the invention.

In an embodiment, the above polynucleotide encoding a RNA molecule encompass oligonucleotides having a length of 15-25 nucleotides (15-mers, 16-mers, 17-mers, 18-mers, 19-mers, 20-mers, 21-mers, 22-mers, 23-mers, 24-mers, or 25-mers) or fragments thereof, or medium-length polynucleotides having a length of 26 or more nucleotides (polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or fragments thereof or long polynucleotides having a length greater than about 300 nucleotides (for example, polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target gene including coding or non-coding or both coding and non-coding portions of the target gene), wherein the polynucleotides or fragments thereof are homologous or complementary to the target ZmRAVL1 gene, and suppresses the expression of the target ZmRAVL1 gene when expressed in a plant cell.

Many RNA-mediated inhibition methods are known in the art. Non-limiting examples of RNA molecules used in the RNA-mediated inhibition methods include, but are not limited to, antisense RNAs, miRNAs, siRNAs and long non-coding RNAs. Antisense RNA is a single-stranded RNA that is complementary to a messenger RNA (mRNA) strand transcribed in a cell. When antisense RNA is expressed in a cell, it binds to a specific messenger RNA molecule and inactivates it. An siRNA is a double-stranded RNA molecule, 20-25 base pairs in length. After separating into single strands and integrating into an active RISC complex, it base-pairs to its target mRNA and induces cleavage of the target mRNA, thereby preventing it from being used as a translation template. A miRNA is a small RNA, typically about 21 nucleotides, that has the ability to modulate the expression of a target gene by binding to mRNA for the target protein, leading to destabilization or translational inhibition of the target protein mRNA, ultimately resulting in reduction of the target protein. Methods for selecting and designing siRNAs and miRNAs for gene inhibition are well known in the art. Long non-coding RNAs (long ncRNA or lncRNA) are non-protein coding transcripts longer than 200 nucleotides (Perkel, BioTechniques, 54 (6):301-304 (2013)). In contrast to many small RNAs which exhibit strong conservation across diverse species, long ncRNAs in general lack strong conservation. Long ncRNAs can be categorized, according to their proximity to protein coding genes in the genome, into five categories; sense, antisense, bidirectional, intronic, and intergenic, and regulate gene expression through a diverse group of mechanisms, such as through gene transcription (e.g., through gene-specific transcription regulation and regulation of basal transcription machinery), post-transcriptional regulation (e.g., through mRNA splicing, translation and siRNA-directed gene regulation) or through epigenetic regulation. The effect of a siRNA, a miRNA or a long non-coding RNA on target gene inhibition can be assessed by a beto-glucuronidase or uidA gene (GUS) reporter expression comparison.

The polynucleotide encoding the RNA molecule of the present invention can be single- or double-stranded RNA or single- or double-stranded DNA or double-stranded DNA/RNA hybrids or modified analogues thereof, and can be of oligonucleotide lengths or longer. In more specific embodiments of the invention, the polynucleotides that provide RNA molecule of the invention in the plant cell are selected from the group consisting of (a) a single-stranded RNA molecule (ssRNA), (b) a single-stranded RNA molecule that self-hybridizes to form a double-stranded RNA molecule, (c) a double-stranded RNA molecule (dsRNA), (d) a single-stranded DNA molecule (ssDNA), (e) a single-stranded DNA molecule that self-hybridizes to form a double-stranded DNA molecule, and (f) a single-stranded DNA molecule including a modified Pol III gene that is transcribed to an RNA molecule, (g) a double-stranded DNA molecule (dsDNA), (h) a double-stranded DNA molecule including a modified Pol III gene that is transcribed to an RNA molecule, (i) a double-stranded, hybridized RNA/DNA molecule, or combinations thereof. In some embodiments, these polynucleotides include chemically modified nucleotides or non-canonical nucleotides. In embodiments of the method, the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In one embodiment, the polynucleotides include single-stranded DNA or single-stranded RNA that self-hybridizes to form a hairpin structure having an at least partially double-stranded structure including at least one segment that will hybridize to RNA transcribed from the gene targeted for suppression. Not intending to be bound by any mechanism, it is believed that such polynucleotides are or will produce single-stranded RNA with at least one segment that will hybridize to RNA transcribed from the gene targeted for inhibition. In certain other embodiments, the polynucleotides further includes a promoter, generally a promoter functional in a plant, for example, a pol II promoter, a pol III promoter, a pol IV promoter, or a pol V promoter. One skilled in the art is aware that the polynucleotides according to the invention have sequence complementarity that need not be 100 percent, but is at least sufficient to provide a RNA molecule permit hybridization to RNA transcribed from the target gene or DNA of the target gene to form a duplex to permit a gene silencing mechanism. Thus, in embodiments, a polynucleotide fragment is designed to be essentially identical to, or essentially complementary to, a sequence of 15 or more contiguous nucleotides in either the target ZmRAVL1 gene sequence or messenger RNA transcribed from the target gene. By "essentially identical" is meant having 100 percent sequence identity or at least about 70, 75, 80, 81, 82, 83, 84, 85, 86, 87, 88, 89, 90, 91, 92, 93, 94, 95, 96, 97, 98, or 99 percent sequence identity when compared to the sequence of at least 15 or more contiguous nucleotides (for example, at least 16, 17, 18, 19, 20, 21, 22, 23, 24, 25, 26, 27, 28, 29, 30 or more contiguous nucleotides) in either the target gene or RNA transcribed from the target gene; by "essentially complementary" is meant having 100 percent sequence complementarity or at least about 70, 75, 80, 81, 82, 83, 84, 85, 86, 87, 88, 89, 90, 91, 92, 93, 94, 95, 96, 97, 98, or 99 percent sequence complementarity when compared to the sequence of at least 15 or more contiguous nucleotides (for example, at least 16, 17, 18, 19, 20, 21, 22, 23, 24, 25, 26, 27, 28, 29, 30 or more contiguous nucleotides) in either the target gene or RNA transcribed from the target gene. In some embodiments, polynucleotide molecules are designed to have 100 percent sequence identity with or complementarity to one allele or one family member of a given target gene.

RNA interference (RNAi) is another post-transcriptional gene-silencing phenomenon which may be used according to the methods of the invention. This is induced by double-stranded RNA in which mRNA that is homologous to the dsRNA is specifically degraded. It refers to the process of sequence-specific post-transcriptional gene silencing mediated by short interfering RNAs (siRNA). The process of RNAi begins when the enzyme, DICER, encounters dsRNA and chops it into pieces called small-interfering RNAs (siRNA). This enzyme belongs to the RNase III nuclease family. A complex of proteins gathers up these RNA remains and uses their code as a guide to search out and destroy any RNAs in the cell with a matching sequence, such as target mRNA.

In one embodiment, recombinant DNA constructs as described in U.S. Pat. No. 6,635,805, incorporated herein by reference, may be used.

The term "introduction", "transfection" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The resulting transformed plant cell may then be used to regenerate a transformed plant in a manner known to persons skilled in the art. The transfer of foreign genes into the genome of a plant is called transformation. Transformation of plants is now a routine technique in many species. Any of several transformation methods known to the skilled person may be used to introduce the nucleic acid construct or sgRNA molecule of interest into a suitable ancestor cell. The methods described for the transformation and regeneration of plants from plant tissues or plant cells may be utilized for transient or for stable transformation.

Transformation methods include the use of liposomes, electroporation, chemicals that increase free DNA uptake, injection of the DNA directly into the plant (microinjection), gene guns (or biolistic particle delivery systems (biolistics)) as described in the examples, lipofection, transformation using viruses or pollen and microprojection.

Methods may be selected from the calcium/polyethylene glycol method for protoplasts, ultrasound-mediated gene transfection, optical or laser transfection, transfection using silicon carbide fibers, electroporation of protoplasts, microinjection into plant material, DNA or RNA-coated particle bombardment, infection with (non-integrative) viruses and the like. Transgenic plants, can also be produced via *Agrobacterium tumefaciens* mediated transformation, including but not limited to using the floral dip/*Agrobacterium* vacuum infiltration method as described in Clough & Bent (1998) and incorporated herein by reference. Accordingly, in one embodiment, at least one nucleic acid construct or sgRNA molecule as described herein can be introduced to at least one plant cell using any of the above described methods. In an alternative embodiment, any of the nucleic acid constructs described herein may be first transcribed to form a preassembled Cas9-sgRNA ribonucleoprotein and then delivered to at least one plant cell using any of the above described methods, such as lipofection, electroporation or microinjection.

Optionally, to select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility is growing the seeds, if appropriate after sterilization, on agar plates using a suitable selection agent so that only the transformed seeds can grow into plants. As described in the examples, a suitable marker can be bar-phosphinothricin or PPT. Alternatively, the transformed plants are screened for the presence of a selectable marker, such as, but not limited to, GFP, GUS (β-glucuronidase). Other examples would be readily known to the skilled person. Alternatively, no selection is performed, and the seeds obtained in the above-described manner are planted and grown and ZmRAVL1 expression or protein levels measured at an appropriate time using standard techniques in the art. This alternative, which avoids the introduction of transgenes, is preferable to produce transgene-free plants.

Following DNA transfer and regeneration, putatively transformed plants may also be evaluated, for instance using PCR to detect the presence of the gene of interest, copy number and/or genomic organization. Alternatively or additionally, integration and expression levels of the newly introduced DNA may be monitored using Southern, Northern and/or Western analysis, both techniques being well known to persons having ordinary skill in the art. The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

The present invention is capable of breeding inbred lines with small stalk-leaf angles and upright leaves, and combining plant architecture improvement with utilization of heterosis, so as to cultivate high-density tolerant and high-yielding superior varieties.

Compared with the prior art, the present invention has at least the following beneficial technical effects:

1. The functional site for controlling the leaf angle phenotype is located to 240 bp (B73 reference genome) by fine-mapping, and a molecular biology experiment is carried out to demonstrate: in UPA2-NIL$^{8759}$ and UPA2-NIL$^{W22}$, a TG insertion or deletion leads to a difference in capability of binding to the DRL1 protein, and then the degrees of downstream ZmRAVL1 expression to repress LG1 activation are different, thereby resulting in different angle phenotypes. In the present invention, the allele that is capable of reducing the leaf angle originates from teosinte (8759), the wild species of maize, and the sequencing of the associated population composed of teosinte, landraces and modern breeding inbred lines shows that the allele is specifically present in teosinte. The key to breeding now is to select a superior inbred line, but because of the continuous artificial selection and trait improvement of the germplasm resources used in current breeding, the genetic basis is getting narrower and narrower. The elite alleles in the present invention originate from teosinte, which proves that the elite alleles that can be utilized in breeding are carried by teosinte, but this part of elite alleles may be lost in the process of domestication and improvement of maize. As such, the present invention expands sources of acquiring elite alleles and broadens the genetic basis for controlling phenotypic variation.

2. The expression level of ZmRAVL1 affects the change in leaf angle. The leaf angle increases as the expression level increases, and the leaf angle decreases as the expression level decreases. Therefore, the present invention provides a new idea of genetic engineering breeding to obtain a compact plant architecture of maize by reducing the expression level of ZmRAVL1. At the same time, the present invention uses the CRISPR/CAS9 system to obtain ZmRAVL1 gene knockout lines, and obtain homozygous mutants, whose ZmRAVL1 protein has lost its function, through isolation. The mutant has a smaller leaf angle and a more compact plant architecture, and does not exhibit ease of accompanying unfavorable phenotypes. The newly acquired mutants are more in line with the needs of breeding. Thus, the present invention provides a genetic engineering technique for regulating leaf angle variation by regulating the transcription level of ZmRAVL1, which provides excellent genetic resources for genetic engineering breeding. In the meantime, the present invention utilizes gene-editing techniques to obtain elite alleles that are more in line with breeding demands, which greatly shortens the selection process of elite alleles and provides the possibility of rapid and wide application of compact plant architectures with a reduced leaf angle in breeding practice.

3. The improvement of a fine trait in traditional breeding needs to be made by hybridizing the material carrying the fine trait (i.e., the donor parent) with the material to be improved (i.e., the receptor parent), and then subjecting to 6-8 generation backcrossing and cumbersome background selection, and finally selecting those for subsequent breeding from the offspring that have other traits similar to the receptor's parent, while carrying the fine trait from the donor parent. This process is time-consuming, laborious, and costly, and restricted to accuracy of phenotypic observation, genetic drag effects and other influences, the results obtained are not always consistent with the expected goals. Therefore, a combination of typical methods of traditional breeding and a molecular marker-assisted selection technology is a critical means to improve the fine traits and genotype polymerization efficiency. In the present invention, the hybrid Nongda108 is improved by locating a fine allele with reduced leaf angle in teosinte, in combination with the backcross introduction and the molecular marker-assisted selection technology, and this improvement demonstrates that the excellent natural variation from the teosinte can be utilized in breeding practice and can increase the yield by increasing the plant density of maize. On the other hand, a genetic engineering technique combined with a traditional breeding method can be utilized to produce positive lines carrying RNAi vectors through screening of BAR resistance markers, and obtain inbred lines with reduced leaf angles. The finer alleles obtained by the gene-editing technology can be used to get inbred lines with reduced leaf angles quickly with the aid of the molecular marker-assisted selection technology.

In summary, the present invention broadens the source of elite alleles available in plant breeding, which provides a new idea for obtaining elite alleles; greatly shortens the selection process of elite alleles, which provides the possibility of applying elite alleles; and is capable of quickly and accurately improving or producing superior inbred lines with the aid of the molecular marker-assisted selection technology.

In order to facilitate the understanding of the present invention, the present invention is described below using specific language with reference to certain embodiments. However, it should be understood that these specific embodiments are not intended to limit the scope of the present invention. Any changes and further modifications in the embodiments recited in the present description as well as any further applications of the present invention are generally contemplated by those skilled in the art.

All the test methods in the following examples, unless otherwise specified, are conventional methods. All the reagents and biological materials, unless otherwise specified, can be obtained from commercial sources.

In the following examples, the percentages are all mass percentages unless otherwise specified.

The following examples further illustrate and describe the specific embodiments of the present invention, but the present invention is not limited to the following examples.

EXAMPLES

Example 1 Initial Mapping and Fine Mapping of
ZmRAVL1 Gene

Using a set of RIL populations constructed by backcross-ing and selfing of maize inbred line W22 and ancestor species-Teosinte CIMMYT 8759 (referred to as 8759 herein), the initial mapping of leaf angle QTL was per-formed. The phenotypic values of the leaf angle for leaves above the ear (middle leaf angle) and the flag leaf angle of two years at three sites after Blup were used as the input values of the phenotype for QTL mapping. QTL mapping was performed using R software (Version 3.1. 0), combining 19378 high-density and high-quality molecular markers and using the multi-QTL model in R/qtl. After 1000 permutation tests (significance P=0.01), it was determined that the QTL significance thresholds for the middle leaf angle and the flag leaf angle were both LOD=5.

For the middle leaf angle of maize, a total of 10 QTLs were mapped, of which UPA2 (Compact Plant Architecture 2) located on chromosome 2 had the largest effect. It explained 12.1% of the phenotypic variation. The inventors selected this QTL as the target QTL for further fine mapping. The genetic distance of the two LOD confidence intervals of this QTL is about 1.1 cM, and the physical interval is about 2 Mb (FIGS. 1A and B). The inventors used this confidence interval as the initial mapping interval of UPA2, and then performed the fine-mapping.

Using the HIF family MR0220, which is heterozygous for the initial mapping of the QTL interval and relatively simple and consistent in other genetic backgrounds, a total of 152 effective recombinants (recombinant and exchanged indi-vidual plant) were screened (FIG. 1C). Multiple pairs of molecular markers were developed at different physical locations within the initial mapping interval to identify the recombinant sites of recombinants. A total of 19 effective recombinants, which were recombinant at different physical locations and non-repeated, were screened. The obtained 19 recombinants were planted for F3 generation families. For the progeny, genotyping and significance tests were per-formed on the homozygous recombinants and homozygous non-recombinants within the family using molecular mark-ers M137 and M159 (see the forward and reverse primer sequences below). If the phenotype difference between the two is significant, the candidate gene that controls the UPA2 angle difference is located in the heterozygous segment of the recombinants; and if the phenotype difference between the two is not significant, the candidate gene is located in the homozygous segment. The inventors used these 14 recom-binants to map UPA2 within the range of approximately 110 kb between the molecular markers M148-2 and M152 (see the forward and reverse primer sequences below) (FIG. 1C). From the molecular markers M148-2 to M152, 7 new molecular markers such as M148-5, 149, 150-1, 150-3, 150-6, 150-7 and 151 were continuously developed, and 5 key recombinants were screened. Using these 5 key recom-binants for progeny phenotype identification and signifi-cance tests, UPA2 was finally mapped in a 240 bp non-coding region (FIG. 20B, SEQ ID No: 1), which was located about 9.54 kb upstream of the transcription factor gene encoding B3 domain (FIG. 1D). The B3 domain transcrip-tion factor gene was used as a candidate gene and named ZmRAVL1.

Wherein, the sequence of the 240 bp non-coding region is as follows:

```
UPA2-NIL8759
                                      (SEQ ID No: 1)
ATAGAAGAGAGTGATCACTGTTTTTGTGGTTGTTCAGCTTTTACTATCC

CTGGGAAAAAAAGTGTCAGCAGTAATCTACTTTGAGTAGTGTTTCCATA

GAAAACAAAACTGCGCATGCGCGCGCTGAGTGTGGTCCTTCTCTTTTAA

TTACTACTGCGTGGTGTGTGTGCTGCCAACAGTAGTAACCATCTGGC

ACCTCCCTATATTTTTCAGGAAAAATTAAATGAACTGTACTAATTCA

UPA2-NILW22
                                      (SEQ ID No: 2)
ATAGAAGAGAGTGATCACTGTTTTTGTGGTTGTTCAGCTTTTACTATCC

CTGGGAAAAAAAGTGTCAGCAGTAATCTACTTTGAGTAGTGTTTCCAT

AGAAAACAAAACTGCGCATGCGCGCGCTGAGTGGTCCTTCTCTTTTAAT

TACTACTGTGTGGTGTGTGTGCTGCCAACAGTAGTAACCATCTGGCACC

TCCCTATATTTTTCAGGAAAAATTAAATGAACTGTACTAATTCA
```

The sequence of related molecular markers is as follows:

```
M137-F
                                      (SEQ ID No: 3)
CATCTATCTCTGATACACACATGCAG

M137-R
                                      (SEQ ID No: 4)
ATCAGACACTGCACTGCACA

M159-F
                                      (SEQ ID No: 5)
CTACACCATAGTGTGCTGCTCT

M159-R
                                      (SEQ ID No: 6)
GCAATTTACGAAATTTAAACTGGA

M148-2-F
                                      (SEQ ID No: 7)
GAGCACATCTTATTTTATGACAAACA

M148-2-R
                                      (SEQ ID No: 8)
ATTGCGCTAGCAGGATTCAT

M152-F
                                      (SEQ ID No: 9)
GGATTGCGGAAAGAAAGAACC

M152-R
                                      (SEQ ID No: 10)
AGGCAAACATCTTCAAGTTCACA

M148-5-F
                                      (SEQ ID No: 11)
TTGAGCTCGTACGTGTCTGG

M148-5-R
                                      (SEQ ID No: 12)
TGGCAACACAAACAGTGACA

M149-F
                                      (SEQ ID No: 13)
GTACGTGGCAGAGCTAGACT

M149-R
                                      (SEQ ID No: 14)
CTCGCAGTTGATACCACCC
```

-continued

```
M150-1F
                                (SEQ ID No: 15)
TCCAGAAGACTCGTGCTGAA

M150-1R
                                (SEQ ID No: 16)
CCCACTTCCTGTACGTACGT

M150-3F
                                (SEQ ID No: 17)
CATGTGGGACCGGAATCAGA

M150-3R
                                (SEQ ID No: 18)
ACTTTAGACAGTGACGACCTC

M150-6F
                                (SEQ ID No: 19)
GCTTGCTTCTTCGCCTACAA

M150-6R
                                (SEQ ID No: 20)
CCAGATGGTTACTACTGTTGGC

M150-7F
                                (SEQ ID No: 21)
CCATAGAAAACAAAACTGCGCA

M150-7R
                                (SEQ ID No: 22)
TCCTTCCTCTCCCAACCAAC

M151-F
                                (SEQ ID No: 23)
CGTGCCTTTCTTGCATCATA

M151-R
                                (SEQ ID No: 24)
TTGTCTTGCCATGCTTTCTG
```

Figure 20:
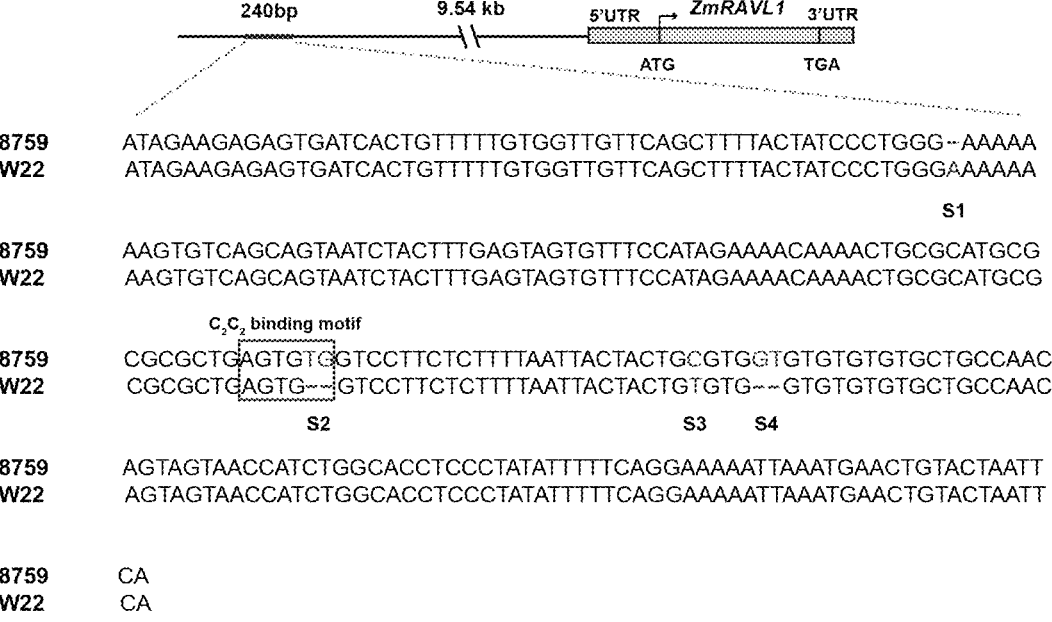
FIG. 20 depicts the nucleic acid sequence alignment at elite interval 240 bp in near-isogenic lines UPA2-NIL$^{W22}$ and UPA2-NIL$^{8759}$, in which (A) shows a mode pattern from the elite interval 240 bp to gene ZmRAVL1. The distance from the 240 bp mapping interval to the start codon of the downstream gene ZmRAVL1 is 9.54 kb. Pink and grey regions denote exon and noncoding regions of ZmRAVL1, respectively. (B) shows the nucleic acid sequence alignment at mapping interval 240 bp in near-isogenic lines. S1 to S4 denote four sequence variations (marked in red font on a grey background) among near-isogenic lines. Red dashed box denotes $C_2C_2$ binding motif.
Figure 21:
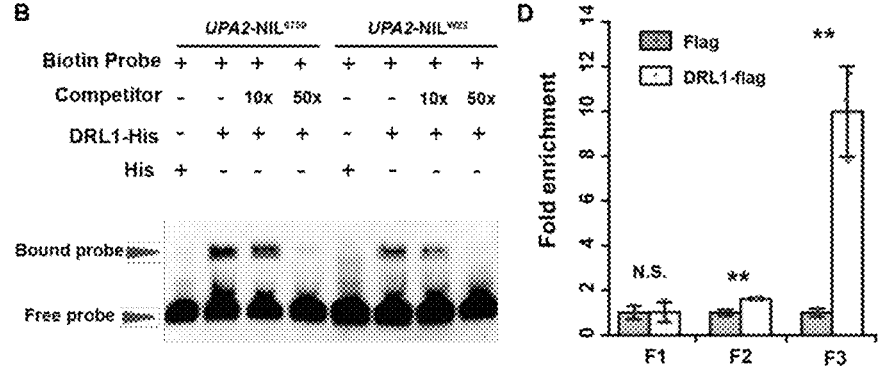
FIG. 21 depicts a sequence adjacent to DRL1 protein binding site S2, in which (A) shows that gel retardation assay shows DRL1 can in vitro bind a sequence adjacent to site S2 and has different capabilities to bind UPA2-NIL$^{W22}$ and UPA2-NIL$^{8759}$; and (B) shows ChIP-qPCR data analysis, indicating that DRL1 can in vivo bind a sequence adjacent to site S2. F3 segment comprises $C_2C_2$ binding motif.
Figure 22:
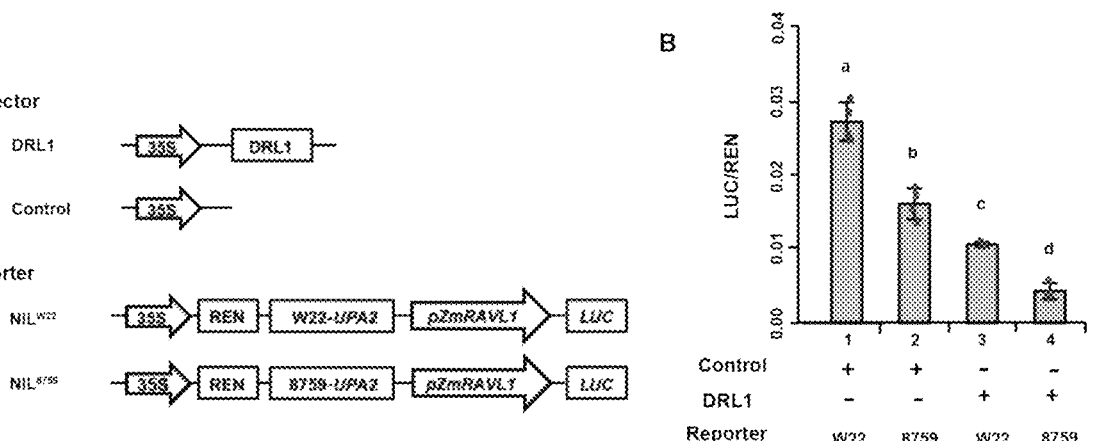
FIG. 22 depicts that the protoplast dual-luciferase reporter assay system verifies that DRL1 protein suppresses downstream gene expression by binding to the S2 site, in which (A) shows a structural chart of vectors for transient expression of maize protoplast. Control indicates an effector-null vector, DRL1 indicates an effector vector of DRL1-linked CDS, UPA2-NIL$^{W22}$ indicates an image of a reporter vector for allele of the maize inbred line W22 without TG insertion, and UPA2-NIL$^{8759}$ indicates an image of a reporter vector for allele of the maize wild-type 8759 with TG insertion. (B) shows a statistical analysis comparison of LUC/REN between combinations of different vectors.

Gene expression is usually regulated by cis-acting elements and trans-acting elements, which mutually interact to jointly regulate the expression level of functional genes. Cis-acting elements refer to specific DNA sequences connected in series with structural genes and are binding sites for transcription factors. They bind to transcription factors to regulate the precise initiation and transcription efficiency of gene transcription; usually include promoters, enhancers and silencers. Trans-acting elements refer to protein factors that can directly or indirectly recognize or bind to the core sequences of various cis-acting elements and participate in regulating the transcription efficiency of target genes, which mainly include transcription activators and transcription repressors. The 240 bp sequence of the fine mapping interval belongs to the non-coding region, and is upstream of ZmRAVL1. It is speculated that the 240 bp non-coding region may be the cis-acting element of the gene, and the same regulation method has been widely reported in maize (Studer et al. 2011; Hung et al. 2012; Huang et al. 2018). Therefore, ZmRAVL1 was used as a candidate functional gene for regulating leaf angle variation. Through phylogenetic analysis (FIG. 4), it was found that ZmRAVL1 is closely related to the RAVL1 gene in rice, and RAVL1 regulates the phenotypic variation of the leaf angle in rice. Through the prediction of the trans-acting factor binding sites on 240 bp non-coding region, it was found that there is a C2C2 binding domain at the sequence GAGTGTG/— (SEQ ID No: 25) (FIG. 20). Through EMSA, ChIP-qPCR and transient protoplast expression (FIGS. 21 and 22), it was demonstrated that DRL1 binds to C2H2 binding domain and inhibits the expression of downstream genes. Finally, through RNAi, CRISPR/CAS9 and overexpression of the three transgenic vectors, it was demonstrated that ZmRAVL1 is a functional gene that regulates leaf angle variation (FIGS. 10, 11 and 12), and the 240 bp non-coding region contains cis-acting elements that regulate the ZmRAVL1 expression and is a silencer that regulates the ZmRAVL1 transcription.

Example 2 Nucleic Acid Molecule Information of ZmRAVL1

The nucleic acid molecular sequence of ZmRAVL1 is available on maizeGDB (https://www.maizegdb.org/). The genome of maize inbred line B73 and the genome sequences of many other maize inbred lines have been tested. Thus, for nucleic acid sequences only, the sequences of most genes are known, and the sequences of all genes including this gene are available from multiple websites such as maizeGDB. Although the function of this gene can be predicted on maizeGDB and other websites, the function of this gene to regulate the leaf angle of maize was discovered by the inventors for the first time. The materials used in the present invention are the maize inbred line W22 and the wild maize Teosinte 8759. The sequencing of W22 has been completed, and the genome sequence has been released. The sequence of this gene in Teosinte 8759 was obtained by cloning with reference to W22 and B73 genomes. The detailed information is shown in FIG. 2 and SEQ ID No: 26 (B73 reference genome sequence as an example):

(1) Promoter region: 5'UTR upstream;

(2) Gene region: as shown in the genome sequence in FIG. 2, the underlined sequences are the coding region of the genome;

(3) UTR region: the 5'UTR region is the nucleic acid sequence upstream of ATG and marked in red; and the 3'UTR is the nucleic acid sequence downstream of TGA and marked in the red.

Example 3 ZmRAVL1 Protein Molecular Information (1) Protein Coding Sequence

```
(https://www.maizegdb.org/gene_center/gene/GRMZM2G102059)
                                            (SEQ ID No: 27)
MEFASSSSRFSREEDEEEEQEEEEEEEEEASPREIPFMTAAATADTGAAASSSSPSAAASSG

PAAAPRSSDGAGASGSGGGGSDDVQVIEKEHMFDKVVTPSDVGKLNRLVIPKQHAEKY

FPLDAAANEKGQLLSFEDRAGKLWRFRYSYWNSSQSYVMTKGWSRFVKEKRLDAGDT

VSFCRGAGDTARDRLFIDWKRRADSRDPHRMPRLPLPMAPVASPYGPWGGGGGGGAG

GFFMPPAPPATLYEHHRFRQALDFRNINAAAAPARQLLFFGSAGMPPRASMPQQQQPPP
```

```
                         -continued
PPHPPLHSIMLVQPSPAPPTASVPMLLDSVPLVNSPTAASKRVRLFGVNLDNPQPGTSAE

SSQDANALSLRTPGWQRPGPLRFFESPQRGAESSAASSPSSSSSSKREAHSSLDLDL (See FIG. 3)
```

(2) Domains Encoding Proteins (http://smart.embl-heidelberg.de/smart/show_motifs.pl)
Domain prediction of the amino acid sequence encoded by the gene on the Smart website shows that the amino acid sequence encoded by the gene contains a B3 domain (amino acid sequence marked in red in FIG. 3). On the gramene website, this gene is annotated as "B3 domain-containing transcription factor NGA2".

(3) Analysis of Amino Acid Sequences Homologous to the Protein Encoded by this Gene in Maize, Sorghum, Rice and *Arabidopsis*

In maize, sorghum, rice and *Arabidopsis*, homology alignment with the ZmRAVL1 protein sequence was performed. P=lx10-50 was taken as the thresholds, and protein sequences with a higher homology among different crop species were selected for phylogenetic analysis. The detailed protein sequences used are as follows (maize: SEQ ID Nos: 28-33, sorghum: SEQ ID Nos: 34-37, rice: SEQ ID Nos: 38-40, *Arabidopsis*: SEQ ID Nos: 41-44):
Maize:

```
>Zm00001d026005_P001/ABi3-2
                                        (SEQ ID No: 28)
MEFASSSSRFSKEEEEQEEEEDEEVSPREIPFMTAAATAGTGATSSSPSPSAAASASASSS

AAALRSSGGGGGGDDDMEVVEKEHMFDKVVTPSDVGKLNRLVIPKQHAEKYFPLDAA

ANEKGLLLSFEDRAGKLWRFRYSYWNSSQSYVMTKGWSRFVKEKRLDAGDTVSFCRG

AADAARDRLFIDWRKRSADSSRHPHRMLPRLPLHMPPLASPYGYGPWGGGAGGFFVPP

ATLYEHHRFRQALDFRNVSAAAAPARQLLFFGSAGMPPRASIPQQQQPPPPSLHSIMMV

QPSPEATAGLPMLLDSVPLVNSPTAAAKRVRLFGVNLDNPQPGSSAESSHDTNALSLRM

PGWQRPGPLRFFESTPQRGAAGAAAGAESSAASSPSSPSSSKREAHSSVDLDL

>Zm00001d017618_P001/ABi3-16
                                        (SEQ ID No: 29)
MDQFAASGRFSREEEADEEQEDASNSMREISFMPPAAASSSSAAASASASASTSASACA

SGSSSAPFRSASASGDAAGASGSGGPADADAEAEAVEKEHMFDKVVTPSDVGKLNRLV

IPKQYAEKYFPLDAAANEKGLLLSFEDSAGKHWRFRYSYWNSSQSYVMTKGWSRFVK

EKRLVAGDTVSFSRAAAEDARHRLFIDWKRRVDTRGPLRFSGLALPMPLPSSHYGGPHH

YSPWGFGGGGGGGGGFFMPPSPPATLYEHRLRQGLDFRSMTTTYPAPTVGRQLLFFGS

ARMPPHHAPPPQPRPFSLPLHHYTVQPSAAGVTAASRPVLLDSVPVIESPTTAAKRVRLF

GVNLDNNPDGGGEASHQGDALSLQMPGWQQRTPTLRLLELPRHGGESSAASSPSSSSSS

KREARSALDLDL

>Zm00001d010077_P001/ABi3-42
                                        (SEQ ID No: 30)
MEFTTPPPATRSGGGEERAAAEHNQHHQQQHATVEKEHMFDKVVTPSDVGKLNRLVIP

KQHAEKYFPLDAAANEKGLLLSFEDRTGKPWRFRYSYWNSSQSYVMTKGWSRFVKEK

RLDAGDTVSFGRGISEAARDRLFIDWRCRPDPPVVHHQYHHRLPLPSAVVPYAPWAAH
```

-continued

AHHHHYPADGHTEPVTPCLCATLVATEMRASSSQLSLTRSNLSRPPQPRIARVDGAQPR

PSSSPRQP

>Zm00001d027409_P001/ABi3-8

(SEQ ID No: 31)

MEFTAPPPATRSGGGEERAAAEHHQQQQQATVEKEHMFDKVVTPSDVGKLNRLVIPKQ

HAERYFPLDAAANDKGLLLSFEDRAGKPWRFRYSYWNSSQSYVMTKGWSRFVKEKRL

DAGDTVSFGRGVGEAARGRLFIDWRRRPDPPVVHHQYHHHRLPLPSAVVPYAPWAAA

AHAHHHHYPAAGVGAARTTTTTTTTVLHHLPPSPSPLYLDTRRRHVGYDAYGAGTRQL

LFYRPHQQPSTTVMLDSVPVRLPPTPGQHAEPPPPAVASSASKRVRLFGVNLDCAAAAG

SEEENVGGWRTSAPPTQQASSSSSYSSGKARCSLNLDL

>Zm00001d048815_P001

(SEQ ID No: 32)

MEFTTPPPATRSGGGEERAAAEHNQHHQQQHATVEKEHMFDKVVTPSDVGKLNRLVIP

KQHAEKYFPLDAAANEKGLLLSFEDRTGKPWRYRYSYWNSSQSYVMTKGWSRFVKEK

RLDAGDTDSFGRGISEAARGRLFIDWRCRPDPPVVHHQYHHRLPLPSAVVPYAPFLEKD

VALDPTNRSHGERPTFLEKDVALDAARVAAEGAGSDLEVDDDLDRRWEGRISELASLI

>Zm00001d051471_P001

(SEQ ID No: 33)

MDQFAASRRFSRNDGADEEQEDVSNSMREISFMPGAASSSAAASASASGSSCAPFRSAS

ADGAGASGSGGDGDGSGDVEKEHMFDKVVTPSDVGKLNRLVIPKQYAEKYFPLDAAG

NEKGLLLSFEDSDGKHWRFRYSYWNSSQSYVMTKGWSRFVKEKRLVAGDTVSFSRSR

SAAEVVDDARRHRLFIDWKRRGLDTRGPLRFSGLALPMPLASYYGAPHHYSSWGLGGG

GGFFMPPSPPATLYEHRLRQGLDFRGMTTYPALTVGRQLLFFGSPRMPPHHAQPQPRPL

PLPLHHYTMQPSAAGVTAASASRPLVVDVDSVPAIESPTTAAKRVRLFGVNLDNKPLSV

SDGGREASHQSGSGNALLPLPQMPGGWQQRTPTLRLLELPRHGAESSAASSPSSSSSAK

REARSAALDLDL

Sorghum:

>SORBI_3006G190400

(SEQ ID No: 34)

MEFASSSSRFSKEEDEEEEGEEEDEEASPREIPFMTAAAATADTGPAAASSSSPSAAGAS

ASASGSAAALRSGDGAGASGSGGGGGGSDDVEVIEKEHMFDKVVTPSDVGKLNRLVIP

KQHAEKYFPLDAAANEKGLLLSFEDRAGKLWRFRYSYWNSSQSYVMTKGWSRFVKEK

RLDAGDTVSFCRGAGEAARDRLFIDWKRRADSRDPHRMPRLPLPMAPVASPYGLGPW

GGGAGGFFMPPAPPATLYEHHRFRQALDFRNINAAAAPARQLLFFGSQGMPPRASMPL

QQQQPQPQPSLPPPPPPLHSIMMVQPGSPAVTHGLPMVLDSVPLVNSPTAAAKRVRLFG

VNLDNPQQGSSAESSQDANALSLRMPGWQRPGPLRFFESPQRGAAESSAASSPSSSSSSK

REAHSSLDLDL

>SORBI_3004G280500

(SEQ ID No: 35)

MDQFAASGRFSREEEADEEQEDASNSMREISFMPAAAAAGTAPSSSAAASAASTSASAS

AASGSSSAAAPFRSASGDAAGASGSGGGGGAAADVEAVEKEHMFDKVVTPSDVGKLN

RLVIPKQYAEKYFPLDAAANEKGLLLSFEDSAGKHWRFRYSYWNSSQSYVMTKGWSR

FVKEKRLVAGDTVSFSRAAAEDARHRLFIDWKRRVDTRGPLRFSGLALPMPLASHYGP

HHYSPWGFGIGGVGGGGGGGGFFMPPSPPATLYEHRLRQGLDFRSMTNYPAPTVGRQQ

-continued

LLFFGSARMPPHHAPAPQPRPLSLPLHHFTVQPSAAAGVTAASRPVVLDSVPVIESPTTA

AKRVRLFGVNLDNNPLSEPDGGVGEASHQGNALSLQMPGWQQRTTPTLRLLELPRHGA

AESSAASSPSSSSSSKREARSALDLDL

>SORBI_3001G528200_OQU93364
                                              (SEQ ID No: 36)
MEFTAPPTAARSGGGEERAAEHQQQQQQQLAAVEKEHMFDKVVTPSDVGKLNRLVIP

KQHAEKYFPLDAAANEKGLLLSFEDRTGKPWRFRYSYWNSSQSYVMTKGWSRFVKEK

RLDAGDTVSFGRGVGDAARGRLFIDWRRRPDPPVHHQYHHRLPLPSVVPYAPWPHAH

HHHYPAAAAAVGVGVGAGAGAARTTTVLHLPPSPSSLYDPHLRHVGYDAYGAGTRQL

LFYRPLHHQQPSTAVVLDSVPVRLPTTPGQHAEPPAPVVASSASKRVRLFGVNLDCAGS

EEENGGGGGWRTSAPPTPHGLPSPPSSSSSSSSGKARCSLNLDL

>SORBI_3001G528200_EER95618
                                              (SEQ ID No: 37)
MEFTAPPTAARSGGGEERAAEHQQQQQQQLAAVEKEHMFDKVVTPSDVGKLNRLVIP

KQHAEKYFPLDAAANEKGLLLSFEDRTGKPWRFRYSYWNSSQSYVMTKGWSRFVKEK

RLDAGDTVSFGRGVGDAARGRLFIDWRRRPDPPVHHQYHHRLPLPSVVPYAPWPHAH

HHHYPAAAAAVGVGVGAGAGAARTTTVLHLPPSPSSLYDPHLRHVGYDAYGAGTRQL

LFYRPLHHQQPSTAVVLDSVPVRLPTTPGQHAEPPAPVVASSASKRVRLFGVNLDCAGS

EEENGGGGGWRTSAPPTPHGLPSPPSSSSSSSSGKARCSLNLDL

Rice:

>Os02t0683500_01
                                              (SEQ ID No: 38)
MEFTTSSRFSKEEEDEEQDEAGRREIPFMTATAEAAPAPTSSSSSPAHHAASASASASAS

GSSTPFRSDDGAGASGSGGGGGGGGEAEVVEKEHMFDKVVTPSDVGKLNRLVIPKQYA

EKYFPLDAAANEKGLLLNFEDRAGKPWRFRYSYWNSSQSYVMTKGWSRFVKEKRLDA

GDTVSFSRGIGDEAARHRLFIDWKRRADTRDPLRLPRGLPLPMPLTSHYAPWGIGGGGG

FFVQPSPPATLYEHRLRQGLDFRAFNPAAAMGRQVLLFGSARIPPQAPLLARAPSPLHHH

YTLQPSGDGVRAAGSPVVLDSVPVIESPTTAAKRVRLFGVNLDNPHAGGGGGAAAGES

SNHGNALSLQTPAWMRRDPTLRLLELPPHHHHGAESSAASSPSSSSSSSKRDAHSALDLD

L

>RAVL1_Os04t0581400_01
                                              (SEQ ID No: 39)
MEQEQDEEEEEAEASPREIPFMTSAAAAATASSSSPTSVSPSATASAAASTSASGSPFRSS

DGAGASGSGGGGGGEDVEVIEKEHMFDKVVTPSDVGKLNRLVIPKQHAEKYFPLDSAA

NEKGLLLSFEDRTGKLWRFRYSYWNSSQSYVMTKGWSRFVKEKRLDAGDTVSFCRGA

AEATRDRLFIDWKRRADVRDPHRFQRLPLPMTSPYGPWGGGAGASSCRPRRPPRSTSIT

AFARASTSATSTPLCRRGSSSSSAPQGRGFISTRPCHRRRRHLRLLTNSTLRCTTRAP

>Os03t0120900_01
                                              (SEQ ID No: 40)
MEFITPIVRPASAAAGGGEVQESGGRSLAAVEKEHMFDKVVTPSDVGKLNRLVIPKQHA

EKYFPLDAASNEKGLLLSFEDRTGKPWRFRYSYWNSSQSYVMTKGWSRFVKEKRLDA

GDTVSFGRGVGEAARGRLFIDWRRRPDVVAALQPPTHRFAHHLPSSIPFAPWAHHHGH

-continued

GAAAAAAAAAGARFLLPPSSTPIYDHHRRHAHAVGYDAYAAATSRQVLFYRPLPPQQQ

HHPAVVLESVPVRMTAGHAEPPSAPSKRVRLFGVNLDCANSEQDHAGVVGKTAPPPLP

SPPSSSSSSSGKARCSLNLDL

*Arabidopsis*

>AT1G01030.2

(SEQ ID No: 41)

MDLSLAPTTTTSSDQEQDRDQELTSNIGASSSSGPSGNNNNLPMMMIPPPEKEHMFDKV

VTPSDVGKLNRLVIPKQHAERYFPLDSSNNQNGTLLNFQDRNGKMWRFRYSYWNSSQS

YVMTKGWSRFVKEKKLDAGDIVSFQRGIGDESERSKLYIDWRHRPDMSLVQAHQFEYN

SVPIHRGLNIGNHQRSYYNTQRQEFVGYGYGNLAGRCYYTGSPLDHRNIVGSEPLVIDS

VPVVPGRLTPVMLPPLPPPPSTAGKRLRLFGVNMECGNDYNQQEESWLVPRGEIGASSS

SSSALRLNLSTDHDDDNDDGDDGDDDQFAKKGKSSLSLNFNP

>AT2G46870.1_NGA1

(SEQ ID No: 42)

MMTDLSLTRDEDEEEAKPLAEEEGAREVADREHMFDKVVTPSDVGKLNRLVIPKQHAE

RFFPLDSSSNEKGLLLNFEDLTGKSWRFRYSYWNSSQSYVMTKGWSRFVKDKKLDAG

DIVSFQRCVGDSGRDSRLFIDWRRRPKVPDHPHFAAGAMFPRFYSFPSTNYSLYNHQQQ

RHHHSGGGYNYHQIPREFGYGYFVRSVDQRNNPAAAVADPLVIESVPVMMHGRANQE

LVGTAGKRLRLFGVDMECGESGMTNSTEEESSSSGGSLPRGGGGGASSSSFFQLRLGSSS

EDDHFTKKGKSSLSFDLDQ

>AT1G01030.1_NGA3

(SEQ ID No: 43)

MDLSLAPTTTTSSDQEQDRDQELTSNIGASSSSGPSGNNNNLPMMMIPPPEKEHMFDKV

VTPSDVGKLNRLVIPKQHAERYFPLDSSNNQNGTLLNFQDRNGKMWRFRYSYWNSSQS

YVMTKGWSRFVKEKKLDAGDIVSFQRGIGDESERSKLYIDWRHRPDMSLVQAHQFGNF

GFNFNFPTTSQYSNRFHPLPEYNSVPIHRGLNIGNHQRSYYNTQRQEFVGYGYGNLAGR

CYYTGSPLDHRNIVGSEPLVIDSVPVVPGRLTPVMLPPLPPPPSTAGKRLRLFGVNMECG

NDYNQQEESWLVPRGEIGASSSSSSALRLNLSTDHDDDNDDGDDGDDDQFAKKGKSSL

SLNFNP

>AT1G13260.1_RAV1 (the homology alignment threshold value between the
gene encoding protein and ZmRAVL1 protein P = 1X10-27)

(SEQ ID No: 44)

MESSSVDESTTSTGSICETPAITPAKKSSVGNLYRMGSGSSVVLDSENGVEAESRKLPSS

KYKGVVPQPNGRWGAQIYEKHQRVWLGTFNEEDEAARAYDVAVHRFRRRDAVTNFK

DVKMDEDEVDFLNSHSKSEIVDMLRKHTYNEELEQSKRRRNGNGNMTRTLLTSGLSND

GVSTTGFRSAEALFEKAVTPSDVGKLNRLVIPKHHAEKHFPLPSSNVSVKGVLLNFEDV

NGKVWRFRYSYWNSSQSYVLTKGWSRFVKEKNLRAGDVVSFSRSNGQDQQLYIGWKS

RSGSDLDAGRVLRLFGVNISPESSRNDVVGNKRVNDTEMLSLVCSKKQRIFHAS

<sub>60</sub>

The results of the phylogenetic analysis of the above encoded protein are shown in FIG. 4. Phylogenetic analysis showed that the ZmRAVL1 gene in maize is closely related to the cloned RAVL1 in rice (FIG. 4). In rice, RAVL1 regulates the expression of brassinolide (BR) synthesis gene and receptor gene, maintains the balance of BR content in rice, and then regulates the plant architecture of rice. When RAVL1 was overexpressed, the leaf angle of rice increased and the plant architecture was loose; and the leaf angle of mutant ravl1-1/-2 decreased and the plant architecture was compact. In summary, the gene ZmRAVL1 in maize highly homologous to RAVL1 may be involved in the regulation of the variation of the maize leaf angle.

Example 4 Construction of ZmRAVL1 Transgenic Vector

4.1 Construction of RNAi Vector (1) Specific fragments (150-300 bp) in the cDNA region of gene ZmRAVL1 were selected to design primers, and restriction sites were introduced to amplify the sense and antisense fragments, respectively. When amplifying the sense fragment, the BamH I and Nco I restriction sites were introduced at the 5'end of the forward primer and the Spe I restriction site was introduced at the 5' end of the reverse primer. When amplifying the antisense fragment, Bgl II and BstE II were introduced at 5'end of the forward primer and Xba I restriction site was introduced at the 5'end of the reverse primer. Using the cDNA of inbred line B73-329 as a template, the sense and antisense fragments were amplified respectively, and the accuracy of the base sequence of the amplified fragments was tested by sequencing.

RNAi Targeting Sequences:

```
                                  (SEQ ID No: 45)
GGACGAGGAGGAAGAGCAGGAGGAAGAGGAGGAGGAGGAGGAGGCGTCT

CCGCGCGAGATCCCCTTCATGACAGCGGCAGCGACGGCCGACACCGGAG

CCGCCGCCTCCTCGTCCTCGCCTTCCGCGGCGGCCTCATCGGGTCCTGC

TGCTGCCCCCCGCTCGAGCGACGGCGCCGGGGCGTCCGGGAGCGGCGGC

GGCGGGAGCGACGACGTGCAGGTGATCGAGAAGGA
```

Primer Names and Sequences

```
    RNAi-1-F
                                  (SEQ ID No: 46)
    CGGGATCCCCATGGGGACGAGGAGGAAGAGCA

RNAi-1-R
                                  (SEQ ID No: 47)
    GGACTAGTTCCTTCTCGATCACCTGCAC

RNAi-2-F
                                  (SEQ ID No: 48)
    GAAGATCTGGTTACCGGACGAGGAGGAAGAGCA

RNAi-2-R
                                  (SEQ ID No: 49)
    GCTCTAGATCCTTCTCGATCACCTGCAC
```

(2) *E. coli* was used to amplify and propagate the P1022 plasmid, and the Bgl II and Xba I (Takara) double digestion system was used to digest the P1022 plasmid and antisense fragments. The double digestion system was as follows:

| Ingredients | Amount added |
| --- | --- |
| plasmid/DNA fragment | 5 μg |
| Bgl II | 5 μL |
| Xba I | 5 μL |
| 10 × T | 20 μL |
| ddH2O | To 100 μL |

It was incubated for more than 3 hours in a 37° C. water bath.

(3) The digested product was purified using a purification kit (OMEGA), and the antisense fragment was introduced into the P1022 vector using T4 ligase (Takara). The ligation system was as follows:

| Ingredients | Amount added |
| --- | --- |
| double-digested plasmid | 70 ng |
| double digested DNA fragment | 50-100 ng |
| T4 ligase | 1 μL |
| 10 × buffer | 2 μL |
| ddH2O | To 20 μL |

Ligation was conducted at 16° C. for more than 8 hours, preferably overnight.

(4) The constructed P1022 vector containing antisense fragments was transformed into *E. coli* DH5α for amplification and propagation, and a positive single clone was selected for sequencing to verify the accuracy of the base sequence, and the plasmid was extracted for use.

(5) Simultaneously the double digestion system of BamH I and Spe I was used to perform double digestion on the P1022 plasmid containing the reverse fragment, and sense fragment. The digestion system was as follows:

| Ingredients | Amount added |
| --- | --- |
| plasmid/DNA fragment | 5 μg |
| BamH I | 5 μL |
| Spe I | 5 μL |
| 10 × K | 10 μL |
| ddH2O | To 100 μL |

I was incubated for more than 3 hours in a 37° C. water bath.

(6) Similarly, the double-digested product was purified using a purification kit (OMEGA), and the sense fragment was introduced into the P1022 vector using T4 ligase with the same ligation system as above.

(7) After the forward fragment and the reverse fragment were introduced into the P1022 vector, a hairpin structure was formed. The vector was transformed into *E. coli* DH5α for amplification and propagation. A positive single clone was selected for forward and reverse sequencing and identification, and the plasmid was extracted for use.

(8) The Nco I and BstE II (Takara) double digestion system was used to digest the P1022 vector containing the hairpin structure and pCAMBIA3301, and the gel extraction kit (Biotake) was used to extract the hairpin structure fragments digested (about 350 bp fragment) and the double-digested pCAMBIA3301 vector (about 10 kb), respectively. The purification of the excised gel was carried out according to protocol of the Biotake gel extraction kit.

(9) T4 ligase was used to ligate the extracted hairpin structure fragment to the double-digested pCAMBIA3301 vector with the same ligation system as above. The constructed vector was transformed into *Escherichia coli* DH5α for amplification and propagation, and a single clone was selected for sequencing and identification. The plasmid was extracted at −20° C. to prepare for transformation of *Agrobacterium*.

4.2 Construction of Overexpression Vector (1) An amplification primer containing the full length of the ZmRAVL1 gene coding region (CDS) was designed by using the genome of the inbred line W22 as a reference sequence. The cDNA of the inbred line W22 was used as the amplification template, and the amplified product was ligated to pEASY-T1 (Transgene). This plasmid was used as a template to amplify the full-length coding region (CDS) of gene ZmRAVL1. The amplified product was purified using a purification kit (OMEGA). High-fidelity enzymes were used for the above amplifications. The primer names and the sequences are as follows:

```
AP2-3F
                                      (SEQ ID No: 50)
GGCCTCATCGCGGATAGAT

AP2-3R
                                      (SEQ ID No: 51)
TTCGCCAGCTGATCGATCTC overE-1F
                                      (SEQ ID No: 52)
ATGGAGTTCGCGAGCTCTTC overE-1R
                                      (SEQ ID No: 53)
TCACAGATCGAGATCCAAGG
```

(2) Xcm1 (NEB) was used to digest vector pBCXUN. The digestion system was as follows:

| Ingredients | Amount added |
| --- | --- |
| plasmid | 800 ng |
| Xcm1 | 0.5 μL |
| Spe1 | 5 μL |
| NEB buffer 2 | 2.5 μL |
| distilled water | To 25 μL |

It was digested at 37° C. for 6 hours, and inactivated at 65° C. for 20 minutes before use.

(3) The purified fragment was ligated to the digested vector pBCXUN. The ligation system was as follows:

| Ingredients | Amount added |
| --- | --- |
| fragment | 100 ng |
| digested vector | 0.7 μL |
| solution I | 2.5 μL |
| total volume | 5 μL |

It was ligated overnight at 16° C.

(4) The ligated vector was transformed into *E. coli* DH5α for amplification and propagation. The positive single clone was selected for sequencing and identification. The plasmid was extracted by the plasmid extraction kit (TIANGEN) for transformation of *Agrobacterium*.

4.3 Construction of Cas9 Vector (1) The targets were screened. The website http://crispr.hzau.edu.cn/CRISPR2/ was used to design the target site of the ZmRAVL1 gene. The principle mainly includes that the target site is located on the gene CDS and is as close as possible to the start codon ATG, the target site is highly specific and has a low off-target rate, the target site is evaluated to bind to the target sequence with a high efficiency, and preferably the target site has a CG content of 55%-60%. After analysis, the nucleic acid sequence of CTCTTCGAGTAGGTTTTCC (SEQ ID No: 54) at 11 bp after ATG was determined to be the gRNA.

(2) The primers were annealed to synthesize double strands. When synthesizing the target, the sequence GGCG (SEQ ID No: 55) was added at the 5' end of the forward primer and the sequence AAAC (SEQ ID No: 56) was added at the 5' end of the reverse complementary primer. 5 μL of the forward primer and reverse primer were added, respectively, forming a system of 10 μL in total. The annealing conditions are as follows:

Denaturation 95° C. 10 minutes
Annealing (Tm value minus 3-5)° C. 10 minutes, slope (R) is 3-5%
Incubation 16° C.

Primer Names and Sequences

```
B3-cas9-F
                                      (SEQ ID No: 57)
GCTCTTCGAGTAGGTTTTCC B3-cas9-R
                                      (SEQ ID No: 58)
GGAAAACCTACTCGAAGAGC
```

(3) Vector pBUE411 was digested. The digestion system was as follows:

| Ingredients | Amount added |
| --- | --- |
| pBUE411 | 1 μg |
| Bsa1HF | 1 μL |
| cutsmart | 5 μL |
| ddH20 | To 50 μL |

The digestion was conducted under 37° C. water bath conditions for more than 4 hours.

(4) The target was ligated with the vector. The target was introduced to the digested pBUE411 vector by T4 ligase. The ligation system was as follows:

| Ingredients | Amount added |
| --- | --- |
| target fragment | 4.5 μL |
| digested pBUE411 | 0.5 μL |
| T4 ligase | 0.5 μL |
| 10 × T4 ligase buffer | 1 μL |
| ddH20 | to 10 μL |

The ligation was conducted under the condition of 16° C. temperature overnight.

(5) The ligation product was transformed into *E. coli* DH5α. The single clone was selected. Primer TaU3-FD3 and target reverse complementary sequence were used to identify colony PCR. Target sequence was verified by TaU3-FD3 sequencing. The positive single clone was amplified and propagated. The plasmid was extracted for transformation of *Agrobacterium*.

Primer Sequence:

```
TaU3-FD3
                                      (SEQ ID No: 59)
TTAGTCCCACCTCGCCAGTTTACAG
```

4.4 Preparation of Competent *Agrobacterium*

Preparation of YEB Medium (PH=7.0):

| Ingredients | Reagent amount |
| --- | --- |
| Yeast extract | 1.0 g |
| Peptone | 5.0 g |
| Beef extract | 5.0 g |
| Sucrose | 5.0 g |

-continued

| Ingredients | Reagent amount |
| --- | --- |
| Magnesium sulfate | 0.5 g |
| Total volume | 1 L |

Note: For the YEB solid medium, 15 g agar powder was added after adding and dissolving of the above reagents.

Preparation of 50 mg/mL rifampicin stock solution: 1 g of rifampicin was weighed and 20 mL of methanol was added;

(1) The *Agrobacterium* strain EHA105 stored at −80° C. on a YEB solid (containing 0.1 mg/mL rifampicin) plate was streaked and incubated at 28° C. in the dark for 48 hours;

(2) *Agrobacterium* plaques with a regular and smooth morphology and a diameter of 2-3 mm were selected and inoculated into 5 mL YEB liquid medium (containing 0.05 mg/mL rifampicin), and then incubated at 220 rpm in dark on a shaker at 28° C. overnight.

(3) 2 mL of the above cultured product was added to 50 mL YEB liquid medium (containing 0.05 mg/mL rifampicin), and then incubated at 28° C. at 220 rpm. The OD value of the cultured product was between 0.5 and 1.0;

(4) The cultured bacteria were transferred into a centrifuge tube, put on ice to cool, and then centrifuged at 5000 rpm for 5 minutes at 4° C.;

(5) The supernatant after centrifugation was removed. An appropriate amount of pre-chilled 100 mM NaCl was added to resuspend the bacteria. The bacteria were washed and centrifuged at 5000 rpm for 5 minutes at 4° C.;

(6) The supernatant after centrifugation was removed. 1 mL of 20 mM CaCl2) pre-chilled on ice was added to resuspend the bacteria. The bacteria were divided into 50 ml/tube, and frozen in liquid nitrogen at −80° C. until use.

4.5 *Agrobacterium* Transformation (Liquid Nitrogen Quick Freezing Method)

(1) The competent *Agrobacterium* stored at −80° C. was thawed in ice (without repeated freezing and thawing). 1 μg of plasmid was added to 50 μL of competent *Agrobacterium* (operating in an ultra-clean bench), gently shaken to mix, then inserted in ice for 30 minutes ice bath;

(2) After the ice bath, the sample was placed in liquid nitrogen for quick freezing for 5 minutes, and then quickly transferred to a 37° C. water bath for heat shock for 5 minutes, then immediately placed in ice for 2 minutes;

(3) 1 mL of YEB culture medium without antibiotics was added inside the ultra-clean bench, and shaken at 280 rpm in dark for 3-4 hours at 200 rpm;

(4) *Agrobacterium* cells were centrifuged at 5000 rpm for 2 min at room temperature for collection. 900 μL of supernatant was removed, and the remaining supernatant was used to resuspend the cells;

(5) The resuspended and mixed cells were evenly spread on the YEB solid medium containing antibiotics (containing 0.05 mg/mL rifampicin and 0.1 mg/mL kanamycin), and cultured in dark at 28° C. for 48 hours.

4.6 *Agrobacterium*-Mediated Genetic Transformation of Maize Immature Embryos (1) Shaking of the bacteria. The *Agrobacterium* bacterial solution stored at −80° C. was inoculated into 25 mL YEB liquid medium containing antibiotics (0.05 mg/mL rifampicin and 0.1 mg/mL kanamycin), and shaken and cultured at 180 rpm at 28° C. in dark overnight. On the next morning, 10 mL of the overnight cultured bacteria solution was added to 40 mL of YEB liquid medium containing antibiotics (the bacterial solution was diluted at 1:5), and cultured at 28° C. at 180 rpm in dark until about 5 pm. The bacterial solution was divided into 50 mL centrifuge tubes, centrifuged at 4000 rpm for 10 minutes to collect *Agrobacterium* cells. The supernatant was removed, and 25 mL of induction medium was added to resuspend the bacterial cell pellets to OD660=0.1. The cells were cultured by rotation at 180 rpm at 28° C. overnight in dark. On the third morning, the overnight culture was divided into 50 mL centrifuge tubes, centrifuged at 4000 rpm for 10 minutes to collect the bacterial cells. Appropriate amount of infection medium (Inf+200 μM AS) was added till OD660=0.8, divided to 2 mL, and put at 22° C. in a dark incubator for use.

(2) Peeling of the embryo. The top 1 cm or so of the young ears of inbred line B73-329 self-pollinated for 10-13 days was removed, inserted with tweezers on the upper axis, and dipped into a germicidal solution (50% commercial bleach and a drop of Tween20) for 20 minutes. The young ears should be immersed in the sterilization solution, and then washed with sterilized ddH2O three times, or with 70% ethanol for 45-60 seconds, then washed with sterilized water twice. ⅓ of the surface of the grain was cut using a sterilized scalpel, the young embryos was squeezed out using the back of the sterilized scalpel, and young embryos of 1.2-2 mm were selected (to ensure the integrity of the young embryos) and put in the infection medium. The embryo was placed at 22° C. in a dark incubator for use when the volume thereof reached 0.5 mL.

(3) Infection. The young embryos placed in the infection solution were washed upside down. The infecting solution was removed with a pipette, and then added with the fresh infection solution to wash the young embryos for 1-2 times. Finally, the infecting solution was added to immerse the young embryos, followed by heat shock at 45° C. for 5 minutes. The infection solution was removed with a pipette, added with 1.8 mL of the infection medium containing *Agrobacterium*, and gently mixed upside down for several times. The centrifuge tube was kept at room temperature for 30 minutes to complete the infection process. The infection solution was removed without damaging the integrity of the embryo.

(4) Co-cultivation. After the infection was completed, the young embryos were gently transferred to the co-culture medium with a long-handled spoon. The young embryos was evenly separated using the back of the long-handled spoon (be careful not to damage the young embryos). The embryo was turned over so that the bow side faced up using a sterilized small scalpel tip, then sealed and numbered and incubated at 22° C. in dark for 20-24 hours and no more than 24 hours. At this step, it should be noted that the co-culture medium contained AgNO3, and the operation under light should be as fast as possible.

(5) Screening and cultivation. The immature embryos on the co-cultivation medium were transferred to the screening medium with the tip of a sterilized small scalpel. 25 immature embryos were placed evenly on each plate. The injured or incomplete immature embryos were discarded to avoid contamination of the culture medium. The plate was sealed and numbered, and incubated at 30° C. in dark for 2 weeks. The screening medium also contained AgNO3, and the operation under light should be as fast as possible.

(6) Pre-differentiation. The callus in the screening medium was selected and transferred to the pre-differentiation medium with sterilized tweezers. An average of 15 calluses was placed on each plate, wherein un-grown embryos, too small and browned calluses should not be transferred to the pre-differentiation medium. The culture plate was sealed and numbered, and cultured at a temperature of 26° C. and a humidity of 55% under light (light:dark of 16:8) for one week. The culture dish was covered by white gauze during culture.

(7) Differentiation. The well pre-differentiated and greened calluses from the pre-differentiation medium were gently transferred to the differentiation medium. An average of 10 calluses was placed on each culture plate. The culture plate was sealed and numbered, and placed at 26° C. under light for 1-2 months. During the culture, the medium was changed every 2 weeks. In the process of changing the medium, larger seedlings or smaller seedlings could be transferred to the rooting medium. Calluses with dead or brown leaves should be carefully removed. Calluses that were too large could be divided into small pieces with a diameter of about 5 mm.

(8) Rooting. The maize seedlings well differentiated in the differentiation medium were transferred to the rooting medium. A part of the seedlings with roots was placed gently in the rooting medium, covered with a lid, and cultivated under light at 26° C. for 2 weeks. If the seedlings grow well, the next step is transplantation. Discard it if there is no root growth after 20 days.

(9) Transplanting. The seedlings with good growth and rooting were transplanted into the soil and carefully managed in the greenhouse.

Example 5 ZmRAVL1 Functional Verification

5.1 Phenotype Analysis of Near-Isogenic Lines

5.1.1 Analysis of Leaf Angle Variation of Near-Isogenic Lines UPA2-NILW22 and UPA2-NIL8759

Figure 5:
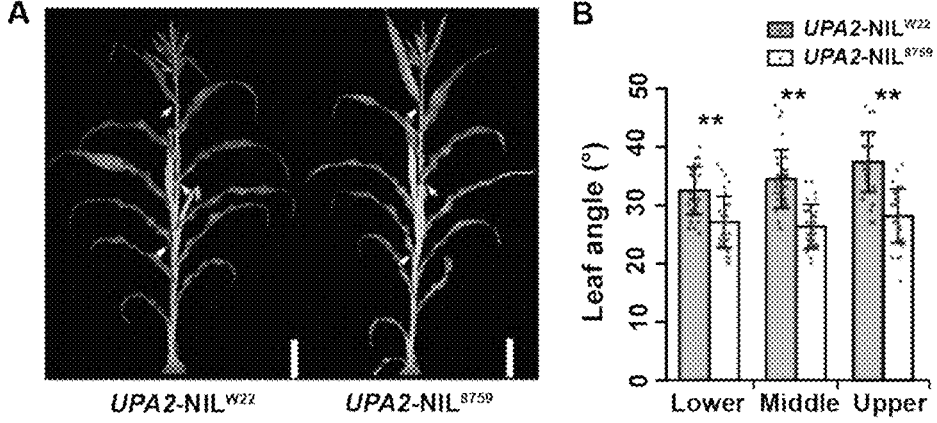
FIG. 5 depicts a comparison between leaf angle phenotypes in near-isogenic lines, in which (A) shows a picture of phenotypes of the whole near-isogenic lines (UPA2-NIL$^{W22}$ and UPA2-NIL$^{8759}$) and (B) shows corresponding statistical data on phenotypes. The white arrows indicate the lower leaf angle (LLA), the middle leaf angle (MLA) and the upper leaf angle (ULA), respectively.

The HIF (Heterogeneous Inbred Family) family MR0220 with relatively homozygous genetic background and heterozygous target segment was screened to construct near-isogenic lines of UPA2, named UPA2-NILW22 and UPA2-NIL8759. By measuring the lower leaf angle (Lower), the middle leaf angle (Middle), and the upper leaf angle (Upper), the difference of the leaf angle of the whole isogenic line was measured (FIG. 5). The results showed that, compared with UPA2-NILW22, UPA2-NIL8759 has decreased lower, middle and upper leaf angles. It means that UPA2 regulates the lower, middle and upper leaf angles.

Figure 6:
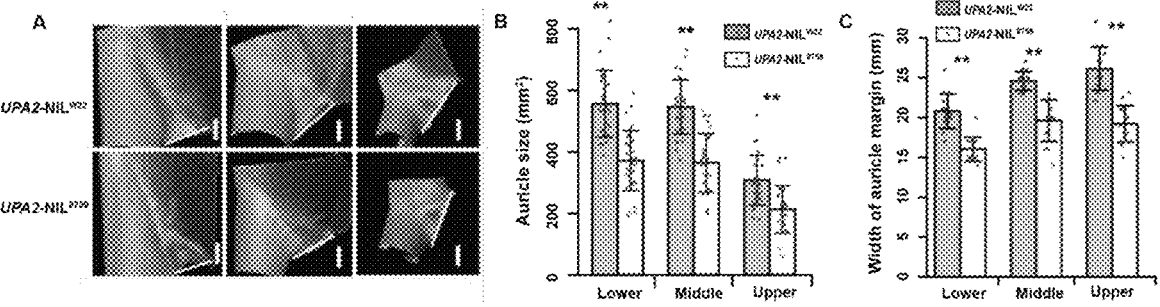
FIG. 6 depicts comparisons between phenotypes of the area of auricles and between phenotypes of the width of auricles at the abaxial sides of the near-isogenic lines, in which (A) shows a picture of mature auricles in lower, upper and flag leaves of the near-isogenic lines; (B) shows phenotypic statistic values of the area of auricles of the near-isogenic lines (UPA2-NIL$^{W22}$ and UPA2-NIL$^{8759}$); and (C) shows a phenotypic comparison between the widths of auricles at the abaxial side of the near-isogenic lines. Data statistical significance values (P values) are all at the top of the column.

5.1.2 Histological and Cytological Analysis of Auricles (1) The Area of Auricles and the Width of Auricles at the Adaxial and Abaxial Side In order to study the causes of the difference of the leaf angles between UPA2-NILW22 and UPA2-NIL8759, the inventors measured the area of the auricles and the width of the auricles at the adaxial and abaxial side (FIG. 6). The results showed that the area of the auricles of the lower, middle, upper leaves of UPA2-NIL8759 were significantly smaller than that of UPA2-NILW22.

At the same time, although there was no significant difference in the width of the auricles at the adaxial axis of the lower, middle, upper leaves of UPA2-NIL8759, the width of the auricles at the abaxial axis was significantly smaller than that of UPA2-NILW22. This indicates that the difference in leaf angle between near-isogenic lines is partly caused by the size of the auricles, and is positively correlated with the width of the auricles at the abaxial side.

(2) Scanning Electron Microscope of Auricle Margin Cells at Abaxial Side

Figure 7:
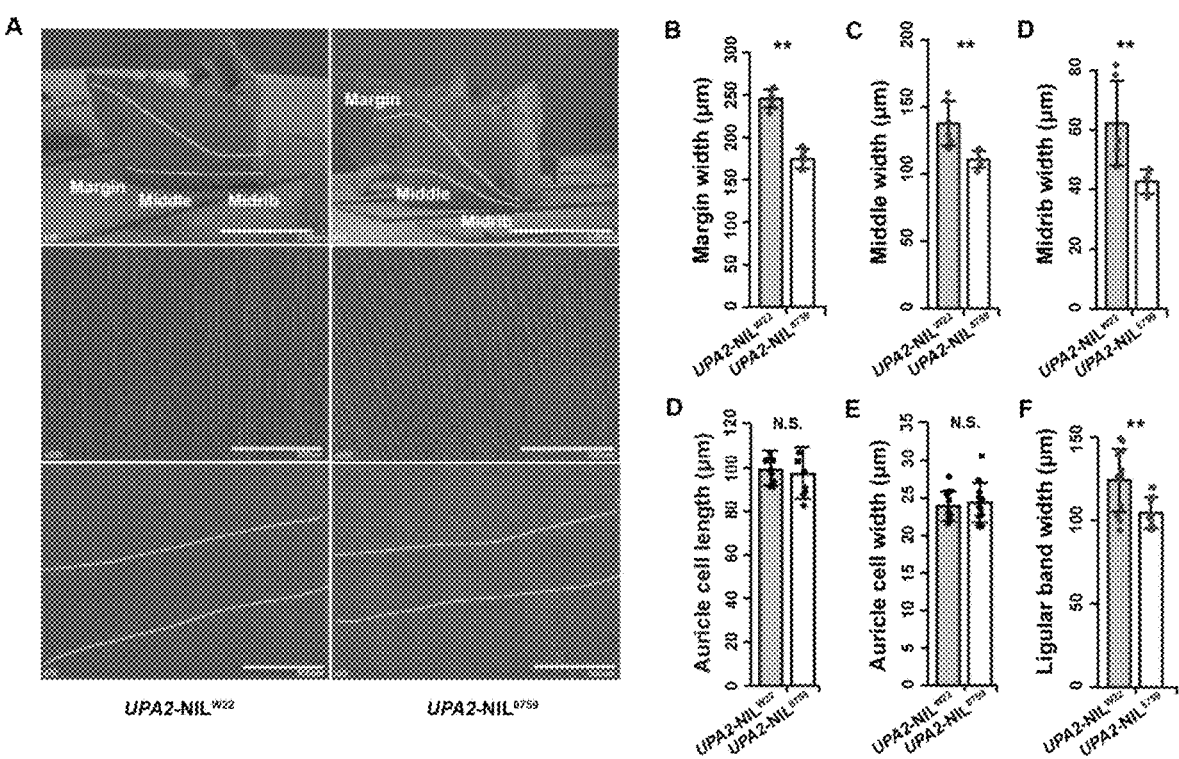
FIG. 7 depicts scanning electron microscopy of the mature auricles and ligules and the immature ligular bands of the UPA2-NIL$^{W22}$ and UPA2-NIL$^{8759}$, in which (A) shows scanning electron microscopy (left) of mature auricles of the UPA2-NIL$^{W22}$ and UPA2-NIL$^{8759}$, and statistical analysis of data on length and width of auricle cells (right), where the red box indicates the region to be scanned in the next picture, scale bars, 3 mm (top) and 200 m (bottom); and (B) shows scanning electron microscopy (left) of mature ligules and immature ligular bands of the UPA2-NIL$^{W22}$ (left) and UPA2-NIL$^{8759}$ (right), and a statistical analysis of data on immature ligular bands (right), where the yellow lines and red arrows indicate width of ligular bands, scale bars, 3 mm (top) and 200 m (bottom).

At V2 stage, the ligule regions of mature leaf (L2) and developing leaf (L4) of near-isogenic lines UPA2-NIL$^{W22}$ and UPA2-NIL$^{8759}$ were sampled and fixed. Morphological development characteristics of auricle cells of L2 and L4 were observed using a scanning electron microscope (SEM). The inventors first performed the scanning electron microscope for L2 ligule regions of near-isogenic lines. The result showed that the area of mature auricle and the width of mature auricle of UPA2-NIL$^{W22}$ are remarkably larger than those of UPA2-NIL$^{8759}$. Meanwhile, the front ligular bands of developing leaves were scanned, which exhibited that the width of the front ligular band of UPA2-NIL$^{8759}$ is notably less than that of UPA2-NIL$^{W22}$. The above results indicate a smaller area of auricles of UPA2-NIL$^{8759}$ is caused by a narrower width of the front ligular band (FIG. 7A).

Auricle cells at abaxial sides of ligule regions of mature leaves L2 of near-isogenic lines UPA2-NIL$^{W22}$ and UPA2-NIL$^{8759}$ were scanned to calculate the length and width of the cells, and to count and detect significant differences. It was found that both of the length and width in the near-isogenic lines exhibited no significant differences (FIGS. 7E and 7F). The above results indicate that the difference in size of the mature auricles of the near-isogenic lines is caused by the difference in number of the developed auricle cells due to the difference in width of the front ligular bands, which ultimately shows leaf angle variation of the two lines.

5.1.3 Analyses of the Number of Layers of Adaxial or Abaxial Sclerenchyma Cells and Thickness Thereof Studies have shown that the size of leaf angle can be influenced by the imbalanced development of cells in ligule regions at the adaxial or abaxial side, the development and mechanical strength of mechanical tissues, the formation and size of vascular bundles, and the composition of cell walls (Ning et al. 2011). As such, a histocytological analysis of the cross-sections in the ligule region is of particular significance. The ligule regions of mature leaf L2 (fully expanded leaf) at V2 stage were picked and fixed in a FAA solution (FIG. 8A) to prepare paraffin samples for study on histomorphological and cytomorphological differences in cross-sections of UPA2-NIL$^{W22}$ and UPA2-NIL$^{8759}$.

Figure 8:
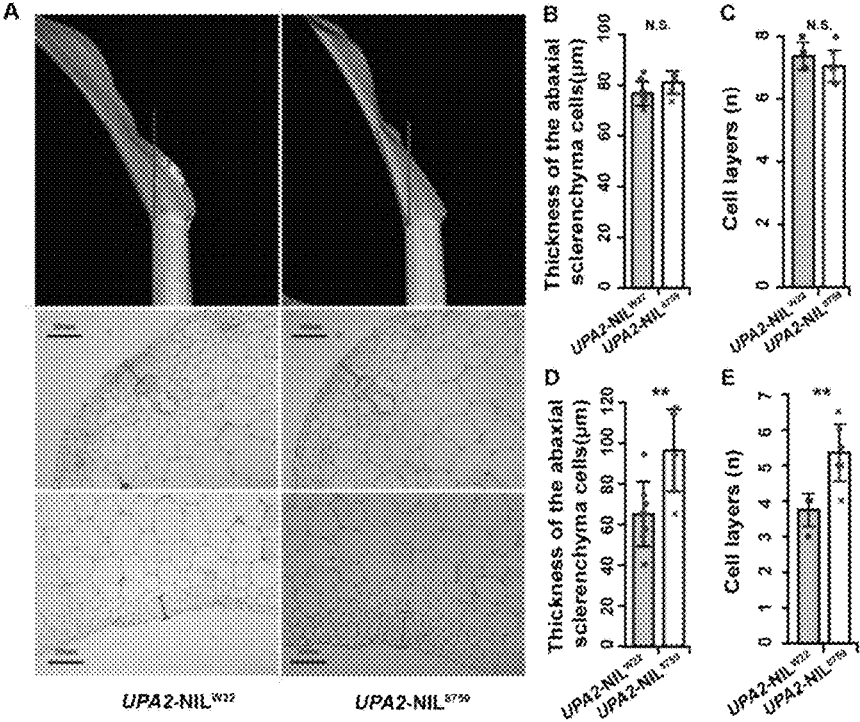
FIG. 8 depicts a morphological comparison between cross-sections of the ligule regions of the near-isogenic lines, in which (A) shows cross-sections of the mature auricle regions of the near-isogenic lines at L2 stage, where the three rows indicate sampling sections of mature auricles of the second leaves (upper), cross-sections at the abaxial side (middle) and cross-sections at the adaxial side (lower), respectively, scale bar 100 m; and (B-E) show phenotypic comparisons between paraffin sections of the near-isogenic lines: (B) thickness of abaxial sclerenchyma cells; (C) number of abaxial sclerenchyma cell layers; (D) thickness of adaxial sclerenchyma cells; and (E) number of adaxial sclerenchyma cell layers.

Paraffin sections of the cross-sections in the ligule regions of UPA2-NIL$^{W22}$ and UPA2-NIL$^{8759}$ were observed under a microscope, and the thickness and the number of layers of adaxial-abaxial sclerenchyma cells were counted (FIG. 8A). The analysis result of the cross-sections in the ligule regions shows that the thickness and the number of layers of abaxial sclerenchyma cells of UPA2-NIL$^{W22}$ and UPA2-NIL$^{8759}$ exhibit no significant differences (FIGS. 8B and 8C), while the thickness and the number of layers of adaxial sclerenchyma cells of UPA2-NIL$^{8759}$ are significantly greater than those of UPA2-NIL$^{W22}$ (FIGS. 8D and 8E). This indicates that the difference in leaf angle of near-isogenic lines UPA2-NIL$^{W22}$ and UPA2-NIL$^{8759}$ is correlated to the thickness and the number of layers of adaxial sclerenchyma cells. On the cross-sections in ligule regions of the both, the more the number of layers of the adaxial sclerenchyma cell, the bigger the thickness thereof and the stronger the support of the vein against the leaf, so that UPA2-NIL$^{8759}$ maintains a smaller leaf angle. The above results indicate that the difference in leaf angles of the near-isogenic lines UPA2-NIL$^{W22}$ and UPA2-NIL$^{8759}$ is partially caused by the number of layers or the thickness of the adaxial sclerenchyma cells in ligule regions.

5.2 Analysis of Expression of Near-Isogenic Lines

At V5 stage, various tissues of the near-isogenic line were sampled, and the sampling parts mainly included blades, ligule regions, and sheaths of a mature leaf (L5) and two immature leaves (L6 and L7) near the mature leaf; a base with three leaves removed; and a root. Besides, a tender tassel of about 1 cm was sampled at V9 stage.

Samples from various tissues were ground, extracted for RNAs, purified and reverse transcribed to obtain cDNAs. Thereafter, a real-time quantitative polymerase chain reaction (RT-qPCR) was performed to analyze expression of ZmRAVL1 among near-isogenic lines. The result shows that near-isogenic line ZmRAVL1 is expressed in various tissues at different stages, and its expression level in mature tissues is higher than that in immature tissues (FIG. 9), which indicates ZmRAVL1 is a broadly expressed gene and has no tissue specificity. The ZmRAVL1 expressions between the near-isogenic lines UPA2-NIL$^{W22}$ and UPA2-NIL$^{8759}$ were compared, and the ZmRAVL1 expression was found to exhibit significant differences in immature leaves (L6 and L7), but exhibit no significant difference in fully mature leaf (L5). In addition, ZmRAVL1 exhibited approximately twice the expression difference in the roots of near-isogenic lines, and exhibited no significant differences in the other tissues.

The above results indicate that ZmRAVL1 is expressed in various tissues of maize and expressed in a high level in mature tissues (such as mature blades). The difference in ZmRAVL1 expression between near-isogenic lines is mainly reflected in immature blades, and its expression level in UPA2-NIL$^{W22}$ is significantly higher than that in UPA2-NIL$^{8759}$.

5.3 Expression or Edition and Phenotype Analysis of Transgenic Lines

5.3.1 Expression and Phenotype Analysis of RNAi Transgenic Lines

At V5 stage, ligule regions of leaves L7 of the positive plant and the negative control in two RNAi transgenic events were sampled according to the sampling method for NILs to test the expression levels of ZmRAVL1. The test result shows that ZmRAVL1 exhibits a significantly lower expression level in the positive plant than that in the negative control in both events (FIG. 10B).

After the tassels and female ears of maize were fully developed and the leaf angles were fixed (about 15 days after pollination), the leaf angles at three leaf positions of the positive plant and the negative control in the two RNAi transgenic events were measured. As shown in FIG. 10, after the transcription level of ZmRAVL1 was interfered, the plant architecture of the entire maize became compact. The statistical analysis of the measured data showed that all leaf angles in lower, middle and upper leaves of the two interference lines ZmRAVL1-RNAi #1 and ZmRAVL1-RNAi #2 were significantly smaller than those of the negative control. This result indicates that a reduction in the expression level of gene ZmRAVL1 can reduce the leaf angle of maize and make the maize plant compact. The above result indicates that ZmRAVL1 is involved in the regulation pathway of the leaf angle and can reduce the leaf angle of maize by reducing the ZmRAVL1 expression, so that the plant architecture is compact.

5.3.2 Expression and Phenotype Analysis of Overexpression Transgenic Lines

Changes in expression levels of the overexpression events ZmRAVL1-OE #1 and ZmRAVL1-OE #2 and the negative control at V5 stage were tested. The test results show that, compared with the negative control, ZmRAVL1 exhibits a significant up-regulation in both overexpression transgenic events (FIG. 11B).

Figure 11:
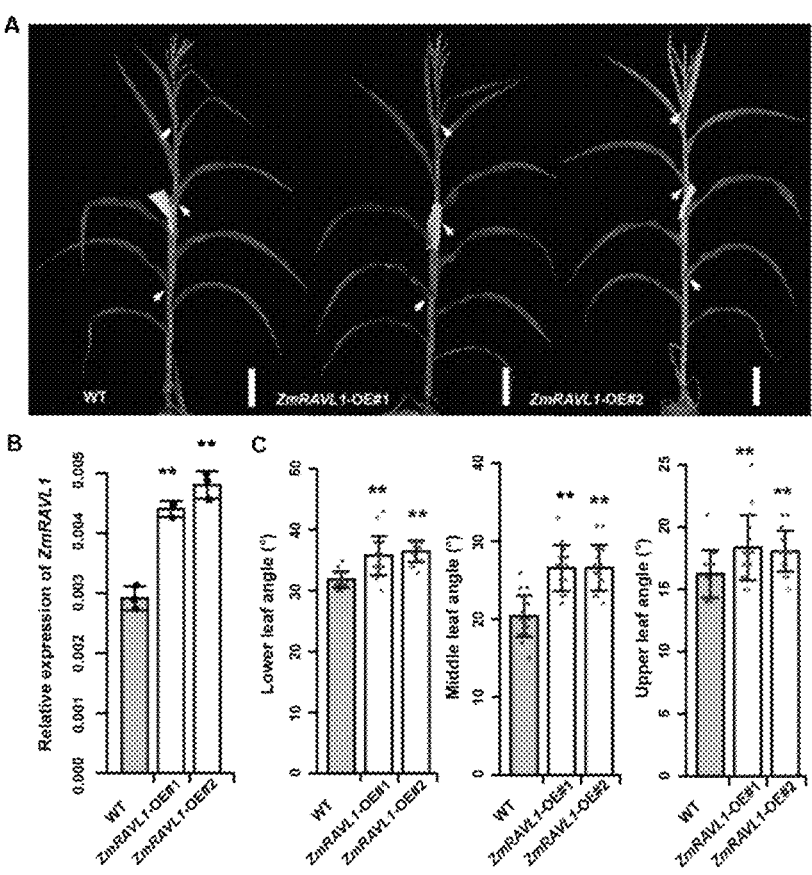
FIG. 11 depicts a phenotype analysis graphic for overexpression transgenic plants, in which (A) is a picture of phenotypes of wild type WT and two whole overexpression transgenic events, where the white arrows indicate the lower leaf angle (LLA), the middle leaf angle (MLA) and the upper leaf angle (ULA), respectively; (B) shows relative expression levels of wild type WT and two overexpression transgenic events ZmRAVL1; and (C) shows a phenotypic statistic comparison between wild type WT and two overexpression transgenic events ZmRAVL1-OE #1 and ZmRAVL1-OE #2. Data statistical significance values (P values) are all at the top of the column.
Figure 12:
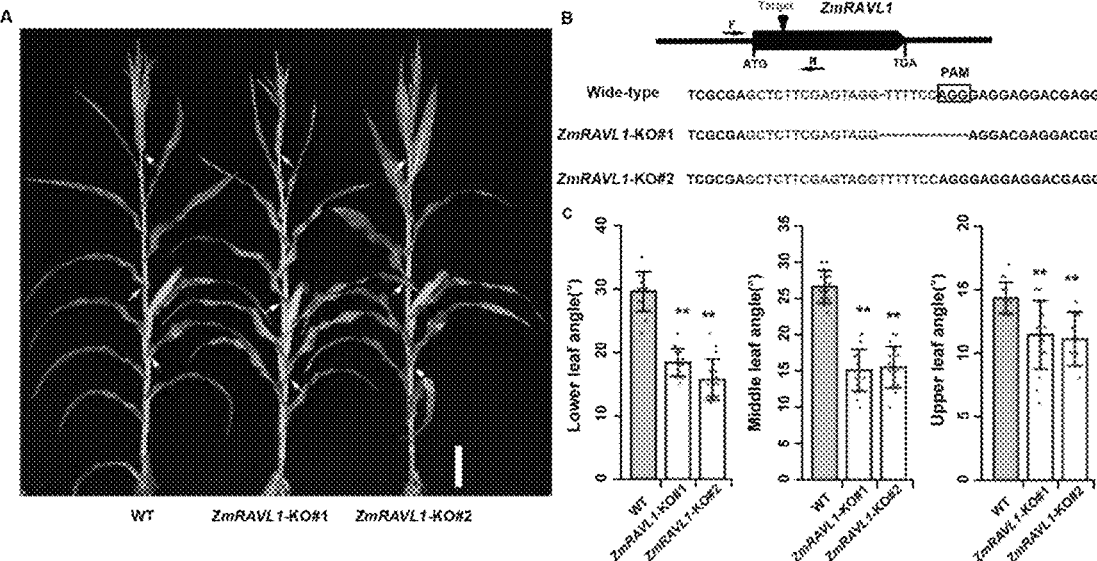
FIG. 12 depicts reduced leaf angles of CRISPR/Cas9 transgenic plants, in which (A) shows a picture of phenotypes of wild type WT and two whole CRISPR/Cas9 transgenic plants, where the white arrows indicate the lower leaf angle (LLA), the middle leaf angle (MLA) and the upper leaf angle (ULA), respectively; (B) shows the ZmRAVL1 genetic structure and the CRISPR/Cas9 cleavage target site located in ZmRAVL1 exon as well as editing of two CRISPR/Cas9 gene knockout events; and (C) shows a phenotypic statistic comparison between WT and two CRISPR/Cas9 transgenic events. Data statistical significance values (P values) are all at the top of the column.

When maize plants were mature and the leaf angles were fixed (about 15 days after pollination), the leaf angle phenotype was measured for the two overexpress transgene-positive events and the negative control (FIG. 11). Statistical analysis of leaf angles at three leaf positions showed that with the up-regulation of the expression level of the ZmRAVL1 gene, the leaf angles of the two positive events ZmRAVL1-OE #1 and ZmRAVL1-OE #2 increased, and thus the overall plant architecture of maize became loose. The above results also indicate that ZmRAVL1 is involved in the regulation pathway of the leaf angle and can increase the leaf angle by up-regulating the ZmRAVL1 expression, so that the plant architecture is loose.

5.3.3 Mutation Site and Phenotype Analysis of ZmRAVL1 Edited with CRISPR/Cas9 Technique The CDS region of ZmRAVL1 was edited with the CRISPR/Cas9 technique to obtain seven T1 generation transgenic events. In T2 generation plant lines, primers cas9-F and cas9-R were designed at flank of the target site to amplify the genomic DNA of the T2 plant lines and a single plant was sequenced. The sequencing results showed that sequencing single-peak plants occurred in two events. Sequence alignment of the target segments with the wild type revealed that these two plant lines were homozygous mutants with 14 bp deletion and single base insertion, respectively. Single-peak plants of the two lines were selfed to obtain two independent transgenic events with homozygous mutations. The two homozygous mutants obtained by gene editing were named ZmRAVL1-KO #1 and ZmRAVL1-KO #2, respectively (FIGS. 12A and 12B).

The two homozygous mutants ZmRAVL1-KO #1 and ZmRAVL1-KO #2 were planted in the field together with a negative control. After the plants were mature and the leaf angles were fixed (namely, about 15-20 days after pollination), a phenotypic investigation was performed. Data analysis showed that the lower leaf angle, middle leaf angle, and upper leaf angle of both ZmRAVL1-KO #1 and ZmRAVL1-KO #2 were all significantly smaller than those of the wild type (FIG. 12C). The above results indicate that ZmRAVL1 is an important gene regulating leaf angle variation, and its loss of function can significantly reduce the leaf angle of the whole plant.

Primer Sequences and Names:

cas9-F (SEQ ID No: 60)

CAGCCAGCTAGTCAGTCTCC,

-continued cas9-R (SEQ ID No: 61)

TGTCATGAAGGGGATCTCGC.

Figure 13:
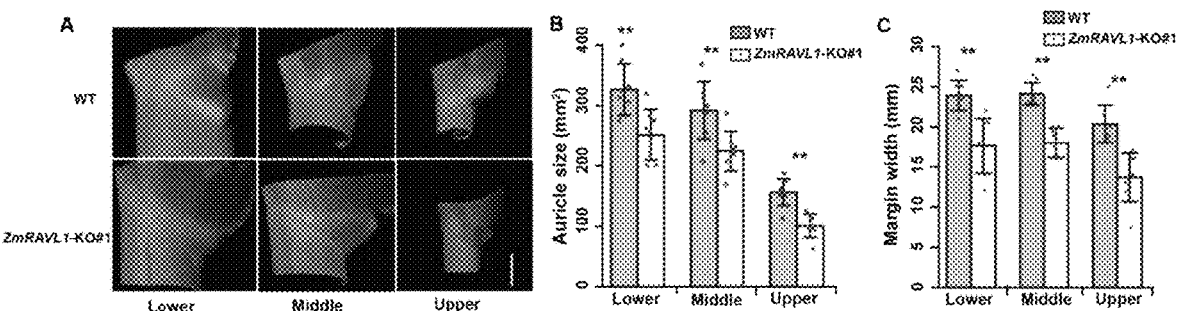
FIG. 13 depicts comparisons between phenotypes of the area of auricles and between phenotypes of the width of auricles at the abaxial sides of mature plants in wild-type WT and CRISPR/Cas9 knockout lines, in which (A) shows mature auricle regions in the upper, middle and lower leaves of wild-type WT and CRISPR/Cas9 knockout lines, scale bar, 1 cm; (B) shows a comparison between phenotypic values of the area of auricles of wild-type WT and CRISPR/Cas9 knockout lines; and (C) shows a phenotypic statistic analysis of width of auricles at the abaxial sides of abaxial leaves in near-isogenic lines.

5.3.4 Histological and Cytological Analyses of Auricle Regions of ZmRAVL1-KO #1 and WT (1) Analysis of the Area of Auricles and the Width of Adaxial-Abaxial Auricles The areas of auricles and the widths of adaxial-abaxial auricles of ZmRAVL1-KO #1 and WT were measured (FIG. 13). The results show that the area of auricles and the width of adaxial-abaxial auricles of the lower leaves, upper leaves and flag leaves of ZmRAVL1-KO #1 are significantly smaller than those of WT. The result proves that ZmRAVL1-KO #1 controls the size of the leaf angle by adjusting the area of auricles.

Figure 14:
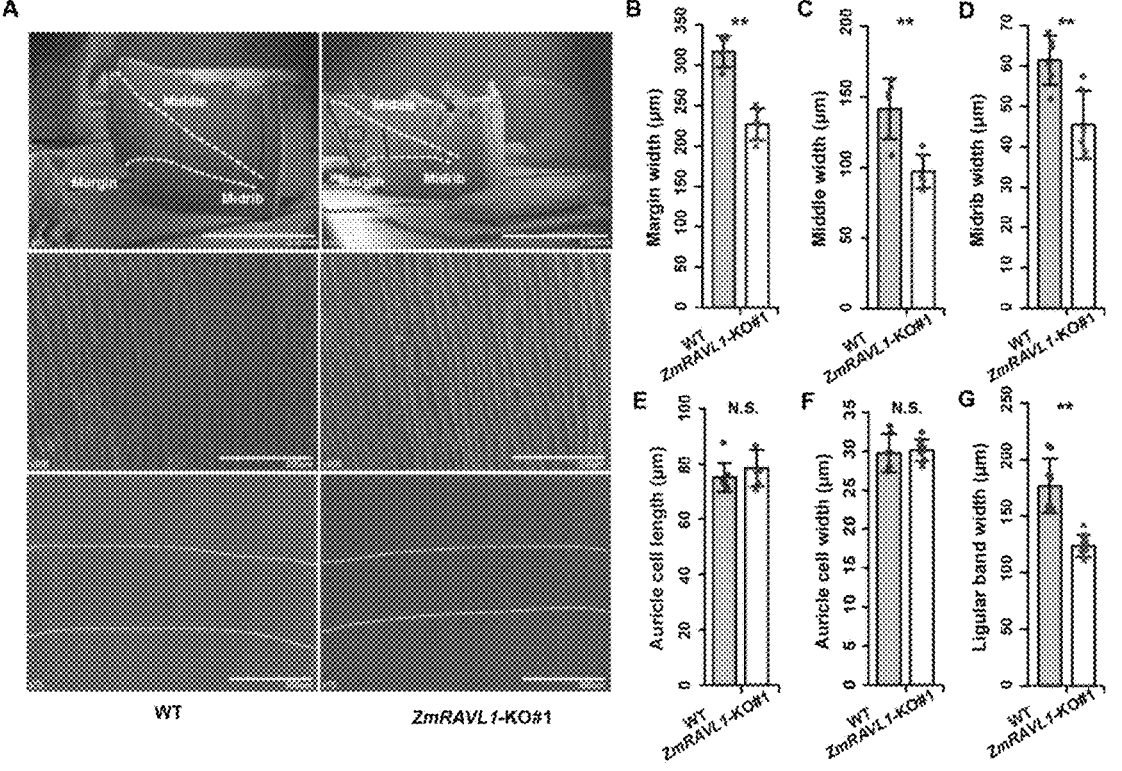
FIG. 14 depicts a scanning electron microscopy analysis of mature auricles and ligules and immature ligular bands of CRISPR/Cas9 transgenic plants, in which (A) shows scanning electron microscopy (top) and cellular morphology (middle) of mature auricles and immature ligular bands (bottom) of wild-type WT and CRISPR/Cas9 transgenic event 1 (ZmRAVL1-KO #1), where the red boxes in the top pictures indicate the regions to be scanned in the middle pictures, scale bars, 3 mm (top), 200 μm (middle) and 500 μm (bottom); (B-G) show phenotypic comparisons of mature auricle regions and immature ligular bands of wild-type WT and CRISPR/Cas9 transgenic event 1 (ZmRAVL1-KO #1); (B) shows outer margin width of mature auricles; (C) shows middle width of mature auricle; (D) shows inner margin width of mature auricles; (E, F) show length and width of cells in the mature auricle region; and (G) shows width of the immature ligular band.

(2) Scanning Electron Microscopy Analysis of Auricle Margin Cells at the Abaxial Side Scanning electron microscopy was performed on auricles of mature leaves L2 and front ligule bands of immature leaves L4 of ZmRAVL1-KO #1 and WT (FIG. 14A). The result shows that the width of the auricle of the mature leaf L2 (FIGS. 14B, 14C and 14D) and the width of the front ligule band of L4 of ZmRAVL1-KO #1 are significantly smaller than those of WT (FIG. 14G), which indicates that the smaller area of the auricle of ZmRAVL1-KO #1 is caused by a narrower width of the front ligule band.

Statistical detection of the lengths and widths of the abaxial auricle cells of mature leaves L2 of ZmRAVL1-KO #1 and WT revealed no significant difference between them (FIGS. 14E and 14F). The above results demonstrate that ZmRAVL1-1 affects the number of cells that are developed into auricles by regulating the width of the front ligular band, which eventually leads to the difference in the area of auricles and thus shows the leaf angle variation.

Figure 15:
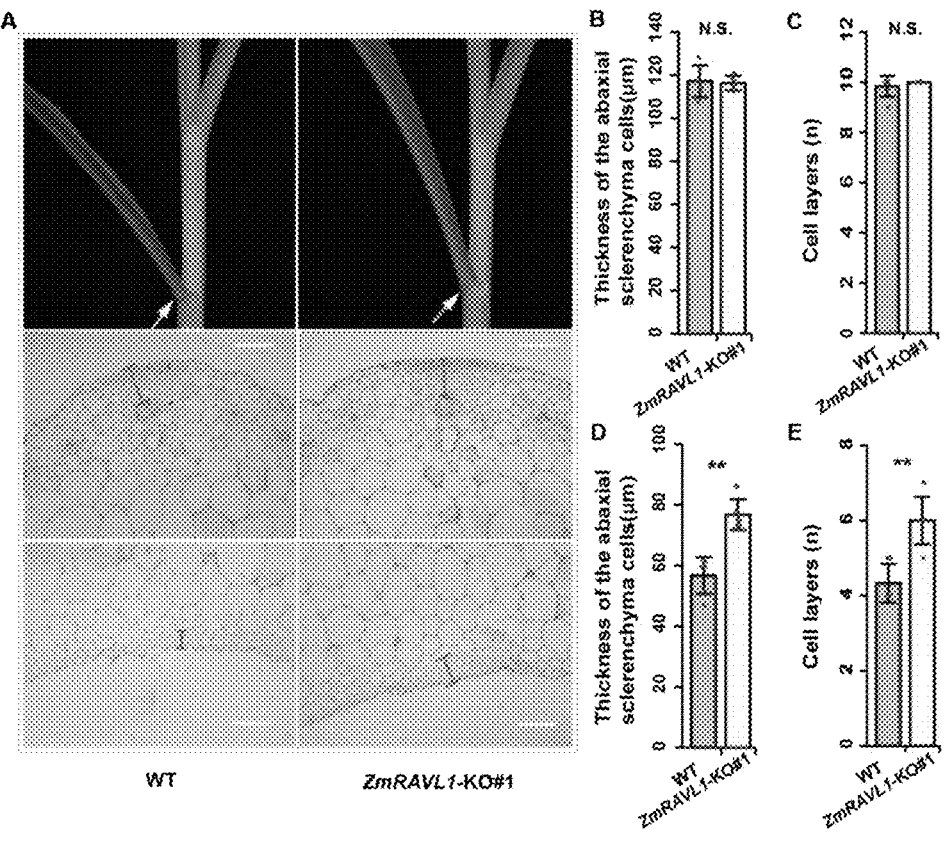
FIG. 15 depicts a morphological analysis of cross-sections in the ligule regions of wild type and CRISPR/Cas9 transgenic positive plant, in which (A) shows cross-sections in the mature ligule regions of wild type and CRISPR/Cas9 transgenic positive plant at L2 stage, where the three rows indicate sampling sections of mature auricles of the second leaves (upper), cross-sections at the abaxial side (middle) and cross-sections at the adaxial side (lower), respectively, scale bar 100 m; and (B-E) show phenotypic comparisons between paraffin sections of the near-isogenic lines: (B) thickness of abaxial sclerenchyma cells; (C) number of abaxial sclerenchyma cell layers; (D) thickness of adaxial sclerenchyma cells; and (E) number of adaxial sclerenchyma cell layers.

(3) Analyses of the Number of Adaxial or Abaxial Sclerenchyma Cell Layers and Thickness Thereof Thicknesses and the numbers of layers of adaxial or abaxial sclerenchyma cells of the cross-sections in the ligule regions of mature leaves of ZmRAVL1-KO #1 and WT at V2 stage were calculated. Statistical data show (FIG. 15) that ZmRAVL1-KO #1 and WT are not significantly different in both the thickness and the number of layers of abaxial sclerenchyma cells, but the thickness and the number of layers of adaxial sclerenchyma cells of ZmRAVL1-KO #1 are significantly greater than those of WT. The above results demonstrate that ZmRAVL1 enhances the support strength of a vein against a blade by regulating the number of layers or thickness of the adaxial sclerenchyma cells, thereby exhibiting a smaller leaf angle and keeping the plant architecture compact.

5.4 Analysis of Gene Effect on Construction of F1 Hybrids

5.4.1 Construction of an F1 Test Hybrid Crossed by ZmRAVL1-KO #1 or ZmRAVL1-RNAi #1 and WT with a Superior Inbred Line In order to verify the potential use of ZmRAVL1 in genetic engineering breeding, the homozygous positive line ZmRAVL1-KO #1 carrying a CRISPR/Cas9 vector and wild-type WT were crossed with a plurality of superior inbred lines (HC, Xu178, C7-2, Z58, PH4CV and PH6WC), respectively to construct F1 test hybrids. In the same way, F1 test hybrids were constructed using an RNAi homozygous positive line ZmRAVL1-RNAi #1 and wild-type WT, respectively.

(1) Analysis of the Difference in Leaf Angle of F1 Test Hybrid

Figure 16:
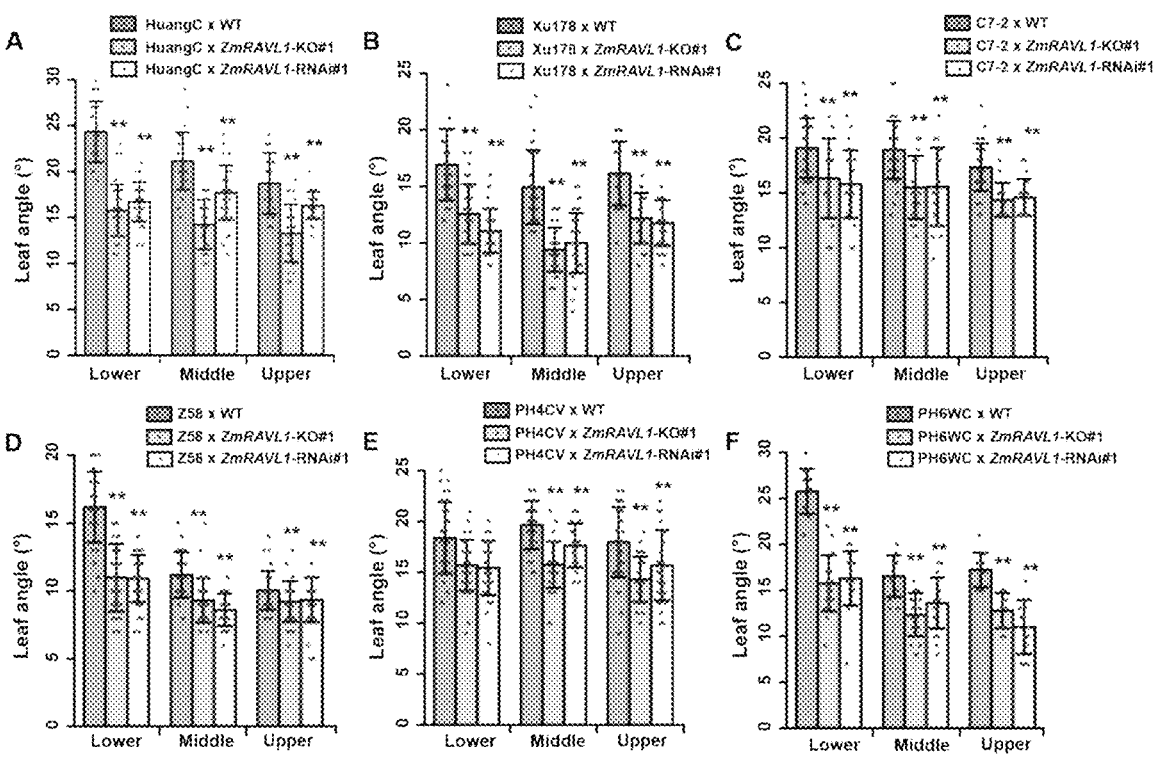
FIG. 16 depicts construction of an F1 test hybrid crossed by ZmRAVL1-KO #1 or ZmRAVL1-RNAi #1 and WT with an inbred line, in which the wild-type is a ZmRAVL1-KO #1 or ZmRAVL1-RNAi #1 transgenic receptor material.

Leaf angles in the lower leaf, middle leaf and upper leaf of the F1 test hybrid were measured. Data analysis shows (FIG. 16) that the leaf angles in the lower leaf, middle leaf and upper leaf of the F1 test hybrid crossed by an inbred line with ZmRAVL1-KO #1 or ZmRAVL1-RNAi #1 are significantly smaller than the leaf angles at the three leaf positions of the F1 hybrid crossed by an inbred line with WT. The above result indicates that in genetic engineering breeding, the combination of backcrossing improvement and transgenic technology can reduce the leaf angle of a hybrid parent by reducing the expression level of ZmRAVL1 or making ZmRAVL1 dysfunctional, thereby cultivating compact hybrids and increasing the maize plant density per unit area.

5.5 Plot Trials for Yields of ZmRAVL1-KO #1 and WT

5.5.1 TL Plot Trial in 2008

(1) Design of Plot Experiments

Figure 17:
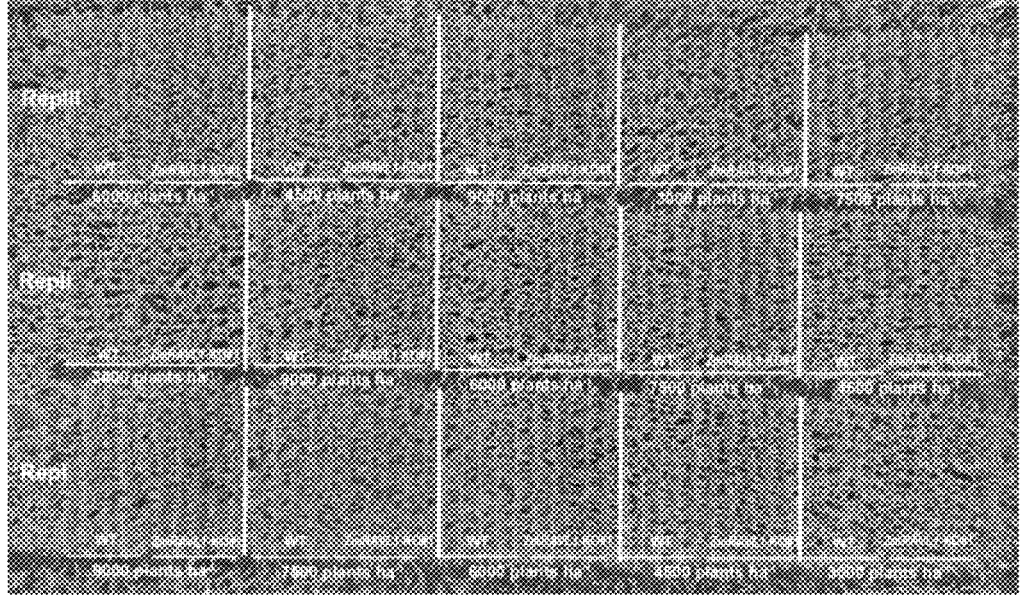
FIG. 17 depicts a dense planting and high yielding plot distribution of ZmRAVL1-KO #1 and WT (Tieling, Liaoning Province, in 2008).

In the spring of 2018, dense planting and high-yield experiments of ZmRAVL1-KO #1 and WT were conducted in Tieling County, Tieling City, Liaoning Province, China. The experiments followed a split-plot design with biological replications in main plots and different plant densities and genotypes in subplots. Three biological replications were designed, and each of them consisted of 5 densities of 3,000, 4,500, 6,000, 7,500 and 9,000 plants/mu; 5 rows of ZmRAVL1-KO #1 and 5 rows of WT were planted under each density. Each row was 5 m long and spaced 0.5 m (FIG. 17). During each maize growth period, the same and consistent field management measures, and unified fertilization application, weed control, and pest control were implemented for different replications. Maize was pollinated in a naturally open state without any artificial supplementary pollination. Maize was harvested when maize kernels were physiologically matured, and the middle three rows were harvested for each genotype for seed and yield tests.

(2) Analysis of Plot Ear Traits and Yield Factors in CAS9 Plot

Figure 18:
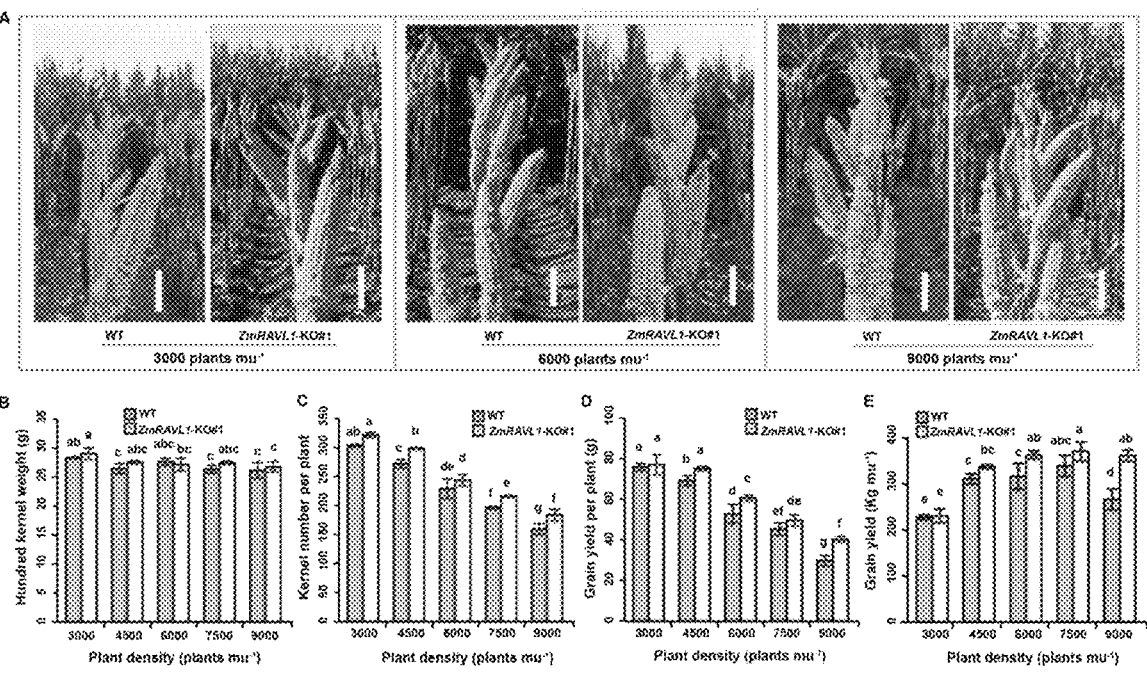
FIG. 18 depicts a dense planting and high yielding plot trial of ZmRAVL1-KO #1 and WT (Tieling, Liaoning Province, in 2008), in which (A) shows harvested maize ears of ZmRAVL1-KO #1 and wild-type under different plant densities in Tieling in 2018, scale bar 4 cm; and (B-E) show comparisons of phenotypes of ZmRAVL1-KO #1 and wild-type ear traits under different plant densities: (B) hundred kernel weight; (C) kernel number per plant; (D) grain yield per plant; and (E) grain yield. Values are mean±SD. Different letters denote significant differences (P<0.05).

The harvested ears of maize were fully dried and then subjected to seed test. The main traits to be examined included the hundred kernel weight, the kernel number per ear, the kernel weight per ear and the yield per unit area. The hundred kernel weight refers to the quality of one hundred kernels in the middle of the ear. The kernel number per ear refers to the number of all kernels on the maize ear that have been pollinated and has formed kernel prototype. The kernel weight per ear refers to the quality of all kernels on the maize ear. The yield per unit area refers to the average ear quality in this plot calculated from the ear quality of the three rows for seed test, and then converted to a yield per mu ($M=(m_1+m_2+m_3 \ldots m_n)/n*N$, M: grain yield per mu, $m_n$: weight of single ear, N: number of maize plants per mu). Under the densities of 3,000 and 4,500 plants/mu, there is no significant difference between the per mu yields of ZmRAVL1-KO #1 and WT, while under the densities of 6,000, 7,500 and 9,000 plants/mu, the per mu yield of ZmRAVL1-KO #1 with a smaller leaf angle due to dysfunctional ZmRAVL1 is significantly increased in comparison to WT (FIG. 18). Analysis of the factors affecting the yield reveals that an average yield per plant of maize is a factor of determining the difference in yield per mu, and the kernel number per ear of ZmRAVL1-KO #1 with a smaller leaf angle is significantly greater than that of WT with a larger leaf angle, and there is no significant difference in hundred kernel weight between them. This indicates that the kernel number per ear is a main factor causing the difference in yields between ZmRAVL1-KO #1 and WT. 5.5.2 HN plot trial in 2008

(1) Design of Plot Experiments

In the winter of 2018, dense planting and high-yield experiments of ZmRAVL1-KO #1 and WT were conducted in Nanbin Farm in Sanya City, Hainan Province, China. The experiments followed a split-plot design with biological replications in main plots and different plant densities and genotypes in subplots. Three biological replications were designed, and each of them consisted of 5 densities of 3,000, 4,500, 6,000, 7,500 and 9,000 plants/mu; 5 rows of ZmRAVL1-KO #1 and 5 rows of WT were planted under each density. Each row was 5 m long and spaced 0.5 m (FIG. 17). During each maize growth period, the same and consistent field management measures, and unified fertilization application, weed control, and pest control and the like were implemented for different replications. Maize was pollinated in a naturally open state without any artificial supplementary pollination. Maize was harvested when maize kernels were physiologically matured, and the middle three rows were harvested for each genotype for seed and yield tests.

(2) Analysis of Plot Ear Traits and Yield Factors in CAS9 Plot

Figure 19:
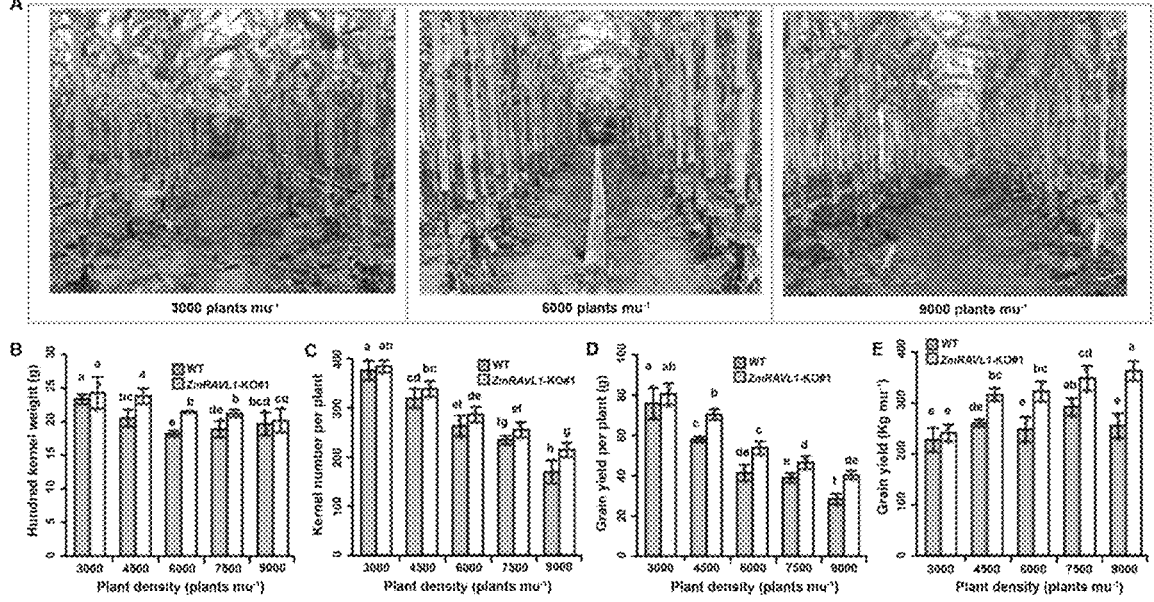
FIG. 19 depicts a dense planting and high yielding plot trial of ZmRAVL1-KO #1 and WT (Sanya, Hainan Province, in 2018), in which (A) shows different plant densities of ZmRAVL1-KO #1 and wild-type maize plants in the field trial in Sanya in 2017; and (B-E) show comparisons of phenotypes of ZmRAVL1-KO #1 and wild-type ear traits under different plant densities: (B) hundred kernel weight; (C) kernel number per plant; (D) grain yield per plant; and (E) grain yield. Values are mean±SD. Different letters denote significant differences (P<0.05).

The harvested ears of maize were fully dried and then subjected to seed test. The main traits to be examined included the hundred kernel weight, the kernel number per ear, the kernel weight per ear and the yield per unit area. The hundred kernel weight refers to the quality of one hundred kernels in the middle of the ear. The kernel number per ear refers to the number of all kernels on the maize ear that have been pollinated and has formed kernel prototype. The kernel weight per ear refers to the quality of all kernels on the maize ear. The yield per unit area refers to the average ear quality in this plot calculated from the ear quality of the three rows for seed test, and then converted to a yield per mu (M=(m₁+m₂+m₃ ... mₙ)/n*N, M: grain yield per mu, mₙ: weight of single ear, N: number of maize plants per mu). Under the density of 3,000 plants/mu, there is no significant difference between the per mu yields of ZmRAVL1-KO #1 and WT, while under the densities of 4,500, 6,000, 7,500 and 9,000 plants/mu, the per mu yield of ZmRAVL1-KO #1 with a smaller leaf angle due to dysfunctional ZmRAVL1 is significantly increased in comparison to wild-type (FIG. 19). Analysis of the factors affecting the yield reveals that an average yield per plant of maize is a factor of determining the difference in yield per mu, and the kernel number per ear of ZmRAVL1-KO #1 with a smaller leaf angle is significantly greater than that of WT with a larger leaf angle, and there is no significant difference in hundred kernel weight therebetween except for those under 6,000 and 7,500 plants/mu. This indicates that the kernel number per ear is a main factor causing the difference in yields between ZmRAVL1-KO #1 and WT.

Example 6 Functional Site Verification 6.1 Analysis of Nucleic Acid Sequence at Elite Interval 240 bp The UPA2 mapping interval was narrowed down to 240 bp noncoding region by elite, and a physical distance from this interval to a downstream gene ZmRAVL1 was about 9.54 kb (FIG. 20A). The nucleic acid sequences at elite interval 240 bp were aligned between near-isogenic lines UPA2-NIL^{W22} and UPA2-NIL^{8759}. The sequence alignment revealed base variation of one 1 bp, and insertion and deletion of three 1-2 bps, and the four polymorphism sites were designated as S1, S2, S3 and S4, respectively (FIG. 20B).

6.2 Function Verification of S2 Site

The PPAN2.0 software was used to predict the motifs of the upstream transcription factor binding sites for the four variation sites and partial flanking sequences of the mapping interval of 240 bp. The prediction results showed that the binding motifs of UPA2-NIL^{W22} and UPA2-NIL^{8759} were different only at the mutation site S2, and no differential protein binding motifs were predicted at the other three mutation sites. Further analysis revealed that there was a C2C2 transcription factor binding site (GAGTGTG (SEQ ID No: 25)) in the vicinity of the TG insertion allele carried by UPA2-NIL^{8759}, while no consistent protein binding motif was predicted in the corresponding nucleic acid sequence of UPA2-NIL^{W22} (FIG. 20B). Recently, Strable et al. (2017) cloned two genes DRL1 (Dropping Leaf 1) and DRL2 that regulated the variation of the maize leaf angle. The mutants of the two genes showed a significantly increased leaf angle phenotype, and in particular the phenotype of the double mutant was more intense, displaying a dropping-leaf phenotype (Strable et al. 2017). Both DRL1 and DRL2 were YABBY transcription factors and contained a C2C2 zinc-finger domain at the N terminus. Therefore, it was speculated whether the DRL protein could directly bind to the sequence surrounding the S2 site to regulate the expression of the downstream gene ZmRAVL1?Because of the high sequence similarity between the DRL1 and DRL2 proteins, the DRL1 protein with more notable mutant phenotype was selected for further analysis.

EMSA (electrophoretic mobility shift assay) was carried out to validate the above speculation. First of all, biotin-labeled EMSA probes (UPA2-NIL^{W22} biotin probes: UPA2-NIL^{W22}-F, UPA2-NIL^{W22}-R; UPA2-NIL^{W22} competitive probe: UPA2-NIL^{W22}-com-F, UPA2-NIL^{W22}-com-R; UPA2-NIL^{8759} biotin probes: UPA2-NIL^{8759}-F, UPA2-NIL^{8759}-R; UPA2-NIL^{8759} competitive probe: UPA2-NIL^{8759}-com-F, UPA2-NIL^{8759}-com-R) were designed for the sequences of UPA2-NIL^{W22} and UPA2-NIL^{8759} respectively. The probe included a C2C2-binding motif and upstream and downstream flanking sequences (each 22 bp). In the meantime, the corresponding sequences that were not labeled with biotin were synthesized as competitive probes. Next, the DRL1 CDS region was recombined onto a PET32a prokaryotic expression vector by a homologous recombination method to construct an expression vector of DRL1-His fusion proteins and it was introduced into the expression strain Rosetta to induce the expression of the DRL1-His fusion proteins. Finally, the DRL1-His fusion proteins were obtained through purification using Nickel beads. The DRL1-His fusion proteins were incubated with biotin-labeled probes UPA2-NIL^{W22}-Bio and UPA2-NIL^{8759}-Bio and competitive probes respectively for 20 minutes at room temperature, and then mobility ratios of probe DNAs were observed through steps such as native gel electrophoresis, transmembrane, cross-linking and chemiluminescence. The experimental results show that the DRL1-His fusion proteins can form retardation strips with the biotin-labeled probes UPA2-NIL^{W22}-Bio and UPA2-NIL^{8759}-Bio, and chemiluminescence shows the retardation strip formed together with the probe UPA2-NIL$^{8759}$-Bio is slightly brighter than the strip formed together with the probe UPA2-NIL$^{W22}$-Bio (FIG. 21A). After the addition of a competitive probe, the binding strips of the DRL1 protein to the biotin-labeled probes UPA2-NIL$^{W22}$-Bio and UPA2-NIL$^{8759}$-Bio disappeared (FIG. 21A). The above results indicate that the DRL1 protein can bind to the UPA2-NIL$^{W22}$-Bio and UPA2-NIL$^{8759}$-Bio probes each containing a C2C2 binding motif in vitro, and the binding ability to the UPA2-NIL$^{8759}$-Bio probe containing the TG insertion is slightly stronger than that to the UPA2-NIL$^{W22}$-Bio probe lacking TG base. Therefore, the S2 site may affect the expression of the downstream gene ZmRAVL1 by its binding intensity to the DRL1 protein.

Figure 26:
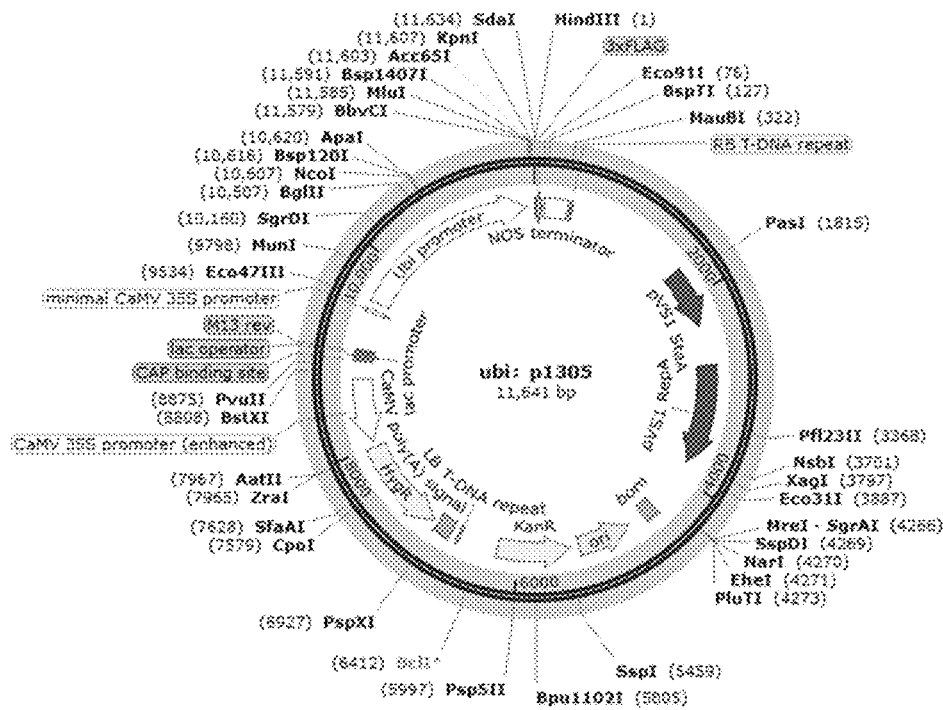
FIG. 26 depicts an image of ubi: p1305 vector.

In order to further verify that the DRL1 protein could bind to the predicted C2C2 binding motif in vivo, the inventors recombined the DRL1 CDS region onto the ubi:p1307 vector (see FIG. 26 for vector information) to construct an overexpression vector of DRL1-Flag fusion proteins, and the vector was transformed into a protoplast to express the DRL1-Flag fusion proteins. The DRL1-Flag fusion proteins in the protoplast were incubated with the Flag antibody to get DRL1-Flag fusion protein-enriched nucleic acid sequences by co-immunoprecipitation or other processes. At the same time, 3 fragments were selected from those surrounding and at the upstream of the C2C2 binding motif to design a pair of primers, and denoted as F1 (F1-F and F1-R), F2 (F2-F and F2-R) and F3 (F3-F and F3-R), respectively. Purified DNA fragments enriched by co-immunoprecipitation were used as templates, and three pairs of primers were used for Chip-qPCR quantitative analysis. The Chip-qPCR test results show that the S2 site-containing DNA fragments were significantly enriched. This result indicates that the DRL1 protein can bind to the sequence surrounding the S2 site located approximately 9.54 kb from the upstream of the gene ZmRAVL1 in vivo (FIG. 21B).

Wherein, names and sequences of primers were as follows:

```
UPA2-NIL^W22-F
                                     (SEQ ID No: 62)
AACTGCGCATGCGCGCGCTGAGTGGTCCTTCTCTTTTAATTACTACTG

UPA2-NIL^W22-R
                                     (SEQ ID No: 63)
CAGTAGTAATTAAAAGAGAAGGACCACTCAGCGCGCGCATGCGCAGTT

UPA2-NIL^W22-com-F
                                     (SEQ ID No: 64)
AACTGCGCATGCGCGCGCTGAGTGGTCCTTCTCTTTTAATTACTACTG UPA-NIL^W22-com-R
                                     (SEQ ID No: 65)
CAGTAGTAATTAAAAGAGAAGGACCACTCAGCGCGCGCATGCGCAGTT UPA2-NIL^8759-F
                                     (SEQ ID No: 66)
AACTGCGCATGCGCGCGCTGAGTGTGGTCCTTCTCTTTTAATTACTACTG UPA2-NIL^8759-R
                                     (SEQ ID No: 67)
CAGTAGTAATTAAAAGAGAAGGACCACACTCAGCGCGCGCATGCGCAGTT UPA2-NIL^8759-com-F
                                     (SEQ ID No: 68)
AACTGCGCATGCGCGCGCTGAGTGTGGTCCTTCTCTTTTAATTACTACTG UPA2-NIL^8759-com-R
                                     (SEQ ID No: 69)
CAGTAGTAATTAAAAGAGAAGGACCACACTCAGCGCGCGCATGCGCAGTT
```

-continued

```
F1-F
                                     (SEQ ID No: 70)
ATGCGGACGATGTGTGATTG

F1-R
                                     (SEQ ID No: 71)
ACGGCTGCGAATTTCACTTT

F2-F
                                     (SEQ ID No: 72)
ACACGTCGAAATCAAAGGGG

F2-R
                                     (SEQ ID No: 73)
TCATTGGTGCCGAGTTGTTC

F3-F
                                     (SEQ ID No: 74)
GAACAACTCGGCACCAATGA

F3-R
                                     (SEQ ID No: 75)
GCACACACACCACACAGTAG
```

6.3 Effect Verification of Functional Site

ZmRAVL1 regulated the leaf angle variation of maize through transcription level. Thus, in the UPA2-NIL$^{W22}$ and UPA2-NIL$^{8759}$, the S2 site might act as a cis-acting element and affect the expression of the downstream gene ZmRAVL1 through the binding intensity to the DRL1 protein, and then affect the development of auricle cell morphology and its number, which eventually reflect a difference in leaf angle. The inventors verified this conjecture via the protoplast dual-luciferase reporter assay system.

Figure 27:
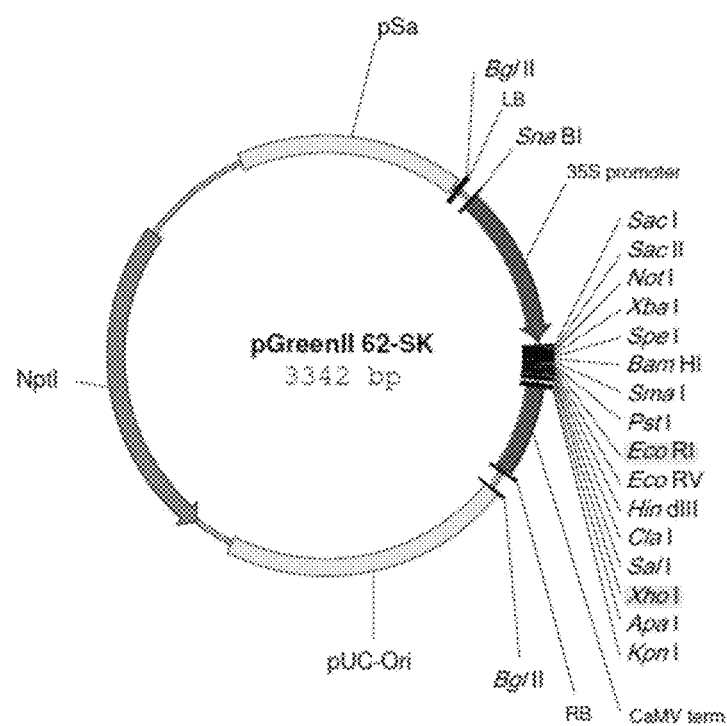
FIG. 27 depicts an image of pGreenII 62-SK vector.

Firstly, the CDS region of the DRL1 gene was recombined onto the pGreenII 62-SK vector (see FIG. 27 for vector information) by a homologous recombination method to construct Effector vector DRL1 (FIG. 22A). Then, a promoter sequence of about 1.7 kb at the upstream of the ATG of the ZmRAVL1 gene derived from the B73 reference genome was cloned onto the backbone of a Reporter vector in a dual-fluorescence transient reporter system, which was used to initiate the expression of the reporter gene LUC. Next, the mapping interval sequences of about 240 bp in the near-isogenic lines UPA2-NIL$^{W22}$ and UPA2-NIL$^{8759}$ were recombined into the modified Reporter vector to construct the reporter vectors UPA2-NIL$^{W22}$ and UPA2-NIL$^{8759}$ (FIG. 22A). The constructed vector plasmids were transformed into protoplasts extracted from etiolated maize seedlings, and the LUC/REN value was calculated by detecting the luciferase (LUC) activity to analyze a regulation effect of 240 bp on downstream genes.

The analysis results showed that when 62-SK vacant vectors were incorporated to both the reporter vectors UPA2-NIL$^{W22}$ and UPA2-NIL$^{8759}$, the LUC expression level of the UPA2-NIL$^{8759}$ reporter vector carrying TG insertion alleles was significantly lower than that of the UPA2-NIL$^{W22}$ reporter vector lacking TG alleles; when Effector vectors DRL1 were added to both the reporter vectors UPA2-NIL$^{W22}$ and UPA2-NIL$^{8759}$, the DRL1 proteins could significantly suppress the LUC luciferase expression and the LUC luciferase expression in the UPA2-NIL$^{8759}$ reporter vector was more strongly suppressed, in comparison to the negative controls (62-SK vacant vectors were added to UPA2-NIL$^{W22}$ and UPA2-NIL$^{8759}$ respectively) (FIG. 22B). The above results confirm that in the UPA2-NIL$^{W22}$ and UPA2-NIL$^{8759}$, the DRL1 proteins can regulate the expression of the downstream gene ZmRAVL1 by the binding intensity to the sequence surrounding the S2 site, and if their binding capability to the sequence is strong, the DRL1 proteins have a strong inhibitory effect on downstream gene expression, and the expression level of ZmRAVL1 is low, so they exhibit a compact leaf angle phenotype; if their binding capability to the sequence is weak, they have a weak inhibitory effect on the downstream gene expression, and the expression level of ZmRAVL1 is high, so they exhibit a loose leaf angle phenotype.

6.4 Analysis of Loss of Elite Alleles Under the Domestication Bottleneck Effect In UPA2-NIL$^{W22}$ and UPA2-NIL$^{8759}$, UPA2 as a cis-regulatory factor regulated the expression of the downstream gene ZmRAVL1 to affect the development of cell morphology and the number thereof in the auricle region, which finally resulted in a difference in leaf angle. In order to investigate whether UPA2 played an important role in regulating the natural variation of maize leaf angle, the associated population composed of 508 maize inbred lines were sequenced.

Sequence alignment showed that no maize inbred lines carried TG insertion alleles at S2 sites (Table 1). The 50 local maize species that were geographically distributed more widely were further sequenced, and the result showed (Table 1): at S2 site, no local maize species carried a TG insertion allele that controlled the compact plant architecture. The above result shows that the TG insertion alleles at the S2 site may only exist in teosinte. To verify this conjecture, 45 teosinte lines with extensive sources were sequenced and the result showed that only 2 (4.4%) teosinte lines carried TG insertion allelic variations. Taken together, the S2 site is a rare allelic variant that only exists in teosinte, and may be lost during the maize domestication due to genetic bottleneck effects.

TABLE 1

Frequency distribution of TG insertion alleles at S2 site in teosinte, local wide-type maize species and maize inbred lines

| Population | Sequencing Qty. | Number of TG insertion-carried lines | Frequency |
|---|---|---|---|
| Teosinte | 45 | 2 | 4.4% |
| Local maize species | 50 | 0 | 0 |
| Maize inbred lines | 450 | 0 | 0 |

6.5 Plot Trials for Near-Isogenic Lines UPA2-NIL$^{W22}$ and UPA2-NIL$^{8759}$

6.5.1 Dense Planting and High-Yield Experiments in Tieling in 2017

(1) Design of Plot Experiments

In the spring of 2017, dense planting and high-yield experiments of UPA2-NIL$^{W22}$ and UPA2-NIL$^{8759}$ were conducted in Tieling County, Tieling City, Liaoning Province, China. The experiments followed a split-plot design with biological replications in main plots and different plant densities and genotypes in subplots. Three biological replications were designed, and each of them consisted of 5 densities of 3,000, 5,000, 7,000, 8,000 and 9,000 plants/mu; 5 rows of UPA2-NIL$^{W22}$ and 5 rows of UPA2-NIL$^{8759}$ were planted under each density. Each row was 5 m long and spaced 0.5 m. During each maize growth period, the same and consistent field management measures, and unified fertilization application, weed control, and pest control were implemented for different replications. Maize was pollinated in a naturally open state without any artificial supplementary pollination. Maize was harvested when maize kernels were physiologically matured, and the middle three rows were harvested for each genotype for seed and yield tests.

(2) Analysis of Plot Ear Traits and Yield Factors

Figure 23:
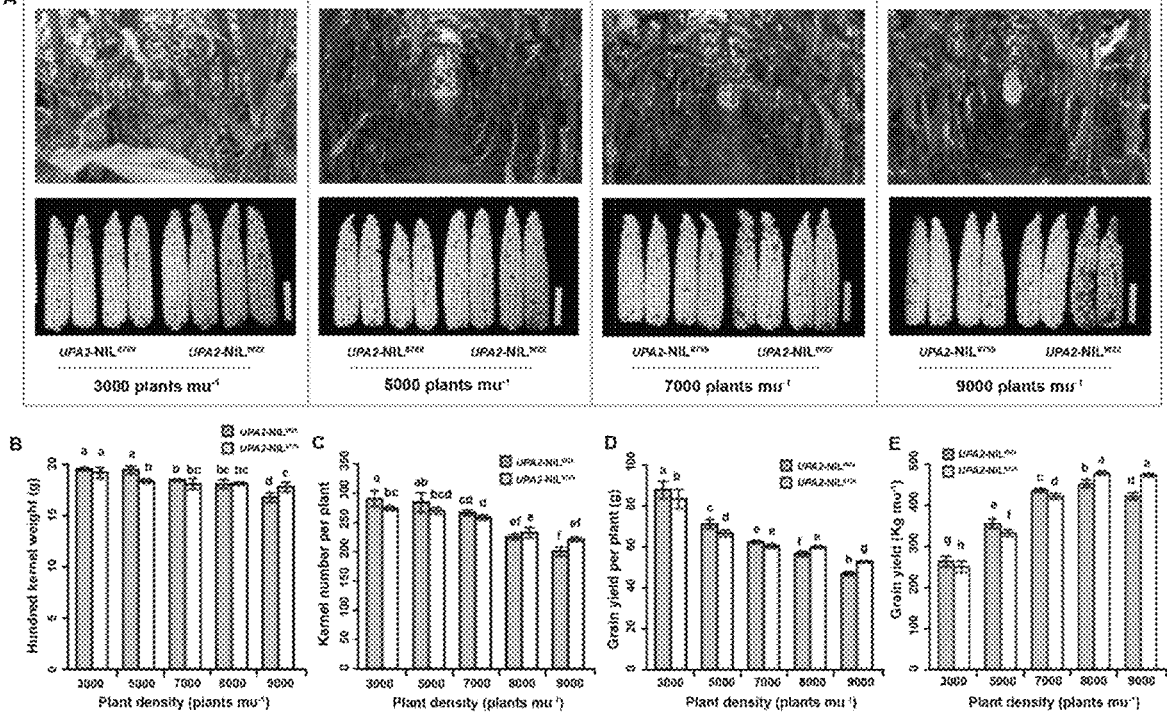
FIG. 23 depicts dense planting and high yielding plot trials of near-isogenic lines UPA2-NIL$^{W22}$ and UPA2-NIL$^{8759}$ (Tieling, Liaoning Province, in 2017), in which (A) shows different plant densities (top) and harvested ears (bottom) of UPA2-NIL$^{W22}$ and UPA2-NIL$^{8759}$ maize plants in the field trial in Tieling, China, in 2017. Scale bar is 5 cm. (B-E) show comparisons of phenotypes of UPA2-NIL$^{W22}$ and UPA2-NIL$^{8759}$ ear traits under different plant densities: (B) hundred kernel weight; (C) kernel number per plant; (D) grain yield per plant; and (E) grain yield. Values are mean±SD. Different letters denote significant differences (P<0.05).

The harvested ears of maize were fully dried and then subjected to seed test. The main traits to be examined included the hundred kernel weight, the kernel number per ear, the kernel weight per ear and the yield per unit area. The hundred kernel weight refers to the quality of one hundred kernels in the middle of the ear. The kernel number per ear refers to the number of all kernels on the maize ear that have been pollinated and has formed kernel prototype. The kernel weight per ear refers to the quality of all kernels on the maize ear. The yield per unit area refers to the average ear quality in this plot calculated from the ear quality of the three rows for seed test, and then converted to a yield per mu (M=(m$_1$+ m$_2$+m$_3$ . . . m$_n$)/n*N, M: grain yield per mu, m$_n$: weight of single ear, N: number of maize plants per mu). Under the densities of 3,000 and 4,000 plants/mu, the yield of UPA2-NIL$^{W22}$ is significantly higher than that of UPA2-NIL$^{8759}$, while under the densities of 7,500 and 9,000 plants/mu, the yield of UPA2-NIL$^{8759}$ carrying a TG insertion allele is significantly higher than that of UPA2-NIL$^{W22}$ lacking TG allele (FIG. 23). Analysis of the factors affecting the yield reveals that an average yield per plant of maize is a factor of determining the difference in yield per mu, and under dense planting conditions, the kernel number per ear of UPA2-NIL$^{8759}$ with a smaller leaf angle is significantly greater than that of WT with a larger leaf angle, but there is no significant difference in hundred kernel weight between them. This indicates that the kernel number per ear is a main factor causing the difference in yields between UPA2-NIL$^{W22}$ and UPA2-NIL$^{8759}$.

6.5.2 HN Plot Trial in 2018

(1) Design of Plot Trials of Near-Isogenic Lines UPA2-NIL$^{W22}$ and UPA2-NIL$^{8759}$ In the winter of 2018, dense planting and high-yield experiments of UPA2-NIL$^{W22}$ and UPA2-NIL$^{8759}$ were conducted in Sanya City, Hainan Province, China. The experiments followed a split-plot design with biological replications in main plots and different plant densities and genotypes in subplots. Three biological replications were designed, and each of them consisted of 5 densities of 3,000, 4,500, 6,000, 7,500 and 9,000 plants/mu; 5 rows of UPA2-NIL$^{W22}$ and 5 rows of UPA2-NIL$^{8759}$ were planted under each density. Each row was 5 m long and spaced 0.5 m. During each maize growth period, the same and consistent field management measures, and unified fertilization application, weed control, and pest control were implemented for different replications. Maize was pollinated in a naturally open state without any artificial supplementary pollination. Maize was harvested when maize kernels were physiologically matured, and the middle three rows were harvested for each genotype for seed and yield tests.

(2) Analysis of Plot Ear Traits and Yield Factors

Figure 24:
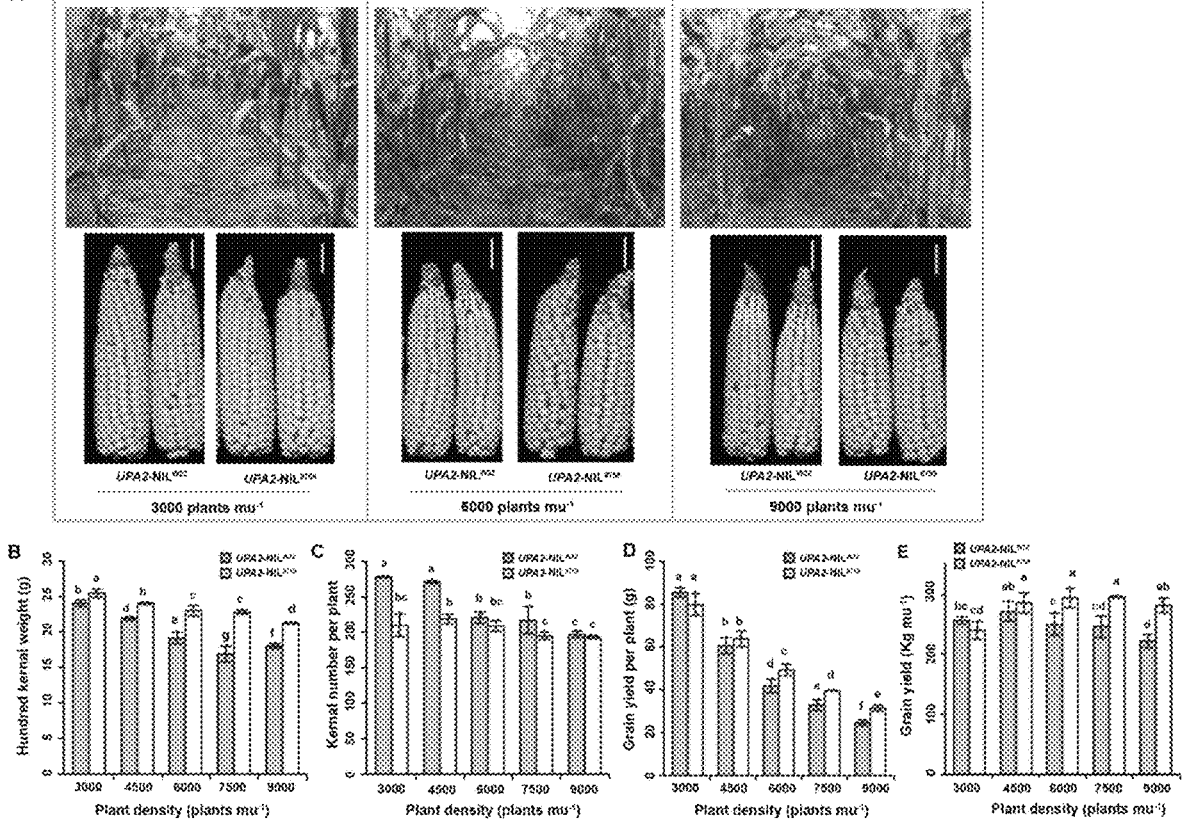
FIG. 24 depicts dense planting and high yielding plot trials of near-isogenic lines UPA2-NIL$^{W22}$ and UPA2-NIL$^{8759}$ (Sanya, Hainan Province, in 2018), in which (A) shows different plant densities (top) and harvested ears (bottom) of UPA2-NIL$^{W22}$ and UPA2-NIL$^{8759}$ maize plants in the field trial in Sanya, Hainan Province, in 2018. Scale bar is 5 cm. (B-E) show comparisons of phenotypes of UPA2-NIL$^{W22}$ and UPA2-NIL$^{8759}$ ear traits under different plant densities: (B) hundred kernel weight; (C) kernel number per plant; (D) grain yield per plant; and (E) grain yield. Values are mean±SD. Different letters denote significant differences (P<0.05).

The harvested ears of maize were fully dried and then subjected to seed test. The main traits to be examined included the hundred kernel weight, the kernel number per ear, the kernel weight per ear and the yield per unit area. The hundred kernel weight refers to the quality of one hundred kernels in the middle of the ear. The kernel number per ear refers to the number of all kernels on the maize ear that have been pollinated and has formed kernel prototype. The kernel weight per ear refers to the quality of all kernels on the maize ear. The yield per unit area refers to the average ear quality in this plot calculated from the ear quality of the three rows for seed test, and then converted to a yield per mu ($M=(m_1+m_2+m_3 \ldots m_n)/n*N$, M: grain yield per mu, $m_n$: weight of single ear, N: number of maize plants per mu). Under the densities of 3,000 and 4,000 plants/mu, the yield of UPA2-NIL$^{W22}$ is significantly higher than that of UPA2-NIL$^{8759}$, while under the densities of 6,000, 7,500 and 9,000 plants/mu, the yield of UPA2-NIL$^{8759}$ carrying a TG insertion allele is significantly higher than that of UPA2-NIL$^{W22}$ lacking TG allele (FIG. 24). Analysis of the factors affecting the yield reveals that an average yield per plant of maize is a factor of determining the difference in yield per hectare, and under dense planting conditions, the hundred kernel weight of UPA2-NIL$^{8759}$ with a smaller leaf angle is significantly greater than that of WT with a larger leaf angle, but there is no significant difference in their kernel number per ear. This indicates that the hundred kernel weight is a main factor causing the difference in yields between UPA2-NIL$^{W22}$ and UPA2-NIL$^{8759}$.

6.6 Improvement of Nongda108 with Elite Alleles

Nongda 108 was a maize variety widely planted in China, and HuangC and Xu178 were its parents. Nongda 108 was a semi-compact and big-ear variety with a larger leaf area per plant, and was generally suitable for planting at densities of 3000-3500 plants/mu. If the plant density was increased, the number of ears would increase, but the economic coefficient decreased and the yield did not increase significantly. 8759$^{UPA2}$ could reduce the leaf angle and increase the yield significantly under dense planting conditions. Therefore, 8759$^{UPA2}$, a fine allele from teosinte, was used to improve the parents of Nongda 108 in combination with the backcrossing infiltration and the molecular marker assisted selection, in the hope of further reducing the leaf angle of hybrids to make their plant architectures more compact and to reduce the shading effect of the upper leaves, so as to increase the canopy transparency and improve the net photosynthesis efficiency.

UPA2-NIL$^{8759}$ was used to separately cross with HuangC and Xu178, and the corresponding parents (as recurrent parents) were consecutively backcrossed four times to get $BC_4F_1$ population. During the backcrossing infiltration process, molecular markers M149 (sequence) and M152 (sequence) in the UPA2 confidence interval were used to perform molecular marker assisted selection. The $BC_4F_1$ population was selfed to get improved lines Huang-C$^{UPA2-8759}$ and Xu178$^{UPA2-8759}$ of HuangC and Xu178. The improved lines HuangC$^{UPA2-8759}$ and Xu178$^{UPA2-8759}$ as well as HuangC and Xu178 were crossed separately to produce improved Nongda108$^{UPA2-8759}$ and conventional Nongda108 F1 hybrids. Dense planting plot trials were carried out under densities of 3,000, 5,000 and 7,000 plants/mu (the design of experiments was the same as described above).

Figure 25:
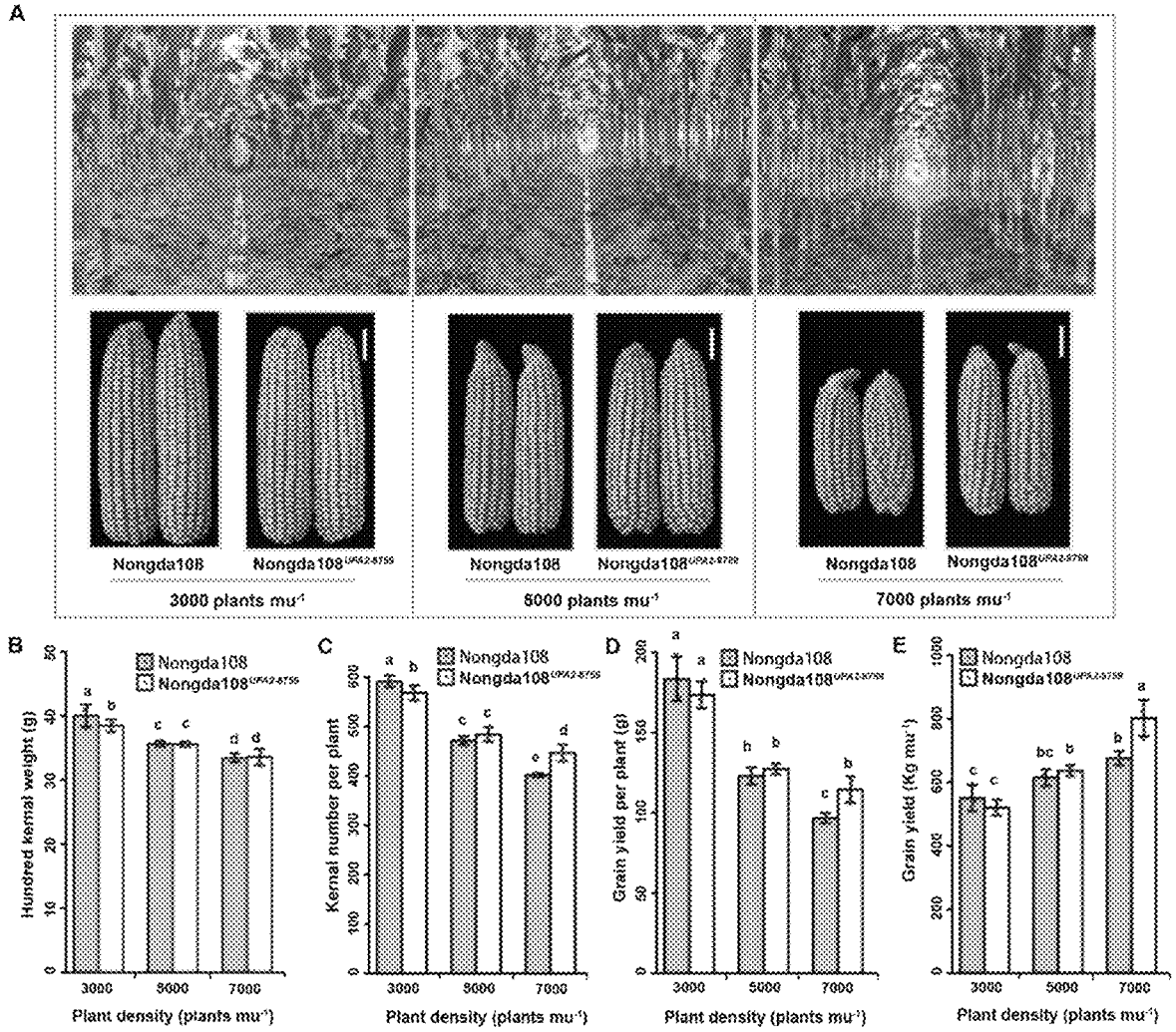
FIG. 25 depicts an experiment on density of F1 hybrid between improved Nongda108$^{UPA2\text{-}8759}$ and conventional Nongda108 (Sanya, Hainan Province, in 2018), in which (A) shows different plant densities (top) and harvested ears (bottom) of maize plants of F1 hybrids between improved Nongda108$^{UPA2\text{-}8759}$ and conventional Nongda108 in the field trial in Sanya, Hainan Province, in 2018. Scale bar is 2 cm. (B-E) show comparisons of phenotypes of UPA2-NIL$^{W22}$ and UPA2-NIL$^{8759}$ ear traits under different plant densities: (B) hundred kernel weight; (C) kernel number per plant; (D) grain yield per plant; and (E) grain yield. Values are mean±SD. Different letters denote significant differences (P<0.05).

The experimental results showed (FIG. 25) that under the plant densities of 3,000 and 5,000 plants/mu, there was no significant difference in per mu yield between the improved Nongda108$^{UPA2-8759}$ and the conventional Nongda108; and under the plant density of 7,000 plants/mu, the yield of the improved Nongda108$^{UPA2-8759}$ was highly significantly different from that of conventional Nongda108 hybrids, with a yield increase of 11.25%. Thereafter, three yield factors that affect the yield per mu were analyzed. The differences in yield per plant and the kernel number per ear were important factors that affected the yield per mu. Under the plant density of 7,000 plants/mu, both the yield per plant and the kernel number per ear of the improved Nongda108$^{UPA2-8759}$ increased significantly, in comparison to those of conventional Nongda108; there was no significant difference in hundred kernel weight between the improved Nongda108$^{UPA2-8759}$ and the conventional Nongda108. The analysis of the test results indicates that the yield per plant and the kernel number per ear are two major yield factors that jointly result in the difference in yield between the improved Nongda108$^{UPA2-8759}$ and the conventional Nongda108.

The examples of the present description are only for elaboration of the content of the present invention, instead of imposing any limitation on the present invention. Therefore, any change equivalent to the meanings of the claims of the present invention and within the scope thereof should all be considered as being included in the scope of the claims of the present invention. All non-patent documents and patent documents cited in the present description are incorporated herein by reference as if each individual non-patent document or patent document is specifically and individually indicated to be incorporated herein by reference. In addition, any theory, mechanism, proof or discovery described herein is intended to further enhance the understanding of the present invention, but is not intended to limit the present invention to such theory, mechanism, proof or discovery in any way. Although the present invention has been illustrated and described in detail in the drawings and the description, the drawings and the description should be considered illustrative rather than restrictive.

REFERENCES

Duncan W G, Hesketh J D (1968) Net photosynthetic rates relative leaf growth rates and leaf numbers of 22 races of maize grown at 8 temperatures. Crop Sci. 8: 670-&

Duvick D N (2005) Genetic progress in yield of united states maize (Zea mays L.). Maydica 50: 193-202

Huang C, Sun H Y, Xu D Y, Chen Q Y, Liang Y M, Wang X F, Xu G H, Tian J G, Wang C L, Li D, Wu L S, Yang X H, Jin W W, Doebley J F, Tian F (2018) ZmCCT9 enhances maize adaptation to higher latitudes. Proc. Natl. Acad. Sci. U.S.A 115: E334-E341 Hung H Y, Shannon L M, Tian F, Bradbury P J, Chen C, Flint-Garcia S A, McMullen M D, Ware D, Buckler E S, Doebley J F, Holland J B (2012) ZmCCT and the genetic basis of day-length adaptation underlying the postdomestication spread of maize. Proc. Natl. Acad. Sci. U.S.A 109: E1913-E1921

Ku L X, Zhang J, Guo S L, Liu H Y, Zhao R F, Chen Y H (2012) Integrated multiple population analysis of leaf architecture traits in maize (Zea mays L.). J. Exp. Bot. 63: 261-274

Ku L X, Zhao W M, Zhang J, Wu L C, Wang C L, Wang P A, Zhang W Q, Chen Y H (2010) Quantitative trait loci mapping of leaf angle and leaf orientation value in maize (Zea mays L.). Theor. Appl. Genet. 121: 951-959

Lambert R J, Johnson R R (1978) Leaf langle, tassel morphology, and performance of maize hybrids. Crop Sci. 18: 499-502

Mickelson S M, Stuber C S, Senior L, Kaeppler S M (2002) Quantitative trait loci controlling leaf and tassel traits in a B73×MO17 population of maize. Crop Sci. 42: 1902-1909

Mock J J, Pearce R B (1975) Ideotype of maize. Euphytica 24: 613-623

Ning J, Zhang B C, Wang N L, Zhou Y H, Xiong L Z (2011) Increased Leaf Angle1, a Raf-Like MAPKKK That Interacts with a Nuclear Protein Family, Regulates Mechanical Tissue Formation in the Lamina Joint of Rice. Plant Cell 23: 4334-4347

Pendleton J W, Smith G E, Winter S R, Johnston T J (1968) Field investigations of relationships of leaf angle in corn (*Zea mays* L.) to grain yield and apparent photosynthesis Agron. J. 60: 422-+

Strable J, Wallace J G, Unger-Wallace E, Briggs S, Bradbury P J, Buckler E S, Vollbrecht E (2017) Maize YABBY Genes drooping leaf1 and drooping leaf2 Regulate Plant Architecture. Plant Cell 29: 1622-+

Studer, Q Z, J R-I, J D (2011) Identification of a functional transposon insertion in the maize domestication gene tb1. Nature Genet. 43: 1160-1163

Tian F, Bradbury P J, Brown P J, Hung H, Sun Q, Flint-Garcia S, Rocheford T R, McMullen M D, Holland J B, Buckler E S (2011) Genome-wide association study of leaf architecture in the maize nested association mapping population. Nature Genet. 43: 159-U113

Wang Y D, Duan M X, Xing J F, Wang J D, Zhang C Y, Zhang X Y, Zhao J R (2008) Progress and Prospect in Ideal Plant architecture Breeding in Maize. Journal of Maize Sciences 16: 47-50

What is claimed is:

1. A method to control a plant architecture, comprising breeding plants to comprise a polynucleotide sequence and selecting the plants having reduced leaf angle, wherein the polynucleotide sequence comprises the sequence of SEQ ID No: 1;

and wherein the plant is a maize.

2. A method for controlling a plant architecture, comprising regulating the ZmRAVL1 gene in a plant and selecting the plant having reduced leaf angle, wherein the ZmRAVL1 gene encodes a ZmRAVL1 protein comprising an amino acid sequence defined by (i), or (ii):

(i) the amino acid sequence set forth in SEQ ID No: 27; or (ii) an amino acid sequence having at least 95%, 96%, 97%, 98%, 98.5%, 99% or 99.5% identity with the amino acid sequence set forth in SEQ ID No: 27, wherein the regulating comprises disrupting the expression level, activity, or combination thereof of the ZmRAVL1 gene, and wherein the disrupting is achieved by knock-out or knockdown of the ZmRAVL1 gene by RNAi technology or by a genome editing system or wherein the disrupting is achieved by regulating DRL1 and/or DRL2; and wherein the plant is a maize.

3. The method of claim 2, wherein the disrupting is achieved by regulating expression level, activity or a combination thereof of DRL1 and/or DRL2, and/or by regulating binding of DRL1 and/or DRL2 to a target.

4. The method of claim 2, wherein the genome editing system is CRISPR/Cas, TALEN, or ZFN.

5. A method of producing a transgenic plant with compact plant architecture, comprising obtaining a transgenic plant cell with inhibited expression of the ZmRAVL1 gene or the gene products thereof compared to a wild type plant, regenerating a transgenic plant from said transgenic plant cell, and selecting the transgenic plant having reduced leaf angle, wherein the ZmRAVL1 gene encodes a ZmRAVL1 protein comprising an amino acid sequence defined by (i), or (ii):

(i) the amino acid sequence set forth in SEQ ID No: 27; or (ii) an amino acid sequence having at least 95%, 96%, 97%, 98%, 98.5%, 99% or 99.5% identity with the amino acid sequence set forth in SEQ ID No: 27; and wherein the plant is a maize.

6. The method according to claim 5, wherein the transgenic plant cell is obtained by mutagenesis, gene editing, or RNA-mediated inhibition of the ZmRAVL1 gene.

7. The method according to claim 6, wherein the RNA-mediated inhibition consists of introducing into a plant cell a polynucleotide encoding a RNA molecule that is at least 70% complementary to at least 15 continuous nucleotides of the ZmRAVL1 gene.

8. The method of claim 2, wherein the ZmRAVL1 gene comprises the following sequence:

(i) the nucleotide sequence set forth in SEQ ID No: 26;

(ii) a cDNA sequence of the nucleotide sequence set forth in SEQ ID No: 26; or (iii) a nucleotide sequence having at least 95%, 96%, 97%, 98%, 98.5%, 99% or 99.5% identity with the nucleotide sequence set forth in SEQ ID No: 26.

9. The method of claim 2, wherein the ZmRAVL1 gene encodes a ZmRAVL1 protein comprising an amino acid sequence defined by (i), or (ii):

(i) the amino acid sequence set forth in SEQ ID No: 27; or (ii) an amino acid sequence having at least 97%, 98%, 98.5%, 99% or 99.5% identity with the amino acid sequence set forth in SEQ ID No: 27.

10. The method of claim 9, wherein the ZmRAVL1 gene encodes a ZmRAVL1 protein comprising an amino acid sequence defined by (i), or (ii):

(i) the amino acid sequence set forth in SEQ ID No: 27; or (ii) an amino acid sequence having at least 98%, 98.5%, 99% or 99.5% identity with the amino acid sequence set forth in SEQ ID No: 27.

11. The method of claim 10, wherein the ZmRAVL1 gene encodes a ZmRAVL1 protein comprising the amino acid sequence of SEQ ID No: 27.

12. The method of claim 5, wherein the ZmRAVL1 gene encodes a ZmRAVL1 protein comprising an amino acid sequence defined by (i), or (ii):

(i) the amino acid sequence set forth in SEQ ID No: 27; or (ii) an amino acid sequence having at least 97%, 98%, 98.5%, 99% or 99.5% identity with the amino acid sequence set forth in SEQ ID No: 27.

13. The method of claim 12, wherein the ZmRAVL1 gene encodes a ZmRAVL1 protein comprising an amino acid sequence defined by (i), or (ii):

(i) the amino acid sequence set forth in SEQ ID No: 27; or (ii) an amino acid sequence having at least 98%, 98.5%, 99% or 99.5% identity with the amino acid sequence set forth in SEQ ID No: 27.

14. The method of claim 13, wherein the ZmRAVL1 gene encodes a ZmRAVL1 protein comprising the amino acid sequence of SEQ ID No: 27.

15. The method of claim 8, wherein the ZmRAVL1 gene comprises the following sequence:

(i) the nucleotide sequence set forth in SEQ ID No: 26;

(ii) a cDNA sequence of the nucleotide sequence set forth in SEQ ID No: 26; or (iii) a nucleotide sequence having at least 97%, 98%, 98.5%, 99% or 99.5% identity with the nucleotide sequence set forth in SEQ ID No: 26.

16. The method of claim 15, wherein the ZmRAVL1 gene comprises the following sequence:

(i) the nucleotide sequence set forth in SEQ ID No: 26;

(ii) a cDNA sequence of the nucleotide sequence set forth in SEQ ID No: 26; or (iii) a nucleotide sequence having at least 98%, 98.5%, 99% or 99.5% identity with the nucleotide sequence set forth in SEQ ID No: 26.

17. The method of claim 16, wherein the ZmRAVL1 gene comprises the following sequence:

(i) the nucleotide sequence set forth in SEQ ID No: 26; or (ii) a cDNA sequence of the nucleotide sequence set forth in SEQ ID No: 26.

* * * * *